(12) United States Patent
Ohrn et al.

(10) Patent No.: US 9,771,573 B2
(45) Date of Patent: Sep. 26, 2017

(54) METHODS OF QUANTITATING HEAVY AND LIGHT CHAIN POLYPEPTIDE PAIRS

(71) Applicants: Zymeworks Inc., Vancouver (CA); National Research Council of Canada, Ottawa (CA)

(72) Inventors: Anders Ohrn, Toronto (CA); Adam Louis Corper, Vancouver (CA); Gordon Yiu Kon Ng, Vancouver (CA); Antonios Samiotakis, New Westminster (CA); Yang-Chieh Chou, Vancouver (CA); Jason Baardsnes, Montreal (CA); Maureen O'Connor-McCourt, Beaconsfield (CA)

(73) Assignees: ZYMEWORKS INC., Vancouver (CA); NATIONAL RESEARCH COUNCIL OF CANADA, Ottawa (CA)

( * ) Notice: Subject to any disclaimer, the term of this patent is extended or adjusted under 35 U.S.C. 154(b) by 0 days.

(21) Appl. No.: 14/432,153

(22) PCT Filed: Oct. 3, 2013

(86) PCT No.: PCT/US2013/063306
§ 371 (c)(1),
(2) Date: Mar. 27, 2015

(87) PCT Pub. No.: WO2014/055784
PCT Pub. Date: Apr. 10, 2014

(65) Prior Publication Data
US 2015/0211001 A1    Jul. 30, 2015

Related U.S. Application Data

(60) Provisional application No. 61/744,911, filed on Oct. 3, 2012.

(51) Int. Cl.
G01N 33/53 (2006.01)
C12N 15/10 (2006.01)
A61K 39/00 (2006.01)
C07K 16/46 (2006.01)
G01N 21/64 (2006.01)

(52) U.S. Cl.
CPC .......... *C12N 15/1055* (2013.01); *A61K 39/00* (2013.01); *C07K 16/468* (2013.01); *G01N 21/6486* (2013.01); *C07K 2317/55* (2013.01)

(58) Field of Classification Search
None
See application file for complete search history.

(56) References Cited

U.S. PATENT DOCUMENTS

| | | | |
|---|---|---|---|
| 5,731,168 A | 3/1998 | Carter et al. | |
| 9,499,634 B2 | 11/2016 | Dixit et al. | |
| 9,527,927 B2 | 12/2016 | Chowdhury et al. | |
| 9,562,109 B2 | 2/2017 | Von Kreudenstein et al. | |
| 9,574,010 B2 | 2/2017 | Von Kreudenstein et al. | |
| 2003/0003502 A1 | 1/2003 | Jardetzky et al. | |
| 2003/0129659 A1* | 7/2003 | Whelihan | G06Q 50/22 435/7.1 |
| 2008/0050370 A1 | 2/2008 | Glaser et al. | |
| 2009/0162360 A1 | 6/2009 | Klein et al. | |
| 2009/0182127 A1 | 7/2009 | Kjaergaard et al. | |
| 2010/0075326 A1 | 3/2010 | Jin et al. | |
| 2010/0322934 A1 | 12/2010 | Imhof-Jung et al. | |
| 2011/0008345 A1 | 1/2011 | Ashman et al. | |
| 2012/0143580 A1 | 6/2012 | Constantine et al. | |
| 2014/0154254 A1 | 6/2014 | Kannan et al. | |
| 2014/0200331 A1 | 7/2014 | Corper et al. | |
| 2014/0370020 A1 | 12/2014 | Kuramochi et al. | |
| 2015/0307594 A1 | 10/2015 | Corper et al. | |
| 2016/0257763 A1 | 9/2016 | Von Kreudenstein et al. | |

FOREIGN PATENT DOCUMENTS

| | | |
|---|---|---|
| CN | 1176659 A | 3/1998 |
| CN | 102153650 B | 7/2012 |
| EP | 1870459 A1 | 12/2007 |
| EP | 2647707 A1 | 10/2013 |
| WO | 2006106905 A1 | 10/2006 |
| WO | 2007110205 A2 | 10/2007 |
| WO | 2009089004 A1 | 7/2009 |
| WO | 2010085682 A2 | 7/2010 |
| WO | 2010115553 A1 | 10/2010 |
| WO | 2011028952 A1 | 3/2011 |
| WO | 2011119484 A1 | 9/2011 |
| WO | 2011143545 A1 | 11/2011 |
| WO | 2012/020096 A1 | 2/2012 |
| WO | 2012023053 A2 | 2/2012 |
| WO | 2012073985 A1 | 6/2012 |
| WO | 2012131555 A2 | 10/2012 |
| WO | 2012163519 A1 | 12/2012 |
| WO | 2014082179 A1 | 6/2014 |
| WO | 2014150973 A1 | 9/2014 |
| WO | 2015181805 A1 | 12/2015 |

OTHER PUBLICATIONS

Tu et al. (Clinical & Vaccine Immnology Jun. 2010 p. 1040-1047).*
Hamel et al. (Molecular Immunology 1986 vol. 23, p. 503-510).*
International Application No. PCT/US2013/063306, International Search Report and Written Opinion, mailed Jan. 30, 2014.

(Continued)

*Primary Examiner* — Jacob Cheu

(74) *Attorney, Agent, or Firm* — Kilpatrick Townsend & Stockton LLP

(57) ABSTRACT

Provided is a method of quantitatively determining the ability of individual IgG heavy chains to selectively pair with a particular IgG light chain when the heavy chains and two unique light chains are co-expressed. The method provides results with reasonable throughput and is robust and accurate. The co-expressed heavy and light chains do not need to be isolated and purified which enables more efficient screening.

36 Claims, 19 Drawing Sheets

(56) References Cited

OTHER PUBLICATIONS

Schlatter, S et al., On the Optimal Ratio of Heavy to Light Chain Genes for Efficient Recombinant Antibody Production by CHO Cells. Biotechnology Progress. Jan.-Feb. 2005. vol. 21, No. 1, pp. 122-133; abstract; p. 123, left column, fourth paragraph; p. 125, figure 1, DOI: 10.1021/bp049780w.
Merk, H et al. Cell-Free Expression of Two Single-Chain Monoclonal Antibodies Against Lysozyme: Effect of Domain Arrangement on the Express. J. Biochem. vol. 125, pp. 328-333 (1999); abstract.
McCann, C et al. Peptide Tags for Labeling Membrane Proteins in Live Cells with Multiple Fluorophores. BioTechniques. Jun. 2005. vol. 38, No. 6, pp. 945-951; abstract.
U.S. Appl. No. 14/092,804. "Restriction Requirement". May 12, 2016. 5 pages.
U.S. Appl. No. 14/092,804. "Non-Final Office Action". Sep. 10, 2015. 33 pages.
U.S. Appl. No. 14/648,222. "Restriction Requirement". May 9, 2016. 14 pages.
Altintas et al., "Targeting epidermal growth factor receptor in tumors: from conventional monoclonal antibodies via heavy chain-only antibodies to nanobodies", Eur J Pharm Sci., vol. 45, No. 4, Mar. 12, 2012, pp. 399-407.
Atwell et al., "Stable heterodimers from remodeling the domain interface of a homodimer using a phage display library", Journal of Molecular Biology, vol. 270, No. 1, Jul. 4, 1997, pp. 26-35.
Colman , "Effects of amino acid sequence changes on antibody-antigen interactions", Research in Immunology, vol. 145, Jan. 1994, pp. 33-36.
Dall'Acqua et al., "Contribution of Domain Interface Residues to the Stability of Antibody CH3 Domain Homodimers", Biochemistry, American Chemical Society, US, vol. 37, No. 26, Jun. 30, 1998, pp. 9266-9273.
Davis et al., "SEEDbodies: fusion proteins based on strand-exchange engineered domain (SEED) CH3 heterodimers in an Fc analogue platform for asymmetric binders or immunofusions and bispecific antibodies", Protein Engineering, Design & Selection, vol. 23, No. 4, Feb. 4, 2010, pp. 195-202.
Demarest et al., "Optimization of the Antibody CH3 Domain by Residue Frequency Analysis of IgG Sequences", Journal of Molecular Biology, vol. 335, No. 1, Jan. 2, 2004, pp. 41-48.
Gunasekaran et al., "Enhancing antibody Fc heterodimer formation through electrostatic steering effects: applications to bispecific molecules and monovalent IgG", J. Biol. Chem., vol. 285, No. 25, Jun. 18, 2010, pp. 19637-19646.
Igawa et al., "VH/VL interface engineering to promote selective expression and inhibit conformational isomerization of thrombopoietin receptor against single-chain diabody", Protein Engineering, Design & Selection, vol. 23, No. 8, Aug. 2010, pp. 667-677.
Klein et al., "Progress in overcoming the chain association issue in bispecific heterodimeric IgG antibodies", MABS, vol. 4, No. 6, Nov./Dec. 2012, pp. 653-663.
Lewis et al., "Generation of bispecific IgG antibodies by structura-based design of an orthogonal Fab interface", Nature Biotechnology, Jan. 26, 2014.

Maccallum et al., "Antibody-antigen interactions: Contact analysis and binding site topography", Journal of Molecular Biology, vol. 262 (5), Oct. 1996, pp. 732-745.
Merchant et al., "An efficient route to human bispecific IgG", Nature Biotechnology, vol. 16, No. 7, Jul. 16, 1998, pp. 677-681.
Osborn et al., "Pharmacokinetic and Pharmacodynamics Studies of a Human Serum Albumin-Interferon-A Fusion Protein in Cynomolgus Monkeys", J. Pharamcology and Experiemental Therapeutics, vol. 330, 2002, pp. 540-548.
PCT/CA2013/050914. "International Search Report and Written Opinion". Feb. 7, 2014. 11 pages.
PCT/IB2015/054107 . "International Search Report and Written Opinion". Sep. 1, 2015. 19 pages.
Ridgway et al., "'Knobs-into-holes' engineering of antibody CH3 domains for heavy chain heterodimerization", Protein Engineering, vol. 9, No. 7, Jul. 1996, pp. 617-621.
Rudikoff et al., "Single Amino Acid Substitution altering Antigen-binding Specificity", Proc. Natl Acad Sci., vol. 79,No. 6, 1982, pp. 1979-1983.
Shields et al., "High resolution mapping of the binding site on human IgG1 for Fc gamma RI, Fc gamma RII, Fc gamma RIII, and FcRn and design of IgG1 variants with improved binding to the Fc gamma R", Journal of Biological Chemistry, vol. 276, No. 9, Mar. 2, 2001, pp. 6591-6604.
Tamaskovic et al., "Designed ankyrin repeat proteins (DARPins): From reserach to therapy", Methods in Enzymology, vol. 503, 2012, 101-134.
Verheesen et al., "Selection by phage display of single domain antibodies specific to antigens in their native conformation", Methods Mo Bio. , Chapter 6, vol. 911, 2012, pp. 81-104.
Von Kreudenstein et al., "Protein engineering and the use of molecular modeling and simulation: the case of heterodimeric Fc engineering", Methods, vol., 65, No. 1, Jan. 1, 2014, pp. 77-94.
Wiens et al., "Mutation of a single conserved residue in VH complementarity-determining region 2 results in a severe Ig secretion defect.", J Immunology, vol. 167, No. 4, Aug. 2001, pp. 2179-2186.
Woods et al., "LC-MS characterization and purity assessment of a prototype bispecific antibody", MABS, vol. 5, No. 5, Sep. 1, 2013, pp. 711-722.
Wu et al., "Humanization of a Murine Monoclonal Antibody by Simultaneous Optimization of Framework and CDR Residues", Journal of Molecular Biology, vol. 294, Nov. 1999, pp. 151-162.
Zhu et al., "Remodeling domain interfaces to enhance heterodimer formation", Protein Science, vol. 6, No. 4, Apr. 1997, pp. 781-788.
U.S. Appl. No. 14/092,804, "Non-Final Office Action", mailed Dec. 29, 2016, 64 pages.
U.S. Appl. No. 14/648,222, "Restriction Requirement", mailed Dec. 2, 2016, 33 pages.
Jordan et al., "Structural understanding of stabilization patterns in engineered bispecfic Ig-like antibody molecules", Proteins: Structure, Function, and Bioinformatics, vol. 77, No. 4, pp. 832-841, Dec. 1, 2009, 10 pages.
Miller et al., "Stability engineering of scFvs for the development of bispecific and multivalent antibodies", Protein Engineering, Design & Selection, vol. 23, No. 7, pp. 549-557, May 10, 2010, 9 pages.
Spreter Von Kreudenstein et al., "Improving biophysical properties of a bispecific antibody scaffold to aid developability," Sep./Oct. 2013, mAbs, vol. 5, No. 5, pp. 646-654.
U.S. Appl. No. 14/648,222, Non-Final Office Action dated May 16, 2017, 43 pages.

* cited by examiner

Figure 8 Con't
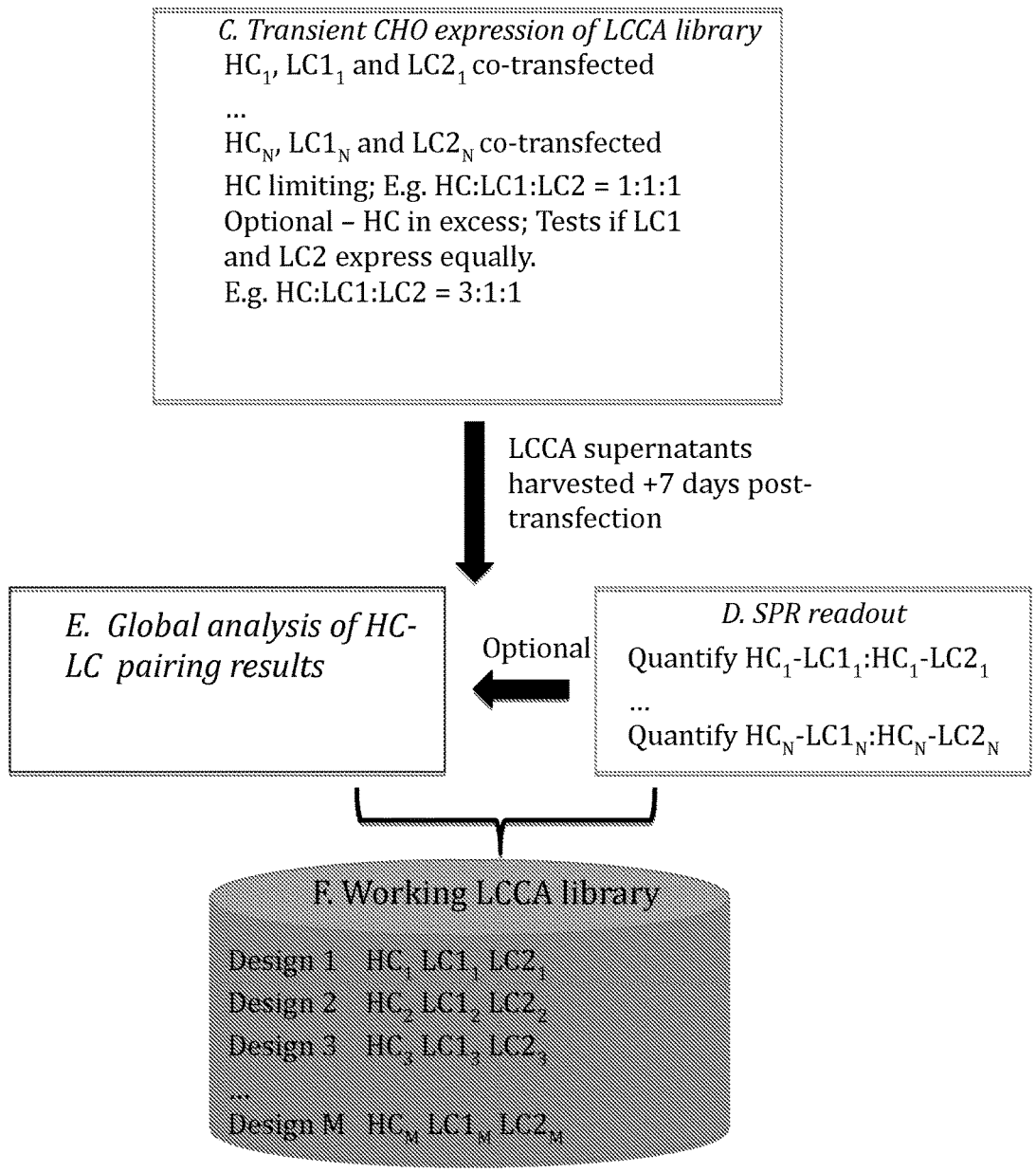

METHODS OF QUANTITATING HEAVY AND LIGHT CHAIN POLYPEPTIDE PAIRS

CROSS-REFERENCE

This application claims the benefit of U.S. Provisional Application No. 61/744,911, filed Oct. 03, 2012, which application is incorporated herein by reference in its entirety for all purposes.

BACKGROUND

Methods of identifying and quantifying products of co-expression of heavy chains and light chains have been previously described. For instance, liquid chromatography-mass spectrometry (LC-MS) and ion exchange chromatography (IEX) have been used to characterize the purity of bi-specific antibody constructs (see, for example, Strop et al. (2012) *J. Mol. Biol.* 420: 204-219). An activity-based sandwich ELISA has also been used as a high-throughput screen to select stable cell-lines secreting high yields of bi-specific antibodies with good purity. (see for example, van der Neut Kolfschonten et al. (2007), *Science* 317: 1554-1557). Methods of displaying antibodies using yeast have also been described (see, e.g., Chao et al., *Nat Protoc.* 2006; 1(2):755-68). Methods of isolating or purifying antibodies using, for example, affinity chromatography are well known in the art and affinity purification columns are commercially available.

A quantitative immunoglobulin heavy chain/light chain immunoassay, Hevylite® (HLC, The Binding Site Group, Birmingham, UK), is commercially available, and includes a step of measuring IgGκ/IgGλ pairs. This assay is used to quantify monclonal immunoglobulins in patients with diseases such as, for example, multiple myeloma.

SUMMARY OF THE INVENTION

A bi-specific IgG (in a format close to wild-type IgG) is typically formed by the intracellular concomitant expression of two unique antibody heavy chains and two unique antibody light chains. Correctly forming this type of bi-specific format is challenging, since antibody heavy chains have evolved to bind antibody light chains in a relatively promiscuous manner. As a result, when two unique antibody heavy chains and two unique antibody light chains are co-expressed, multiple antibody molecules are produced, with the desired bi-specific antibody typically formed in minor amounts. One method to circumvent this problem would be to use antibody heavy chains and antibody light chains that selectively pair to form the desired bi-specific antibody. Thus, there is a need for a screening assay that allows for the identification of IgG heavy chains and IgG light chains that selectively pair with each other.

Provided are assays and analysis tools that are useful to determine whether a specific immunoglobulin (e.g., IgG) heavy chain binds selectively to a specific immunoglobulin (e.g., IgG) light chain.

Provided herein are methods, assays, systems and kits for high-throughput quantification of the selectivity of a heavy chain polypeptide for pairing with at least one light chain polypeptide. Also provided are methods, systems and kits for determining the selective formation of a Fab-containing construct in the presence of competing heavy or light chain polypeptides or combinations thereof. Also provided are methods of designing or making biparatopic antibody constructs using the assays described herein. Also provided is a method of determining antibody heterodimer formation.

Provided is a high-throughput method of quantifying selectivity of a heavy chain polypeptide for pairing with at least one light chain polypeptide comprising the steps of (a) co-expressing a set of constructs: a first heavy chain polypeptide comprising a VH and a CH1 region; a first light chain polypeptide comprising a first VL and first CL region; and a second light chain polypeptide comprising a second VL and second CL region; wherein said heavy chain polypeptide and said light chain polypeptides are expressed such that the total amount of the heavy chain polypeptide is limiting; and wherein co-expressing the set of constructs results in a set of polypeptide products; (b) isolating heavy chain-paired polypeptide products comprising the heavy chain polypeptide paired with said first or second light chain polypeptide from the set of polypeptide products; and (c) quantitating the amount of heavy chain polypeptide paired with said first light chain polypeptide, and the amount of heavy chain polypeptide paired with said second light chain polypeptide in the heavy chain-paired polypeptide products; wherein a greater amount of the heavy chain polypeptide paired with one of said first or second light chain polypeptide as compared to the other light chain polypeptide indicates selectivity of the heavy chain polypeptide for pairing with said first or second light chain polypeptide.

In one embodiment of such methods, the first or the second heavy chain polypeptide further comprise an Fc region. In another embodiment of such methods, the first and the second heavy chain polypeptides further comprise an Fc region. In yet another embodiment of such methods, the first or the second heavy chain polypeptide comprise an Fc and region and a Fv region. In yet another embodiment of such methods, the first and the second heavy chain polypeptides comprise an Fc region and a Fv region.

One would understand that this process could be conducted to pair at least one light chain polypeptide with at least a first heavy chain polypeptide and a second heavy chain polypeptide.

In one embodiment of the method, step (c) comprises quantifying pairing between HC:LC1:LC2 detected on a surface that captures HC:LC1:LC2, wherein said method comprises capture and detection methods such as, for example, ELISA, SPR chips, bimolecular fluorescence complementation readout, Fluorescence-Activated Cell Sorting (FACS), DELFIA®, fluorescence polarization/anisotropy (FP), fluorescent/Foerster resonance energy transfer (FRET, TR-FRET, HTRF), AlphaScreen®, or a combination thereofy; and screening said surface for an interaction between one or more of said units and said environment.

Provided herein is a high-throughput method of quantifying selectivity of a heavy chain polypeptide for pairing with a light chain polypeptide comprising the steps of: (a) co-expressing a set of constructs comprising: a first light chain polypeptide comprising a VL and a CL region; a first heavy chain polypeptide comprising a first VH and first CH1 region; and a second heavy chain polypeptide comprising a second VH and second CH1 region; wherein said light chain polypeptide and said heavy chain polypeptides are expressed such that the total amount of the light chain polypeptide is limiting; and wherein co-expressing the set of constructs results in a set of polypeptide products; (b) isolating light chain-paired polypeptide products comprising the light chain polypeptide paired with said first or second heavy chain polypeptide from the set of polypeptide products; and (c) the amount of light chain polypeptide paired with said first heavy chain polypeptide, and the amount of light chain polypeptide paired with said second heavy chain polypeptide in the light chain-paired polypeptide products; wherein a greater amount of the light chain polypeptide paired with one of said first or second heavy chain polypeptides as compared to the other heavy chain polypeptide indicates selectivity of the light chain polypeptide for pairing with said first or second heavy chain polypeptides.

In one embodiment of such methods, the first or the second heavy chain polypeptide further comprise an Fc region. In another embodiment of such methods, the first and the second heavy chain polypeptides further comprise an Fc region. In another embodiment of such methods, the first or the second heavy chain polypeptide comprise an Fc region and a Fv region. In yet another embodiment of such methods, the first and the second heavy chain polypeptides comprise an Fc region and a Fv region.

Provided herein is a high-throughput method of quantifying selectivity of a heavy chain polypeptide for pairing with a light chain polypeptide comprising the steps of: (a) co-expressing a set of constructs comprising: a first heavy chain polypeptide comprising VH, CH1, CH2 and CH3 regions; a first light chain polypeptide comprising a first VL and first CL region; and a second light chain polypeptide comprising a second VL and second CL region; wherein said heavy chain polypeptide and said light chain polypeptide are expressed such that the total amount of the heavy chain polypeptide is limiting; and wherein co-expressing the set of constructs results in a set of polypeptide products; (b) isolating heavy chain-paired polypeptide products comprising the heavy chain polypeptide paired with said first or second light chain polypeptide from the set of polypeptide products; and (c) the amount of heavy chain polypeptide paired with said first light chain polypeptide, and the amount of heavy chain polypeptide paired with said second light chain polypeptide in the heavy chain-paired polypeptide products; wherein a greater amount of the heavy chain polypeptide paired with one of said first or second light chain polypeptide as compared to the other light chain polypeptide indicates selectivity of the heavy chain polypeptide for pairing with said first or second light chain polypeptide.

Provided herein is a high-throughput method of quantifying selectivity of a heavy chain polypeptide for pairing with a light chain polypeptide comprising the steps of: (a) co-expressing a set of constructs comprising: a full-length heavy chain polypeptide comprising VH, CH1, CH2 and CH3 regions; a heavy chain polypeptide comprising a CH2 region and a CH3 region; a first light chain polypeptide comprising a first VL and first CL region; and a second light chain polypeptide comprising a second VL and second CL region; wherein said heavy chain polypeptides and said light chain polypeptides are expressed such that the total amount of the full-length heavy chain polypeptide is limiting; and wherein co-expressing the set of constructs results in a set of polypeptide products; (b) isolating heavy chain-paired polypeptide products comprising the full-length heavy chain polypeptide paired with the heavy chain polypeptide comprising a CH2 region and a CH3 region with said first or second light chain polypeptide from the set of polypeptide products; and (c) the amount of heavy chain polypeptides paired with said first light chain polypeptide, and the amount of heavy chain polypeptides paired with said second light chain polypeptide in the heavy chain-paired polypeptide products; wherein a greater amount of the heavy chain polypeptides paired with one of said first or second light chain polypeptide as compared to the other light chain polypeptide indicates selectivity of the heavy chain polypeptides for pairing with said first or second light chain polypeptide.

The pairings may be detected by quantifying a detectable moiety. A detectable moiety may be, for example, a protein binding site, a ligand binding site, or a tag comprising a further detectable moiety. Detection of the detectable moiety may comprise measurement of fluorescence, quenching, radioactivity or chemiluminescence. In one embodiment, an environment comprising the HC:LC1:LC2 is a complex molecular mixture, a cell supernatant, cytoplasm of a host cell, or a combination thereof. A mass of antibody with a particular light chain tag may be normalized by the amount of an isolated heavy chain fraction. An equivalent mass ratio may be evaluated for control antibodies. The ratio of the two mass ratios is equal to the percentage of isolated antibodies with a particular tag.

In one embodiment of the disclosed methods, the method comprises determining the relative pairing propensity of L1 to pair with H compared with the relative pairing propensity of L2 to pair with H.

The method may further comprise selecting a paired polypeptide that produces a high relative amount of HL1 species over HL2 species. Comparing the ratios may be accomplished according to the following calculations:

$$R = \frac{[HL1]}{[HL2]}$$

$$S = \log\frac{[HL1]}{[HL2]}$$

$$P1 = 100 \cdot \frac{[HL1]}{[HL1] + [HL2]}$$

$$P2 = 100 \cdot \frac{[HL2]}{[HL1] + [HL2]}$$

wherein R is the ratio of the amount of the two Fab species; S is the logarithm of R, and is proportional to the free energy difference between the pairing of L1 with H and L2 with H; and P1 and P2 are the percentages of the desired and undesired species, respectively such that $$S = \log\frac{P1}{P2}.$$

In another aspect, provided herein is a high-throughput method of quantifying selectivity of a heavy chain polypeptide for pairing with a light chain polypeptide comprising the steps of: (a) co-expressing a set of constructs comprising: a heavy chain polypeptide comprising a VH region, a CH1 region, and a first detectable label (tag); a first light chain polypeptide comprising a first VL, first CL region, and a second detectable label; and a second light chain polypeptide comprising a second VL, second CL region, and a third detectable label; wherein said heavy chain polypeptides and said light chain polypeptides are expressed such that the total amount of the full-length heavy chain polypeptide is limiting; and wherein co-expressing the set of constructs results in a set of polypeptide products; (b) isolating heavy chain-paired polypeptide products comprising the heavy chain polypeptide with said first or second light chain polypeptide from the set of polypeptide products using the first detectable label on the heavy chain polypeptide; and (c) determining the amount of heavy chain polypeptides paired with said first light chain polypeptide, and the amount of heavy chain polypeptides paired with said second light chain polypeptide in the heavy chain-paired polypeptide products; wherein a greater amount of the heavy chain polypeptides paired with one of said first or second light chain polypeptide as compared to the other light chain polypeptide indicates selectivity of the heavy chain polypeptides for pairing with said first or second light chain polypeptide.

In one embodiment, the first detectable label is a 6×His tag. In another embodiment, the second detectable label is different from said third detectable label.

Determining may comprise ELISA, SPR, bimolecular fluorescence complementation readout, Fluorescence-Activated Cell Sorting (FACS), DELFIA®, fluorescence polarization/anisotropy (FP), fluorescent/Foerster resonance energy transfer (FRET, TR-FRET, HTRF), AlphaScreen®, or a combination thereof.

A detectable label may be a protein binding site, a ligand binding site, or a tag comprising a further detectable moiety. Detection of the detectable label may comprise measurement of fluorescence, quenching, radioactivity or chemiluminescence.

In another aspect, provided herein is a high-throughput method of quantifying selectivity of a light chain polypeptide for pairing with a heavy chain polypeptide comprising the steps of (a) co-expressing a set of constructs comprising: a light chain polypeptide comprising a VL region and a CL region; a first heavy chain polypeptide comprising a first VH, a first CH1 region, and at least one detectable label; and a second heavy chain polypeptide comprising a second VH, a second CH1 region and at least one detectable label; wherein said light chain polypeptides and said heavy chain polypeptides are expressed such that the total amount of the light chain polypeptide is limiting; and wherein co-expressing the set of constructs results in a set of polypeptide products; (b) isolating light chain-paired polypeptide products comprising the light chain polypeptide with said first or second heavy chain polypeptide from the set of polypeptide products; and (c) determining the amount of light chain polypeptides paired with said first heavy chain polypeptide, and the amount of light chain polypeptides paired with said second heavy chain polypeptide in the light chain-paired polypeptide products; wherein a greater amount of the light chain polypeptides paired with one of said first or second heavy chain polypeptide as compared to the other heavy chain polypeptide indicates selectivity of the light chain polypeptides for pairing with said first or second heavy chain polypeptide.

Determining may comprise ELISA, SPR, bimolecular fluorescence complementation readout, Fluorescence-Activated Cell Sorting (FACS), DELFIA®, fluorescence polarization/anisotropy (FP), fluorescent/Foerster resonance energy transfer (FRET, TR-FRET, HTRF), AlphaScreen®, or a combination thereof.

In one embodiment, the first heavy chain polypeptide is labeled with two labels.

In another embodiment, the first heavy chain polypeptide is labeled with a 6×His tag and a second label.

In another embodiment, the second heavy chain polypeptide is labeled with two labels.

In another embodiment, the second heavy chain polypeptide is labeled with a 6×His tag and a second label.

A detectable label may be a protein binding site, a ligand binding site, or a tag comprising a further detectable moiety. Detection of the detectable label may comprise measurement of fluorescence, quenching, radioactivity or chemiluminescence.

In another aspect, provided herein is a high-throughput method of quantifying selectivity of a heavy chain polypeptide for pairing with a light chain polypeptide comprising the steps of: (a) co-expressing a set of constructs comprising: a full-length heavy chain polypeptide comprising VH, CH1, CH2 and CH3 regions; a heavy chain polypeptide comprising a CH2 region and a CH3 region; a first light chain polypeptide comprising a first VL, a first CL region and a first detectable label; and a second light chain polypeptide comprising a second VL, a second CL region and a second detectable label; wherein said heavy chain polypeptides and said light chain polypeptides are expressed such that the total amount of the full-length heavy chain polypeptide is limiting; and wherein co-expressing the set of constructs results in a set of polypeptide products; (b) isolating heavy chain-paired polypeptide products with an anti-Fc antibody; and (c) determining the amount of heavy chain polypeptides paired with said first light chain polypeptide, and the amount of heavy chain polypeptides paired with said second light chain polypeptide in the heavy chain-paired polypeptide products; wherein a greater amount of the heavy chain polypeptides paired with one of said first or second light chain polypeptide as compared to the other light chain polypeptide indicates selectivity of the heavy chain polypeptides for pairing with said first or second light chain polypeptide.

Determining may comprise ELISA, SPR, bimolecular fluorescence complementation readout, Fluorescence-Activated Cell Sorting (FACS), DELFIA®, fluorescence polarization/anisotropy (FP), fluorescent/Foerster resonance energy transfer (FRET, TR-FRET, HTRF), AlphaScreen®, or a combination thereof.

In one embodiment, the first detectable label is different from the second detectable label.

A detectable label may be a protein binding site, a ligand binding site, or a tag comprising a further detectable moiety. Detection of the detectable label may comprise measurement of fluorescence, quenching, radioactivity or chemiluminescence.

In another aspect, provided herein is a high-throughput method of quantifying selectivity of a heavy chain polypeptide for pairing with a light chain polypeptide comprising the steps of (a) co-expressing a set of constructs comprising: a full-length heavy chain polypeptide comprising VH, CH1, CH2 and CH3 regions; a first light chain polypeptide comprising a first VL, a first CL region and a first detectable label; and a second light chain polypeptide comprising a second VL, a second CL region and a second detectable label; wherein said heavy chain polypeptides and said light chain polypeptides are expressed such that the total amount of the full-length heavy chain polypeptide is limiting; and wherein co-expressing the set of constructs results in a set of polypeptide products; (b) isolating heavy chain-paired polypeptide products with an anti-Fc antibody; and (c) determining the amount of heavy chain polypeptides paired with said first light chain polypeptide, and the amount of heavy chain polypeptides paired with said second light chain polypeptide in the heavy chain-paired polypeptide products; wherein a greater amount of the heavy chain polypeptides paired with one of said first or second light chain polypeptide as compared to the other light chain polypeptide indicates selectivity of the heavy chain polypeptides for pairing with said first or second light chain polypeptide.

Determining may comprise ELISA, SPR, bimolecular fluorescence complementation readout, Fluorescence-Activated Cell Sorting (FACS), DELFIA®, fluorescence polarization/anisotropy (FP), fluorescent/Foerster resonance energy transfer (FRET, TR-FRET, HTRF), AlphaScreen®, or a combination thereof.

In one embodiment, the first detectable label is different from the second detectable label.

A detectable label may be a protein binding site, a ligand binding site, or a tag comprising a further detectable moiety. Detection of the detectable label may comprise measurement of fluorescence, quenching, radioactivity or chemiluminescence.

In another aspect, provided herein is a high-throughput method of quantifying selectivity of a heavy chain polypeptide for pairing with a light chain polypeptide comprising the steps of: (a) co-expressing a set of constructs comprising: a first heavy chain polypeptide comprising a VH region, a CH1 region and a detectable label; a second heavy chain polypeptide comprising a VH region, a CH1 region and a detectable label; a first light chain polypeptide comprising a first VL, a first CL region and a detectable label; and a second light chain polypeptide comprising a second VL, a second CL region and a detectable label; wherein said heavy chain polypeptide and said light chain polypeptides are expressed such that the total amount of the heavy chain polypeptide is limiting; and wherein co-expressing the set of constructs results in a set of polypeptide products; (b) isolating heavy chain-paired polypeptide products comprising the heavy chain polypeptide paired with said first or second light chain polypeptide from the set of polypeptide products; and (c) determining the amount of heavy chain polypeptide paired with said first light chain polypeptide, and the amount of heavy chain polypeptide paired with said second light chain polypeptide in the heavy chain-paired polypeptide products; wherein a greater amount of the heavy chain polypeptide paired with one of said first or second light chain polypeptide as compared to the other light chain polypeptide indicates selectivity of the heavy chain polypeptide for pairing with said first or second light chain polypeptide.

In one embodiment, each of said detectable labels are unique.

Determining may comprise ELISA, SPR, bimolecular fluorescence complementation readout, Fluorescence-Activated Cell Sorting (FACS), DELFIA®, fluorescence polarization/anisotropy (FP), fluorescent/Foerster resonance energy transfer (FRET, TR-FRET, HTRF), AlphaScreen®, or a combination thereof.

A detectable label may be a protein binding site, a ligand binding site, or a tag comprising a further detectable moiety. Detection of the detectable label may comprise measurement of fluorescence, quenching, radioactivity or chemiluminescence.

Data obtained by the method may be transmitted to a general purpose computer and outputting of the data comprises storing the results on a data carrier.

The method may, in some instances, optionally comprise analyzing HC-LC results. Alternatively, or in addition, the method may further comprise building a LCCA library of paired heavy chain polypeptides and light chain polypeptides.

In certain embodiments of any of the described methods, the heavy chain polypeptide, and first and second light chain polypeptides are expressed in a predetermined ratio of about 0.25:1:1. In selected embodiments, the heavy chain polypeptide, and first and second light chain polypeptides are expressed in a predetermined ratio of about 1:2:2. In some embodiments, the heavy chain polypeptide, and first and second light chain polypeptides are expressed in a predetermined ratio of about 1:3:3. In certain other embodiments, the first and second light chains are expressed in different relative amounts. For example, in some embodiments, the heavy chain polypeptide, and first and second light chain polypeptides are expressed in a predetermined ratio of about 2:1:3, or about 2:3:1. In one embodiment the ratio of transfection of heavy chain polypeptide (HC) to first light chain polypeptide (LC1) and second light chain polypeptide (LC2), i.e., HC:LC1:LC2 is 3:1:1 to determine, in some instances, if LC1 and LC2 are equally expressed. It would be understood that other ratios may be used and are contemplated herein. In a non-limiting example, LCCA dose verification ratios for HC:LC1:LC2 may be (50:75:25, 50:50:50 and 50:25:75) or (50:40:60, 50:50:50 and 50:60:40).

In certain embodiments of any of the described methods, the light chain polypeptide, and first and second heavy chain polypeptides are expressed in a predetermined ratio of about 0.25:1:1. In selected embodiments, the light chain polypeptide, and first and second heavy chain polypeptides are expressed in a predetermined ratio of about 1:2:2. In some embodiments, the light chain polypeptide, and first and second heavy chain polypeptides are expressed in a predetermined ratio of about 1:3:3. In certain other embodiments, the first and second heavy chains are expressed in different relative amounts. For example, in some embodiments, the light chain polypeptide, and first and second heavy chain polypeptides are expressed in a predetermined ratio of about 2:1:3, or about 2:3:1. In one embodiment the ratio of transfection of light chain polypeptide (LC) to first heavy chain polypeptide (HC1) and second heavy chain polypeptide (HC2), i.e., LC:HC1:HC2 is 3:1:1 to determine, in some instances, if HC1 and HC2 are equally expressed. It would be understood that other ratios may be used and are contemplated herein. In a non-limiting example, LCCA dose verification ratios for LC:HC1:HC2 may be (50:75:25, 50:50:50 and 50:25:75) or (50:40:60, 50:50:50 and 50:60:40).

In certain embodiments the co-expression is in a host cell. In some embodiments, the co-expression is in an in vitro non-cell expression system.

In embodiments, the methods provided herein comprise the step of separating expressed polypeptides from the expression medium after expression. In some embodiments, the polypeptides are separated by centrifugation. In some further embodiments, the polypeptides are separated by use of a purification column.

In some embodiments of the methods described herein, the first heavy chain polypeptide comprising a VH and CH1 region further comprises a CH3 region. In some embodiments, the method further comprises co-expression of a second heavy chain polypeptide comprising a CH3 region. In certain embodiments at least one heavy chain polypeptide comprises a CH2 region or fragment thereof.

In certain embodiments, the methods described herein further comprise use of quantitative control standards. In an embodiment, the method comprises expressing said heavy chain polypeptide and one of said first and second light chain polypeptide in at least one host cell or in an in vitro system, in the absence of other light chain polypeptides; isolating heavy chain-paired polypeptide products comprising the heavy chain polypeptide and the light chain polypeptide; and quantitating the amount of said products, wherein said amount serves as a control standard for maximum detectable binding of said heavy chain polypeptide with said light chain polypeptide. In some embodiments, products that comprise a heavy chain polypeptide and a desired light chain polypeptide provide a positive control standard. In embodiments, products that comprise a heavy chain polypeptide and a less desired light chain polypeptide provide a negative control standard.

The methods described herein may also, in some instances, comprise a step of removing any unbound polypeptide from a mixture comprising isolated constructs.

Provided are methods of quantifying selectivity of a heavy chain polypeptide for pairing with at least one light chain polypeptide, wherein at least one light chain polypeptide comprises a detectable moiety. A detectable moiety may be a protein binding site, a ligand binding site, or a tag comprising a further detectable moiety. In certain embodiments, each light chain polypeptide is labeled with a different tag comprising a different detectable moiety. In some embodiments, a heavy chain polypeptide is labeled with a tag. In an embodiment, the tag labeling said heavy chain polypeptide is capable of being captured onto a surface comprising an interactive surface layer, and further detected and quantified by a device. A device may be used to detect and quantify the detectable moiety on at least one of said first and second light chain polypeptides. In some embodiments, a device is capable of high throughput. The detection of a detectable moiety may comprise measurement using any conventional means to detect labels including, but not limited to, ELISA, SPR chips, bimolecular fluorescence complementation readout, Fluorescence-Activated Cell Sorting (FACS), DELFIA®, fluorescence polarization/anisotropy (FP), fluorescent/Foerster resonance energy transfer (FRET, TR-FRET, HTRF), AlphaScreen®, or a combination thereof. In some embodiments, detection of a detectable moiety comprises measurement of fluorescence, quenching, radioactivity or chemiluminescence.

Provided in certain embodiments is a method for determining the selective formation of a Fab-containing construct in the presence of competing heavy or light chain polypeptides or combinations thereof, said method comprising: co-expressing a set of constructs in vitro or in a host cell: a first heavy chain polypeptide comprising a VH and a CH1 region; and a first light chain polypeptide comprising a first VL and first CL region; wherein said first light chain polypeptide selectively associates with said heavy chain polypeptide to form a desired Fab construct; one or more other heavy chain polypeptides, light chain polypeptides or combinations thereof; isolating each Fab construct comprising said first heavy chain polypeptide or said first light chain polypeptide; and detecting the amount of desired Fab construct as compared to other Fab constructs; wherein a greater amount of the desired Fab construct demonstrates a higher selectivity of formation of said Fab construct. In some cases, the first heavy chain polypeptide and light chain polypeptide are labeled with tags comprising different detectable moieties.

Provided is a method for determining the ability of a rationally designed Fab construct to self-associate in the presence of other heavy or light chain polypeptides, comprising the method of quantifying selectivity of a heavy chain polypeptide for pairing with at least one light chain polypeptide described herein, wherein said first heavy chain polypeptide and said first light chain polypeptide associate to form the designed Fab construct.

Provided are methods of quantifying selectivity of a heavy chain polypeptide for pairing with at least one light chain polypeptide wherein said polypeptides are co-expressed in a host cell. In some embodiments, the host cell is a bacterial cell. In an embodiment, the host cell is a yeast cell. In certain embodiments, the host cell is a mammalian cell. In some embodiments, the mammalian cell is at least one of COS, CHO, BHK, HEK-293, NSO, 3T3 cells and derivatives thereof.

Provided are methods described herein wherein at least one heavy chain or light chain polypeptide comprises at least one tag selected from 6×His, FLAG, HA, c-myc, s-FLAG, SBP, V5 and ABD.

Provided is a method of designing a heteromultimer antibody construct comprising: a) co-expressing a set of constructs in vitro or in a host cell: a first heavy chain polypeptide comprising a first immunoglobulin heavy chain region; a first light chain polypeptide comprising a first immunoglobulin light chain region, said first light chain polypeptide capable of associating with said first heavy chain polypeptide to form a first Fab construct; and a second light chain polypeptide comprising a second immunoglobulin light chain region capable of associating with a second heavy chain polypeptide comprising a second immunoglobulin heavy chain region to form a second Fab construct, wherein said first and second heavy chain polypeptides are capable of forming heteromultimer comprising a variant CH3 region; b) detecting the amount of Fab constructs formed comprising said first heavy chain polypeptide and any one of said light chain polypeptides; c) expressing in a host cell: said second heavy chain polypeptide, first light chain polypeptide and second light chain polypeptide; d) detecting the amount of Fab constructs formed comprising said second heavy chain polypeptide and any one of said light chain polypeptides; wherein a greater amount of the first Fab construct in step b) and a greater amount of the second Fab construct in step d) as compared to other Fab constructs, demonstrates that the polypeptides can self-assemble to form the heteromultimer antibody construct.

Provided is a method for high throughput screening of polypeptides for designing a heteromultimer antibody comprising: a) obtaining: a first heavy chain polypeptide comprising a first immunoglobulin heavy chain region; a first light chain polypeptide comprising a first immunoglobulin light chain region, said first light chain polypeptide capable of associating with said first heavy chain polypeptide to form a first Fab construct; a second heavy chain polypeptide comprising a second immunoglobulin heavy chain region, wherein said first and second heavy chain polypeptides are capable of forming heteromultimer comprising a variant CH3 region; and a second light chain polypeptide comprising a second immunoglobulin light chain region capable of associating with said second heavy chain polypeptide to form a second Fab construct; b) contacting in a solution, said first heavy chain polypeptide with said first and second light chain polypeptides; c) detecting in the solution from step b), the amount of Fab constructs formed comprising said first heavy chain polypeptide and any one of said light chain polypeptides; d) contacting in another solution, said second heavy chain polypeptide with said first and second light chain polypeptides; e) detecting in the solution from step d), the amount of Fab constructs formed comprising said second heavy chain polypeptide and any one of said light chain polypeptides; wherein a greater amount of the first Fab construct in step c) and a greater amount of the second Fab construct in step e) as compared to other Fab constructs, demonstrates that the polypeptides can self-assemble to form a heteromultimer antibody construct.

In certain embodiments, each light chain polypeptide and each heavy chain polypeptide is labeled with a different tag comprising a different detectable moiety. In some embodiments, each heavy chain tag is capable of being captured by a device comprising an interactive surface layer. In some embodiments, the device is capable of quantitatively recognizing the tag on each light chain polypeptide. In certain embodiments, the device is capable of high throughput. In an embodiment, the detectable moiety is quantifiably detected by measurement by ELISA, SPR chips, bimolecular fluorescence complementation readout, Fluorescence-Activated Cell Sorting (FACS), DELFIA®, fluorescence polarization/anisotropy (FP), fluorescent/Foerster resonance energy transfer (FRET, TR-FRET, HTRF), AlphaScreen®, or a combination thereof. A detectable moiety may be quantifiably detected by measurement of fluorescence, quenching, radioactivity or chemiluminescence.

Provided is a high-throughput method of determining selectivity of a heavy chain polypeptide for pairing with at least one light chain polypeptide comprising the steps of: obtaining: a heavy chain polypeptide comprising an immunoglobulin heavy chain region; a first light chain polypeptide comprising a first immunoglobulin light chain region; and at least one second light chain polypeptide comprising a second immunoglobulin light chain region; contacting in a solution said heavy chain polypeptide and said light chain polypeptides in a pre-determined ratio such that the total amount of the heavy chain polypeptide is limiting; isolating heavy chain-paired polypeptide products comprising the heavy chain polypeptide paired with said first or second light chain polypeptide; and quantitating the amount of heavy chain polypeptide paired with said first light chain polypeptide, and the amount of heavy chain polypeptide paired with said second light chain polypeptide; wherein a greater amount of the heavy chain polypeptide paired with one of said first or second light chain polypeptide as compared to the other light chain polypeptide indicates selectivity of the heavy chain polypeptide for pairing with said first or second light chain polypeptide.

Provided is a system for high-throughput screening of selective pairing of a heavy chain polypeptide with at least one light chain polypeptide comprising: one or more host cells or an in vitro mechanism to express: a heavy chain polypeptide comprising an immunoglobulin heavy chain (HC) region and a tag which is capable of being captured by a device comprising an interactive surface layer; a first light chain polypeptide (L1) comprising a first immunoglobulin light chain region; and at least one second light chain (L2) polypeptide comprising a second immunoglobulin light chain region; wherein said heavy chain polypeptide and said light chain polypeptides are expressed in a pre-determined ratio such that HC<(L1+L2); and wherein said first and second light chain polypeptide are tagged with a detectable moiety; and a detection device comprising an interactive surface layer capable of capturing said heavy chain polypeptide, wherein said device is further capable of detecting of the detectable moiety on each said light chain polypeptide; wherein constructs comprising the heavy chain polypeptide and said first or second light chain polypeptide are expressed by said one or more host cells, and contacted with said detection device, and wherein said detection device is useful to detect the amount of a first construct comprising the heavy chain polypeptide and first light chain polypeptide, and the amount of second construct comprising the heavy chain polypeptide and second light chain polypeptide, such that a greater amount of the first construct as compared to the second construct demonstrates a higher selectivity of the heavy chain polypeptide for pairing with the first light chain polypeptide, as compared to the second light chain polypeptide.

In some embodiments, the system further comprises a mechanism for isolating said constructs from said one or more host cells prior to contacting with said detection device. In an embodiment, the predetermined ratio of said heavy chain polypeptide, and first and second light chain polypeptides is about 0.25:1:1. In an embodiment, the predetermined ratio of said heavy chain polypeptide, and first and second light chain polypeptides is about 0.5:1:1. In some embodiments, the predetermined ratio of said heavy chain polypeptide, and first and second light chain polypeptides is about 1:2:2. In certain embodiments, the predetermined ratio of said heavy chain polypeptide, and first and second light chain polypeptides is about 1:3:3. In certain other embodiments, the first and second light chains are expressed in different relative amounts. For example, in some embodiments, the heavy chain polypeptide, and first and second light chain polypeptides are expressed in a predetermined ratio of about 2:1:3, or about 2:3:1.

Provided is a kit for high throughput design of a heteromultimer antibody, comprising a system described herein, and instructions for use. In some embodiments, a kit further comprises one or more vials, tubes, containers, reagents and/or buffers. In certain embodiments, a kit further comprises means to purify the heavy and light chain polypeptides. Means for isolating or purifying polypeptides are known in the art and described below.

In one aspect of the invention there is provided a method of determining the ability of at least one modified heavy chain to selectively pair with a specific modified light chain in a co-expression assay, said method comprising: a. co-expressing at least one modified heavy chain and two different modified light chains in a cell, in ratios such that the modified heavy-chain is the limiting pairing reactant, wherein co-expressed proteins are secreted from the cell; b. optionally separating the co-expressed secreted proteins from the cell; c. separating the light chain polypeptides bound to modified heavy chain from the rest of the secreted proteins to produce an isolated heavy chain paired fraction; d. detecting the amount of each different modified light chain in the isolated heavy chain fraction; and e. analyzing the relative amount of each different modified light chain in the isolated heavy chain fraction to determine the ability of the at least one heavy chain to selectively pair with one of the light chains.

BRIEF DESCRIPTION OF THE FIGURES

FIG. 3A illustrates a SPR Sandwich-Based Assay and FIG. 3B illustrates an Anti-His Tag surface.

FIG. 8B). Next, LCCA designs (e.g., $HC_1$, $LC1_1$, and $LC2_1$ . . . $HC_N$, $LC1_N$, and $LC2_N$) are transiently expressed in mammalian cells (e.g., CHO; see step 3; FIG. 8C). Seven days post-transfection, CHO cell supernatants are harvested and HC-LC1:HC-LC2 populations are quantified for each LCCA design using an SPR readout (step 4; FIG. 8D). Working designs are than ranked based on set criteria (e.g., HC-LC1:HC-LC2>=75:25); successful designs than become part of the 'Working LCCA library'. When dealing with large data sets, an optional data-mining step (#5; FIG. 8E) is available. During this step, a 'global analysis of HC-LC pairing results' is carried out. This step can be quite informative, since it potentially allows non-trivial and non-obvious patterns/trends in your data to be recognized. Finally, a working LCCA library is compiled (FIG. 8F).

DETAILED DESCRIPTION

Figure 1:
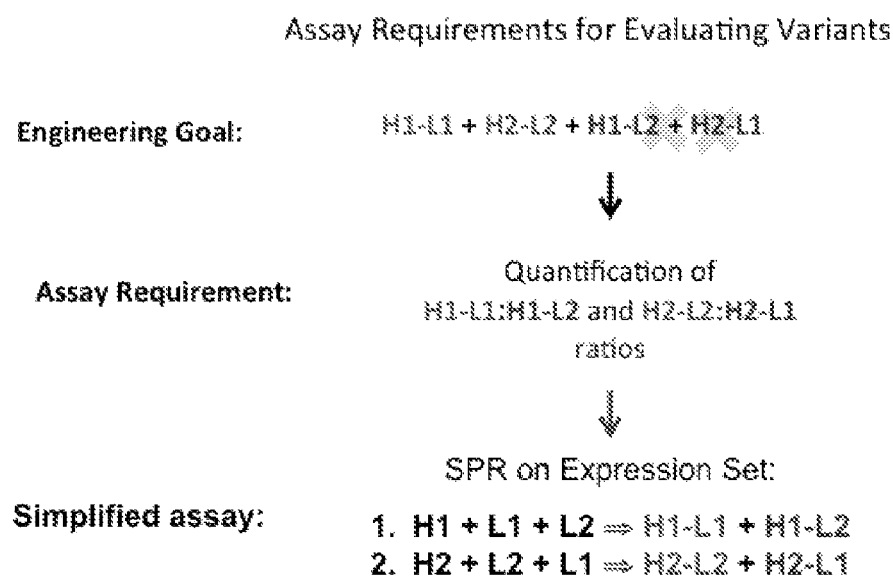
FIG. 1 provides a flow chart for assay requirements for evaluating variants.

Provided herein is a quantitative method for determining the ability of an immunoglobulin (IgG) heavy chain or an immunoglobulin light chain to selectively pair with a particular IgG light chain or IgG heavy chain, respectively. In one embodiment, the method is used to determine if one particular IgG heavy chain selectively pairs with either one of two unique IgG light chains when the heavy chain and unique light chains are co-expressed. The assay is flexible in that the IgG heavy and light chains that are co-expressed can be in a "Fab" format, or in a format where the heavy chain also includes an Fc region.

The method can be performed as a high-throughput assay and is sensitive in that it measures the effects of small variations in the amino acid sequence of the IgG heavy and light chains. The method is generic in that it is capable of quantifying most heavy chain-light chain pairings without significant modification.

In one embodiment, the method is used to screen libraries of rationally designed IgG polypeptides that have been modified to drive specific heavy chain-light chain pairing. In addition, when the method is carried out using IgG polypeptides in a non-wild type format, for example in a Fab format, the quantitation of selective pairing is predictive of the selective pairing of the IgG polypeptides in a wild-type format. As such, the method can be used to identify Fab modules that are useful in the preparation of bi-specific antibodies.

In an additional embodiment, a graphical method of analysis of a large set of measurements is provided herein by which combinations of IgG heavy chains and IgG light chains that are especially conducive to selective pairing are discovered. The analysis method thus enables effective processing of data obtained from a high-throughput generation of assay data.

In accordance with the present application, there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984), each of which is specifically incorporated herein by reference in its entirety.

Provided are high throughput screening methods and devices that are capable of performing repeated, accurate assay screens, and operating at very small volumes to design and identify FAB modules useful for constructing antibody constructs. In some embodiments, the constructed antibody constructs are biparatopic. Some antibody constructs are bispecific.

Antibody Terminology

As used herein, the term "antibody" refers to an immunoglobulin (Ig) whether natural or partly or wholly synthetically produced. The term also covers any polypeptide or protein having a binding domain which is, or is homologous to, an antigen-binding domain. The term further includes "antigen-binding fragments" and other interchangeable terms for similar binding fragments such as described below. Complementarity determining region (CDR) grafted antibodies and other humanized antibodies (including CDR modifications and framework region modifications) are also contemplated by this term.

Native antibodies and native immunoglobulins are usually heterotetrameric glycoproteins of about 150,000 Daltons, composed of two identical light (L) chains and two identical heavy (H) chains. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ("VH" or "$V_H$") followed by a number of constant domains ("CH" or "$C_H$"). Each light chain has a variable domain at one end ("VL" or "$V_L$") and a constant domain ("CL" or "$C_L$") at its other end; the constant domain of the light chain is aligned with the first constant domain of the heavy chain, and the light-chain variable domain is aligned with the variable domain of the heavy chain. Particular amino acid residues are known to form an interface between the light- and heavy-chain variable domains.

The terms "synthetic polynucleotide," "synthetic gene" or "synthetic polypeptide," as used herein, refer to the corresponding polynucleotide sequence or portion thereof, or amino acid sequence or portion thereof, is derived, from a sequence that has been designed, or synthesized de novo, or modified, compared to an equivalent naturally-occurring sequence. Synthetic polynucleotides (antibodies or antigen binding fragments) or synthetic genes can be prepared by methods known in the art, including but not limited to, the chemical synthesis of nucleic acid or amino acid sequences. Synthetic genes are typically different from naturally-occurring genes, either at the amino acid, or polynucleotide level, (or both) and are typically located within the context of synthetic expression control sequences. For example, synthetic gene sequences can include amino acid, or polynucleotide, sequences that have been changed, for example, by the replacement, deletion, or addition, of one or more, amino acids, or nucleotides, thereby providing an antibody amino acid sequence, or a polynucleotide coding sequence that is different from the source sequence. Synthetic gene polynucleotide sequences, may not necessarily encode proteins with different amino acids, compared to the natural gene; for example, they can also encompass synthetic polynucleotide sequences that incorporate different codons but which encode the same amino acid (i.e., the nucleotide changes represent silent mutations at the amino acid level).

With respect to antibodies, the term "variable domain" refers to the variable domains of antibodies that are used in the binding and specificity of each particular antibody for its particular antigen. However, the variability is not evenly distributed throughout the variable domains of antibodies. Rather, it is concentrated in three segments called hypervariable regions (also known as CDRs) in both the light chain and the heavy chain variable domains. More highly conserved portions of variable domains are called the "framework regions" or "FRs." The variable domains of unmodified heavy and light chains each contain four FRs (FR1, FR2, FR3 and FR4), largely adopting a β-sheet configuration interspersed with three CDRs which form loops connecting and, in some cases, part of the β-sheet structure. The CDRs in each chain are held together in close proximity by the FRs and, with the CDRs from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669).

The terms "hypervariable region" and "CDR" when used herein, refer to the amino acid residues of an antibody which are responsible for antigen-binding. The CDRs comprise amino acid residues from three sequence regions which bind in a complementary manner to an antigen and are known as CDR1, CDR2, and CDR3 for each of the VH and VL chains. In the light chain variable domain, the CDRs typically correspond to approximately residues 24-34 (CDRL1), 50-56 (CDRL2) and 89-97 (CDRL3), and in the heavy chain variable domain the CDRs typically correspond to approximately residues 31-35 (CDRH1), 50-65 (CDRH2) and 95-102 (CDRH3) according to Kabat et al., Sequences of Proteins of Immunological Interest, 5th Ed. Public Health Service, National Institutes of Health, Bethesda, Md. (1991)). It is understood that the CDRs of different antibodies may contain insertions, thus the amino acid numbering may differ. The Kabat numbering system accounts for such insertions with a numbering scheme that utilizes letters attached to specific residues (e.g., 27A, 27B, 27C, 27D, 27E, and 27F of CDRL1 in the light chain) to reflect any insertions in the numberings between different antibodies. Alternatively, in the light chain variable domain, the CDRs typically correspond to approximately residues 26-32 (CDRL1), 50-52 (CDRL2) and 91-96 (CDRL3), and in the heavy chain variable domain, the CDRs typically correspond to approximately residues 26-32 (CDRH1), 53-55 (CDRH2) and 96-101 (CDRH3) according to Chothia and Lesk, J. Mol. Biol., 196: 901-917 (1987)).

As used herein, "framework region" or "FR" refers to framework amino acid residues that form a part of the antigen binding pocket or groove. In some embodiments, the framework residues form a loop that is a part of the antigen binding pocket or groove and the amino acids residues in the loop may or may not contact the antigen. Framework regions generally comprise the regions between the CDRs. In the light chain variable domain, the FRs typically correspond to approximately residues 0-23 (FRL1), 35-49 (FRL2), 57-88 (FRL3), and 98-109 and in the heavy chain variable domain the FRs typically correspond to approximately residues 0-30 (FRH1), 36-49 (FRH2), 66-94 (FRH3), and 103-133 according to Kabat et al., Sequences of Proteins of Immunological Interest, 5th Ed. Public Health Service, National Institutes of Health, Bethesda, Md. (1991)). As discussed above with the Kabat numbering for the light chain, the heavy chain too accounts for insertions in a similar manner (e.g., 35A, 35B of CDRH1 in the heavy chain). Alternatively, in the light chain variable domain, the FRs typically correspond to approximately residues 0-25 (FRL1), 33-49 (FRL2) 53-90 (FRL3), and 97-109 (FRL4), and in the heavy chain variable domain, the FRs typically correspond to approximately residues 0-25 (FRH1), 33-52 (FRH2), 56-95 (FRH3), and 102-113 (FRH4) according to Chothia and Lesk, *J. Mol. Biol.*, 196: 901-917 (1987)).

The loop amino acids of a FR can be assessed and determined by inspection of the three-dimensional structure of an antibody heavy chain and/or antibody light chain. The three-dimensional structure can be analyzed for solvent accessible amino acid positions as such positions are likely to form a loop and/or provide antigen contact in an antibody variable domain. Some of the solvent accessible positions can tolerate amino acid sequence diversity and others (e.g., structural positions) are, generally, less diversified. The three dimensional structure of the antibody variable domain can be derived from a crystal structure or protein modeling.

The contant domains of the Fc domains of antibodies are not involved directly in binding an antibody to an antigen but, rather, exhibit various effector functions, such as participation of the antibody in antibody-dependent cellular toxicity via interactions with, for example, Fc receptors (FcR). Fc domains can also increase bioavailability of an antibody in circulation following administration to a subject.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, and $IgA_2$. The heavy-chain constant domains (Fc) that correspond to the different classes of immunoglobulins are called $\alpha$, $\delta$, $\epsilon$, $\gamma$, and $\mu$, respectively. The subunit structures and three-dimensional configurations of different classes of immunoglobulins are well known. In one embodiment, an antibody, or antigen-binding fragment described herein is an IgG isotype such as, for example, subtype $IgG_1$ or $IgG_4$. Heavy chains are referred to herein interchangeably as "IgG heavy chains," "IgG heavy chain polypeptides," or "heavy chain polypeptides." Heavy chains are also abbreviated herein as "HC" or "H," for example HC1 and HC2, or H1 and H2.

The "light chains" of antibodies (immunoglobulins) from any vertebrate species can be assigned to one of two clearly distinct types, called kappa or ("κ") and lambda or ("λ"), based on the amino acid sequences of their constant domains. Light chains are referred to herein interchangeable as "IgG light chains," "IgG light chain polypeptides," or "light chain polypeptides." Light chains are also abbreviated herein as "LC" or "L," for example, LC1 and LC2, or L1 and L2.

The terms "antigen-binding portion of an antibody," "antigen-binding fragment," "antigen-binding domain," "antibody fragment" or a "functional fragment of an antibody" are used interchangeably herein to refer to one or more fragments of an antibody that retain the ability to specifically bind to an antigen. Non-limiting examples of antibody fragments included within such terms include, but are not limited to, (i) a Fab fragment, a monovalent fragment consisting of the VL, VH, CL and CH1 domains; (ii) a $F(ab')_2$ fragment, a bivalent fragment containing two Fab fragments linked by a disulfide bridge at the hinge region; (iii) a Fd fragment consisting of the VH and CH1 domains; (iv) a Fv fragment containing the VL and VH domains of a single arm of an antibody, (v) a dAb fragment (Ward et al., (1989) Nature 341:544 546), containing a VH domain; and (vi) an isolated CDR. Additionally included in this definition are "one-half" antibodies comprising a single heavy chain and a single light chain. Other forms of single chain antibodies, such as diabodies are also encompassed herein.

"$F(ab')_2$" and "Fab'" moieties can be produced by treating an Ig with a protease such as pepsin and papain, and include antibody fragments generated by digesting immunoglobulin near the disulfide bonds existing between the hinge regions in each of the two heavy chains. For example, papain cleaves IgG upstream of the disulfide bonds existing between the hinge regions in each of the two heavy chains to generate two homologous antibody fragments in which an light chain composed of VL and CL (light chain constant region), and a heavy chain fragment composed of VH and CHγ1 (γ1) region in the constant region of the heavy chain) are connected at their C terminal regions through a disulfide bond. Each of these two homologous antibody fragments is called Fab'. Pepsin also cleaves IgG downstream of the disulfide bonds existing between the hinge regions in each of the two heavy chains to generate an antibody fragment slightly larger than the fragment in which the two above-mentioned Fab' are connected at the hinge region. This antibody fragment is called $F(ab')_2$.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Fv" refers to an antibody fragment which contains a complete antigen-recognition and antigen-binding site. This region consists of a dimer of one heavy chain and one light chain variable domain in tight, non-covalent or covalent association (disulfide linked Fv's have been described in the art, Reiter et al. (1996) Nature Biotechnology 14:1239-1245). It is in this configuration that the three CDRs of each variable domain interact to define an antigen-binding site on the surface of the VH-VL dimer. Collectively, a combination of one or more of the CDRs from each of the VH and VL chains confer antigen-binding specificity to the antibody. For example, it would be understood that, for example, the CDRH3 and CDRL3 could be sufficient to confer antigen-binding specificity to an antibody when transferred to VH and VL chains of a recipient antibody or antigen-binding fragment thereof and this combination of CDRs can be tested for binding, affinity, etc. using any of the techniques described herein. Even a single variable domain (or half of an Fv comprising only three CDRs specific for an antigen) has the ability to recognize and bind antigen, although likely at a lower affinity than when combined with a second variable domain. Furthermore, although the two domains of a Fv fragment (VL and VH), are coded for by separate genes, they can be joined using recombinant methods by a synthetic linker that enables them to be made as a single protein chain in which the VL and VH regions pair to form monovalent molecules (known as single chain Fv (scFv); Bird et al. (1988) Science 242:423-426; Huston et al. (1988) Proc. Natl. Acad. Sci. USA 85:5879-5883; and Osbourn et al. (1998) Nat. Biotechnol. 16:778). Such scFvs are also intended to be encompassed within the term "antigen-binding portion" of an antibody. Any VH and VL sequences of specific scFv can be linked to an Fc region cDNA or genomic sequences, in order to generate expression vectors encoding complete Ig (e.g., IgG) molecules or other isotypes. VH and VL can also be used in the generation of Fab, Fv or other fragments of Igs using either protein chemistry or recombinant DNA technology.

"Single-chain Fv" or "scFv" antibody fragments comprise the VH and VL domains of an antibody, wherein these domains are present in a single polypeptide chain. In some embodiments, the Fv polypeptide further comprises a polypeptide linker between the VH and VL domains which enables the scFv to form the desired structure for antigen binding. For a review of sFvs see, e.g., Pluckthun in The Pharmacology of Monoclonal Antibodies, Vol. 113, Rosenburg and Moore eds. Springer-Verlag, New York, pp. 269-315 (1994).

The term "AVIMER™" refers to a class of therapeutic proteins of human origin, which are unrelated to antibodies and antibody fragments, and are composed of several modular and reusable binding domains, referred to as A-domains (also referred to as class A module, complement type repeat, or LDL-receptor class A domain). They were developed from human extracellular receptor domains by in vitro exon shuffling and phage display (Silverman et al., 2005, *Nat. Biotechnol.* 23:1493-1494; Silverman et al., 2006, *Nat. Biotechnol.* 24:220). The resulting proteins can contain multiple independent binding domains that can exhibit improved affinity (in some cases, sub-nanomolar) and specificity compared with single-epitope binding proteins. See, for example, U.S. Patent Application Publ. Nos. 2005/ 0221384, 2005/0164301, 2005/0053973 and 2005/0089932, 2005/0048512, and 2004/0175756, each of which is hereby incorporated by reference herein in its entirety.

Each of the known 217 human A-domains comprises ~35 amino acids (~4 kDa); and these domains are separated by linkers that average five amino acids in length. Native A-domains fold quickly and efficiently to a uniform, stable structure mediated primarily by calcium binding and disulfide formation. A conserved scaffold motif of only 12 amino acids is required for this common structure. The end result is a single protein chain containing multiple domains, each of which represents a separate function. Each domain of the proteins binds independently and the energetic contributions of each domain are additive. These proteins were called "AVIMERs™" from avidity multimers.

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444 6448 (1993).

Antigen-binding polypeptides also include heavy chain dimers such as, for example, antibodies from camelids and sharks. Camelid and shark antibodies comprise a homodimeric pair of two chains of V-like and C-like domains (neither has a light chain). Since the VH region of a heavy chain dimer IgG in a camelid does not have to make hydrophobic interactions with a light chain, the region in the heavy chain that normally contacts a light chain is changed to hydrophilic amino acid residues in a camelid. VH domains of heavy-chain dimer IgGs are called VHH domains. Shark Ig-NARs comprise a homodimer of one variable domain (termed a V-NAR domain) and five C-like constant domains (C-NAR domains). In camelids, the diversity of antibody repertoire is determined by the CDRs 1, 2, and 3 in the VH or VHH regions. The CDR3 in the camel VHH region is characterized by its relatively long length, averaging 16 amino acids (Muyldermans et al., 1994, *Protein Engineering* 7(9): 1129). This is in contrast to CDR3 regions of antibodies of many other species. For example, the CDR3 of mouse VH has an average of 9 amino acids. Libraries of camelid-derived antibody variable regions, which maintain the in vivo diversity of the variable regions of a camelid, can be made by, for example, the methods disclosed in U.S. Patent Application Ser. No. 20050037421.

"Humanized" forms of non-human (e.g., murine) antibodies include chimeric antibodies which contain minimal sequence derived from a non-human Ig. For the most part, humanized antibodies are human Igs (recipient antibody) in which one or more of the CDRs of the recipient are replaced by CDRs from a non-human species antibody (donor antibody) such as mouse, rat, rabbit or non-human primate having the desired specificity, affinity and binding function. In some instances, one or more FR amino acid residues of the human Ig are replaced by corresponding non-human amino acid residues. Furthermore, humanized antibodies can contain residues which are not found in the recipient antibody or in the donor antibody. These modifications can be made to refine antibody performance, if needed. A humanized antibody can comprise substantially all of at least one and, in some cases two, variable domains, in which all or substantially all of the hypervariable regions correspond to those of a non-human immunoglobulin and all, or substantially all, of the FRs are those of a human immunoglobulin sequence. The humanized antibody optionally can also include at least a portion of an immunoglobulin constant region (Fc), typically that of a human immunoglobulin. For details, see Jones et al., *Nature* 321: 522-525 (1986); Reichmann et al., *Nature* 332: 323-329 (1988); and Presta, *Curr. Op. Struct. Biol.* 2: 593-596 (1992).

A humanized antibody also includes antibodies in which part, or all of the CDRs of the heavy and light chain are derived from a non-human monoclonal antibody, substantially all the remaining portions of the variable regions are derived from human variable region (both heavy and light chain), and the constant regions are derived from a human constant region. In one embodiment, the CDR1, CDR2 and CDR3 regions of the heavy and light chains are derived from a non-human antibody. In yet another embodiment, at least one CDR (e.g., a CDR3) of the heavy and light chains is derived from a non-human antibody. Various combinations of CDR1, CDR2, and CDR3 can be derived from a non-human antibody and are contemplated herein. In one non-limiting example, one or more of the CDR1, CDR2 and CDR3 regions of each of the heavy and light chains are derived from the sequences provided herein.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations, which can include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, monoclonal antibodies can be made by the hybridoma method first described by Kohler et al., *Nature* 256:495 (1975), or can be made by recombinant DNA methods (see, e.g., U.S. Pat. No. 4,816,567). In certain embodiments, the monoclonal antibodies can be isolated from phage antibody libraries using the techniques described in Clackson et al., *Nature* 352:624-628 (1991) and Marks et al., *J. Mol. Biol.* 222:581-597 (1991), for example.

Antibodies can be isolated and purified from the culture supernatant or ascites mentioned above by saturated ammonium sulfate precipitation, euglobulin precipitation method, caproic acid method, caprylic acid method, ion exchange chromatography (DEAE or DE52), or affinity chromatography using anti-Ig column or a protein A, G or L column such as described in more detail below.

Exemplary antibodies for use in the compositions and methods described herein are intact immunoglobulin molecules, such as, for example, a humanized antibody or those portions of a humanized Ig molecule that contain the antigen-binding site (i.e., paratope) or a single heavy chain and a single light chain, including those portions known in the art as Fab, Fab', F(ab)', F(ab')$_2$, Fd, scFv, a variable heavy domain, a variable light domain, a variable NAR domain, bi-specific scFv, a bi-specific Fab2, a tri-specific Fab$_3$ and a single chain binding polypeptides and others also referred to as antigen-binding fragments. When constructing an immunoglobulin molecule or fragments thereof, variable regions or portions thereof may be fused to, connected to, or otherwise joined to one or more constant regions or portions thereof to produce any of the antibodies or fragments thereof described herein. This may be accomplished in a variety of ways known in the art, including but not limited to, molecular cloning techniques or direct synthesis of the nucleic acids encoding the molecules. Exemplary non-limiting methods of constructing these molecules can also be found in the examples described herein.

Methods for making bispecific or other multispecific antibodies are known in the art and include chemical cross-linking, use of leucine zippers (Kostelny et al., *J. Immunol.* 148:1547-1553, 1992); diabody technology (Hollinger et al., *Proc. Natl. Acad. Sci. USA* 90:6444-48, 1993); scFv dimers [Gruber et al., *J. Immunol.* 152: 5368, 1994], linear antibodies (Zapata et al., *Protein Eng.* 8:1057-62, 1995); and chelating recombinant antibodies (Neri et al., *J Mol Biol.* 246:367-73, 1995).

"Linear antibodies" comprise a pair of tandem Fd segments (VH-CH1-VH-CH1) which form a pair of antigen binding regions. Linear antibodies can be bispecific or monospecific (Zapata et al. *Protein Eng.* 8:1057-62 (1995)).

Additionally, the antibodies disclosed herein can also be constructed to fold into multivalent forms, which may improve binding affinity, specificity and/or increased half-life in blood. Multivalent forms of antibodies can be prepared by techniques known in the art.

Bispecific or multispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques. Another method is designed to make tetramers by adding a streptavidin-coding sequence at the C-terminus of the scFv. Streptavidin is composed of four subunits, so when the scFv-streptavidin is folded, four subunits associate to form a tetramer (Kipriyanov et al., *Hum Antibodies Hybridomas,* 6(3): 93-101 (1995), the disclosure of which is incorporated herein by reference in its entirety).

As used herein, a "maxibody" refers to a bivalent scFv covalently attached to the Fc region of an immunoglobulin, see, for example, Fredericks et al., *Protein Engineering, Design & Selection,* 17:95-106 (2004) and Powers et al., *Journal of Immunological Methods,* 251:123-135 (2001).

As used herein, an "intrabody" refers to a single chain antibody which demonstrates intracellular expression and can manipulate intracellular protein function (Biocca, et al., *EMBO J.* 9:101-108, 1990; Colby et al., *Proc Natl Acad Sci USA.* 101:17616-21, 2004). Intrabodies, which comprise cell signal sequences which retain the antibody construct in intracellular regions, may be produced as described in Mhashilkar et al., (*EMBO J* 14:1542-51, 1995) and Wheeler et al. (*FASEB J.* 17:1733-5. 2003). Transbodies are cell-permeable antibodies in which a protein transduction domains (PTD) is fused with single chain variable fragment (scFv) antibodies Heng et al., (*Med Hypotheses.* 64:1105-8, 2005).

Additionally contemplated herein are antibodies that are SMIPs or binding domain immunoglobulin fusion proteins specific for target protein. These constructs are single-chain polypeptides comprising antigen binding domains fused to immunoglobulin domains necessary to carry out antibody effector functions. See, e.g., WO03/041600, U.S. Patent publication 20030133939 and US Patent Publication 20030118592, which are hereby incorporated by reference.

Humanization of antibodies and antigen-binding fragments thereof, can be accomplished via a variety of methods known in the art and described herein. Similarly, production of humanized antibodies can also be accomplished via methods known in the art and described herein.

In one exemplary embodiment, the application contemplates a single chain binding polypeptide having a heavy chain variable region, and/or a light chain variable region which binds an epitope described herein and has, optionally, an immunoglobulin Fc region. Such a molecule is a single chain variable fragment (scFv) optionally having effector function or increased half-life through the presence of the immunoglobulin Fc region. Methods of preparing single chain binding polypeptides are known in the art (e.g., U.S. Patent Application No. 2005/0238646).

Binding affinity and/or avidity of antibodies or antigen-binding fragments thereof may be improved by modifying framework regions. Methods for modifications of framework regions are known in the art and are contemplated herein. Selection of one or more relevant framework amino acid positions for modification depends on a variety of criteria. One criterion for selecting relevant framework amino acids to change can be the relative differences in amino acid framework residues between the donor and acceptor molecules. Selection of relevant framework positions to alter using this approach has the advantage of avoiding any subjective bias in residue determination or any bias in CDR binding affinity contribution by the residue.

As used herein, "immunoreactive" refers to antibodies or antigen-binding fragments thereof that are specific to a sequence of amino acid residues ("binding site" or "epitope"). The term "binding" refers to a direct association between two molecules, due to, for example, covalent, electrostatic, hydrophobic, and ionic and/or hydrogen-bond interactions under physiological conditions, and including interactions such as salt bridges and water bridges and any other conventional binding means. The term "preferentially binds" means that the binding agent binds to the binding site with greater affinity than it binds unrelated amino acid sequences. Preferably such affinity is at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the binding agent for unrelated amino acid sequences. The terms "immunoreactive" and "preferentially binds" are used interchangeably herein.

As used herein, the term "affinity" refers to the equilibrium constant for the reversible binding of two agents and is expressed as Kd. In one embodiment, the antibodies, or antigen-binding fragments thereof exhibit desirable characteristics such as binding affinity as measured by $K_D$ (equilibrium dissociation constant) for a target antigen in the range of $1\times10^{-6}$ M or less, or ranging down to $10^{-16}$ M or lower, (e.g., about $10^{-7}$, $10^{-8}$, $10^{-9}$, $10^{-10}$, $10^{-11}$, $10^{-12}$, $10^{-13}$, $10^{-14}$, $10^{-15}$, $10^{-16}$ M or less). The equilibrium dissociation constant can be determined in solution equilibrium assay using BIAcore and/or KinExA. As used herein, the term "avidity" refers to the resistance of a complex of two or more agents to dissociation after dilution. Apparent affinities can be determined by methods such as an enzyme linked immunosorbent assay (ELISA) or any other technique familiar to one of skill in the art. Avidities can be determined by methods such as a Scatchard analysis or any other technique familiar to one of skill in the art.

When increased affinity of an antibody is desired, residues within the CDRs of a converted antibody may be additionally substituted with other amino acids using conventionally known methods. Typically, no more than four amino acid residues in a CDR are changed, and most typically no more than two residues in the CDR will be changed, except for heavy chain CDR2, where as many as ten (10) residues may be changed. Changes in affinity can be measured by conventional methods such as those described herein (e.g., Biacore). Activity of modified antibodies may be determined using conventional assays based upon the specific target antigen.

"Epitope" refers to that portion of an antigen or other macromolecule capable of forming a binding interaction with the variable region binding pocket of an antibody. Such binding interactions can be manifested as an intermolecular contact with one or more amino acid residues of one or more CDRs. Antigen binding can involve, for example, a CDR3 or a CDR3 pair or, in some cases, interactions of up to all six CDRs of the VH and VL chains. An epitope can be a linear peptide sequence (i.e., "continuous") or can be composed of noncontiguous amino acid sequences (i.e., "conformational" or "discontinuous"). An antibody can recognize one or more amino acid sequences; therefore an epitope can define more than one distinct amino acid sequence. Epitopes recognized by antibodies can be determined by peptide mapping and sequence analysis techniques well known to one of skill in the art. Binding interactions are manifested as intermolecular contacts with one or more amino acid residues of a CDR.

The term "specific" refers to a situation in which an antibody will not show any significant binding to molecules other than the antigen containing the epitope recognized by the antibody. The term is also applicable where for example, an antigen binding domain is specific for a particular epitope which is carried by a number of antigens, in which case the antibody or antigen-binding fragment thereof carrying the antigen binding domain will be able to bind to the various antigens carrying the epitope. The terms "preferentially binds" or "specifically binds" mean that the antibodies or fragments thereof bind to an epitope with greater affinity than it binds unrelated amino acid sequences, and, if cross-reactive to other polypeptides containing the epitope, are not toxic at the levels at which they are formulated for administration to human use. In one aspect, such affinity is at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the antibody or fragment thereof for unrelated amino acid sequences. The terms "immunoreactive," "binds," "preferentially binds" and "specifically binds" are used interchangeably herein. The term "binding" refers to a direct association between two molecules, due to, for example, covalent, electrostatic, hydrophobic, and ionic and/or hydrogen-bond interactions under physiological conditions, and includes interactions such as salt bridges and water bridges, as well as any other conventional means of binding.

The term "selectivity of a heavy chain polypeptide for a light chain polypeptide" as used herein, refers to the preferential pairing of a heavy chain polypeptide with one of two light chain polypeptides when the heavy chain polypeptide and two light chain polypeptides are co-expressed and the heavy chain is limiting. In the context of a method described herein, selectivity of a heavy chain polypeptide for one light chain polypeptide over the other is demonstrated when the resulting amount of heavy chain polypeptide paired with that light chain polypeptide is greater than the resulting amount of heavy chain polypeptide paired with the other light chain polypeptide when the heavy chain polypeptide and the two light chain polypeptides are co-expressed. In one instance, the light chains are equally expressed.

Similarly, the term "selectivity of a light chain polypeptide for a heavy chain polypeptide" as used herein, refers to the preferential pairing of a light chain polypeptide with one of two heavy chain polypeptides when the light chain polypeptide and two heavy chain polypeptides are co-expressed where the light chain is limiting. In the context of a method described herein, selectivity of a light chain polypeptide for one heavy chain polypeptide over the other is demonstrated when the resulting amount of light chain polypeptide paired with that heavy chain polypeptide is greater than the resulting amount of light chain polypeptide paired with the other heavy chain polypeptide when the light chain polypeptide and the two heavy chain polypeptides are co-expressed. In one insance, the heavy chains are equally expressed. Antibodies may be screened for binding affinity by methods known in the art including, but not limited to, gel-shift assays, Western blots, radiolabeled competition assay, co-fractionation by chromatography, co-precipitation, cross linking, ELISA, and the like, which are described in, for example, Current Protocols in Molecular Biology (1999) John Wiley & Sons, NY, which is incorporated herein by reference in its entirety.

Antibodies which bind to the desired epitope on the target antigen may be screened in a routine cross-blocking assay such as described in Antibodies, A Laboratory Manual, Cold Spring Harbor Laboratory, Ed Harlow and David Lane (1988), can be performed. Routine competitive binding assays may also be used, in which an unknown antibody is characterized by its ability to inhibit binding of target to a target-specific antibody of the invention. Intact antigen, fragments thereof such as the extracellular domain, or linear epitopes can be used. Epitope mapping is described in Champe et al., *J. Biol. Chem.* 270: 1388-1394 (1995).

An antibody may be, for example, a monoclonal antibody, a chimeric antibody, a human antibody, or a humanized antibody.

In one aspect, provided herein is an antibody, or antigen-binding fragment thereof, comprises a heavy chain variable region framework region; and a light chain variable region framework region. An antibody, or antigen-binding fragment thereof, may further comprise one or more of a CH2, a CH2 and/or a CH3 region. In one embodiment, a heavy chain polypeptide comprises a VH region and a CH1 region; optionally, a heavy chain polypeptide may further comprise a CH2 region. Optionally, a a heavy chain polypeptide may further comprise a CH2 region and a CH3 region. In one embodiment, a light chain polypeptide comprising a VL region and CL region.

An antigen-binding fragment may be, for example, a Fab fragment, a Fab' fragment, a F(ab')$_2$ fragment, an Fv fragment, an scFv fragment, a single chain binding polypeptide, a Fd fragment, a variable heavy chain, a variable light chain or a dAb fragment. An antigen-binding fragment may be, for example, an AVIMER, a diabody, or a heavy chain dimer. A heavy chain dimer may be, for example, a camelid or a shark heavy chain construct.

Also provided herein is an isolated nucleic acid molecule comprising a nucleotide sequence that encodes an antibody, or antigen-binding fragment thereof, described herein. Also provided herein is an expression vector comprising the nucleic acid molecule, operably linked to a regulatory control sequence. Also provided herein is a host cell comprising a vector or a nucleic acid molecule provided herein. Also provided herein is a method of using the host cell to produce an antibody, comprising culturing the host cell under suitable conditions such that the nucleic acid is expressed to produce the antibody.

Quantifying Selectivity of a Heavy Chain Nolynentide for a Light Chain Nolynentide:

Operationally, as used herein, HTS refers to a method that leverages automation, for example, high density arrays, liquid handling devices, detectors and high data packet processing to quickly assay the biological or biochemical activity of a large number of compounds.

Surface Plasmon Resonance (SPR) and ELISAs can be high throughput or low throughput depending on whether the above elements are applied. The parameter being assessed is also taken into consideration. Other high throughput assay types are described else where herein and may be used in the methods described herein.

In one embodiment, there is provided a high-throughput method of quantifying selectivity of a heavy chain polypeptide for pairing with at least one light chain polypeptide comprising the steps of: co-expressing a set of constructs in vitro or in a host cell, a first heavy chain polypeptide comprising a VH and a CH1 region; a first light chain polypeptide comprising a first VL region and first CL region; and a second light chain polypeptide comprising a second VL region and second CL region; wherein said heavy chain polypeptide and said light chain polypeptides are expressed such that the total amount of the heavy chain polypeptide is limiting; and wherein co-expressing the set of constructs results in a set of polypeptide products; isolating heavy chain-paired polypeptide products comprising the heavy chain polypeptide paired with said first or second light chain polypeptide from the set of polypeptide products; and quantitating the amount of heavy chain polypeptide paired with said first light chain polypeptide, and the amount of heavy chain polypeptide paired with said second light chain polypeptide in the heavy chain paired polypeptide constructs; wherein a greater amount of the heavy chain polypeptide paired with one of said first or second light chain polypeptide as compared to the other light chain polypeptide indicates selectivity of the heavy chain polypeptide for pairing with said first or second light chain polypeptide.

In embodiments, the total amount of the heavy chain polypeptide is limiting. Accordingly, in the presence of excess amounts of light chain polypeptides, the amount of heavy chain-light chain constructs formed is limited by the amount of heavy chain polypeptide since the constructs cannot be formed without it. In some embodiments, the heavy chain polypeptide, and first and second light chain polypeptides are expressed in a predetermined ratio of about 0.25:1:1.

In some embodiments, the heavy chain polypeptide, and first and second light chain polypeptides are expressed in a predetermined ratio of about 0.5:1:1. In an embodiment, the heavy chain polypeptide, and first and second light chain polypeptides are expressed in a predetermined ratio of about 1:2:2. In further embodiments, the heavy chain polypeptide, and first and second light chain polypeptides are expressed in a predetermined ratio of about 1:3:3.

In embodiments, the total amount of the light chain polypeptide is limiting. Accordingly, in the presence of excess amounts of heavy chain polypeptides, the amount of light chain-heavy chain constructs formed is limited by the amount of light chain polypeptide since the constructs cannot be formed without it. In some embodiments, the light chain polypeptide, and first and second heavy chain polypeptides are expressed in a predetermined ratio of about 0.25:1:1.

In other embodiments, the the light chain polypeptide, and first and second heavy chain polypeptides are expressed in a predetermined ratio of about 0.5:1:1. In selected embodiments, the light chain polypeptide, and first and second heavy chain polypeptides are expressed in a predetermined ratio of about 1:2:2. In some embodiments, the light chain polypeptide, and first and second heavy chain polypeptides are expressed in a predetermined ratio of about 1:3:3.

In certain embodiments, the quantification further comprises determination of control standards for the interaction of the heavy chain polypeptide with each light chain polypeptide. In certain embodiments, the quantification of control standards comprises the steps of: co-expressing said heavy chain polypeptide and one of said first and second light chain polypeptide in vitro or in a host cell, in the absence of other light chain polypeptides; isolating a construct comprising the heavy chain polypeptide and said light chain polypeptide; and quantitatively detecting the amount of said construct, wherein said amount serves as a control standard for maximum detectable binding of said heavy chain polypeptide with said light chain polypeptide.

Provided herein are methods for quantitatively determining the selective pairing of individual IgG heavy chain polypeptides with a particular IgG light chain polypeptide when the heavy chain polypeptide and at least two unique light chain polypeptides are co-expressed. The method allows quantitative analysis of the pairing of heavy chains with specific light chains within the mixture of co-expressed proteins. In one embodiment, the method can be used to determine if one particular IgG heavy chain selectively associates with either one of the two IgG light chains when the heavy chain and light chains are co-expressed. In another embodiment, the method can be used to determine if each of two different heavy chains selectively pairs with one of two light chains when the heavy and light chains are co-expressed.

In certain embodiments is a method comprising the steps of: co-expressing at least one heavy chain and two different light chains in a cell, in ratios such that the heavy-chain is the limiting pairing reactant; optionally separating the secreted proteins from the cell; separating the light chain polypeptides bound to heavy chain from the rest of the secreted proteins to produce an isolated heavy chain paired fraction; detecting the amount of each different light chain in the isolated heavy chain fraction; and analyzing the relative amount of each different light chain in the isolated heavy chain fraction to determine the ability of the at least one heavy chain to selectively pair with one of the light chains.

Provided are high-throughput methods of determining selectivity of a heavy chain polypeptide for pairing with at least one light chain polypeptide comprising the steps of obtaining: a heavy chain polypeptide comprising an immunoglobulin heavy chain region; a first light chain polypeptide comprising a first immunoglobulin light chain region; and at least one second light chain polypeptide comprising a second immunoglobulin light chain region; contacting in a solution said heavy chain polypeptide and said light chain polypeptides in a pre-determined ratio such that the total amount of the heavy chain polypeptide is limiting; isolating heavy chain-paired polypeptide products comprising the heavy chain polypeptide paired with said first or second light chain polypeptide from the set of polypeptide products; and quantitating the amount of heavy chain polypeptide paired with said first light chain polypeptide, and the amount of heavy chain polypeptide paired with said second light chain polypeptide; wherein a greater amount of the heavy chain polypeptide paired with one of said first or second light chain polypeptide as compared to the other light chain polypeptide indicates selectivity of the heavy chain polypeptide for pairing with said first or second light chain polypeptide.

In certain embodiments of the methods and assays provided herein, the heavy chain polypeptide further comprises a CH3 region. In some embodiments, the heavy chain polypeptide also comprises a CH2 region or fragment thereof. In some embodiments, at least one of the CH2 and CH3 region comprises at least one amino acid mutation. In a particular embodiment, the CH3 region comprises at least one amino acid mutation such that the CH3 region preferentially forms a heterodimer with another heavy chain polypeptide comprising a CH3 region.

Certain embodiments of the methods and assays provided herein, further comprise co-expression of a second heavy chain polypeptide comprising a CH3 region. In some embodiments, the second heavy chain polypeptide also comprises a CH2 region or fragment thereof. In some embodiments, at least one of said CH2 and CH3 region comprises at least one amino acid mutation. In a particular embodiment, the CH3 region comprises at least one amino acid mutation such that the CH3 region preferentially forms a heterodimer with the first heavy chain polypeptide comprising a CH3 region. Suitable CH3 domains comprising at least one amino acid mutation are known in the art and include, for example, those described in International Patent Publication No. WO 2012/058768, and U.S. Pat. Nos. 5,821,333, and 7,695,936. Additional amino acid mutations in the CH3 region that promote preferential formation of a first heavy chain with a second heavy chain are described in International Patent Publication No. WO 96/027011 (knobs into holes), in Gunasekaran et al. ((2010) *J Biol Chem.* 285, 19637-46, electrostatic design to achieve selective heterodimerization), in Davis et al. ((2010) *Prot Eng Des Sel;* 23(4): 195-202, strand exchange engineered domain (SEED) technology), and in Moore et al., (2011) *Mabs* 3:6, 546-557.

Assaying Selective Formation of Fab-Containing Constructs

Provided are assays and methods for determining the selective formation of a Fab-containing construct in the presence of competing heavy or light chain polypeptides or combinations thereof, said method comprising: co-expressing in vitro or in a host cell, a first heavy chain polypeptide comprising a VH and a CH1 region; a first light chain polypeptide comprising a first VL and first CL region; wherein said first light chain polypeptide selectively associates with said heavy chain polypeptide to form a desired Fab construct; and one or more other heavy chain polypeptides, light chain polypeptides or combinations thereof; isolating each Fab construct comprising said first heavy chain polypeptide or said first light chain polypeptide; and detecting the amount of desired Fab construct as compared to other Fab constructs; wherein a greater amount of the desired Fab construct demonstrates a higher selectivity of formation of said Fab construct. In certain embodiments, the method is useful to test the self-association of rationally designed Fab constructs in the presence of other heavy or light chain polypeptides.

Modification of Polypeptides

In certain embodiments, the methods, assays, and systems described herein use heavy chain polypeptides and light chain polypeptides that have been modified by the addition of a tag comprising a detectable moiety (label). The methods described herein are highly transferable for standard antibody Fab light and heavy chain pairs, unless the protein domains and tags interact in a nonspecific manner. Accordingly, the method provided herein can be used with any heavy chain or light chain, provided that it can be tagged without interfering with function or stability of the heavy or light chain. In other words, the addition of a tag should not interfere with the ability of the heavy chain to bind to a light chain, nor should it affect, for example, its expression in or secretion from the cell. Likewise, the addition of a tag should not interfere with the ability of the light chain to bind to a heavy chain, nor should it affect its expression in or secretion from the cell.

In one embodiment, at least one of the co-expressed heavy and light chain polypeptides is modified by the addition of a tag that allows for the detection and/or purification of the heavy chain or light chain in a mixture of proteins. In some embodiments, each of the co-expressed heavy and light chain polypeptides comprises a tag that is distinct from that of the other co-expressed heavy and light chains. In one embodiment, is an IgG heavy chain polypeptide that comprises a tag that allows the heavy chain and polypeptides bound to the heavy chain to be purified from a mixture of polypeptides, while each light chain comprises a tag comprising a detection moiety that allows its detection.

Tags and/or detection moieties can be added at amino or carboxy terminal ends provided that the tag and/or detection moiety can be detected and that the location of the tag and/or detection moiety does not interfere with the function and/or stability of the heavy or light chain. For example the heavy chains can be tagged at the amino terminus, and the light chains can be tagged at the carboxy terminus, or vice-versa. The tags function as unique markers of the heavy chain and two different light chains being tested. The tags can be employed interchangeably as long as the one on the heavy chain and the two different light chains are all unique. Examples of suitable tags for the heavy and light chains include, but are not limited to 6×His, FLAG, HA, c-myc, sFLAG, V5, SBP (streptavidin-binding peptide).

In certain embodiments, wherein the difference in size between the heavy and light chains is important for differentiation between the heavy and light chains, for example in embodiments where a fragment of the heavy chain is co-expressed with the light chains, one of the chains can be modified with a tag that increases its size. In an exemplary embodiment, a suitable tag is an albumin binding domain. In some embodiments, the heavy chain or portion thereof is modified by the addition of tag that increases its size.

Expression of Heavy and Light Chain Polypeptides

The polypeptides described herein can readily be prepared according to known methods. For example, methods of tagging heavy chain polypeptides and/or light chain polypeptides using recombinant DNA technology are well known. In addition, methods of expressing and co-expressing antibody polypeptides in a host cell are also well known. Expression vectors and host cells suitable for expression of the heavy and light chain polypeptides are provided herein.

Recombinant expression of heavy and light chain polypeptides requires construction of an expression vector containing a polynucleotide that encodes a heavy or light chain polypeptide described herein. Once a polynucleotide encoding the heavy or light chain has been obtained, the vector for the production of the heavy or light chain polypeptide may be produced by recombinant DNA technology. Thus, methods for preparing a protein by expressing a polynucleotide containing the heavy or light chain polypeptide encoding nucleotide sequence are described herein. Methods that are well known to those skilled in the art can be used to construct expression vectors containing heavy or light chain polypeptide coding sequences and appropriate transcriptional and translational control signals. These methods include, for example, in vitro recombinant DNA techniques, synthetic techniques, and in vivo genetic recombination. Provided herein are replicable vectors comprising a nucleotide sequence encoding heavy or light chain polypeptides, operably linked to a promoter.

The expression vector is transferred to a host cell by conventional techniques and the transfected cells are then cultured by conventional techniques to produce the heavy or light chain polypeptide for use in the method of the invention. In specific embodiments the heavy and light chain polypeptides for use in the method are co-expressed in the host cell, as detailed below.

A variety of host-expression vector systems may be utilized to express the heavy and light chain polypeptides provided herein. Such host-expression systems represent vehicles by which the coding sequences of interest may be produced and subsequently purified, but also represent cells which may, when transformed or transfected with the appropriate nucleotide coding sequences, express the modified heavy and light chains in situ. These include but are not limited to microorganisms such as bacteria for instance, but not restricted to *E. coli* and *B. subtilis*, transformed with recombinant bacteriophage DNA, plasmid DNA or cosmid DNA expression vectors containing the modified heavy and light chain coding sequences; yeast for instance, but not restricted to Saccharomyces Pichia, transformed with recombinant yeast expression vectors containing heavy and light chain polypeptide coding sequences; insect cell systems infected with recombinant virus expression vectors, for instance, but not restricted to baculovirus, containing heavy and light chain polypeptide coding sequences; plant cell systems infected with recombinant virus expression vectors, for instance, but not restricted to cauliflower mosaic virus, CaMV; tobacco mosaic virus, TMV, or transformed with recombinant plasmid expression vectors (e.g., Ti plasmid) containing heavy and light chain polypeptides coding sequences; or mammalian cell systems for instance COS, CHO, BHK, HEK-293, NSO, 3T3 cells and combinations and variants thereof harboring recombinant expression constructs containing promoters derived from the genome of mammalian cells (e.g., metallothionein promoter) or from mammalian viruses (e.g., the adenovirus late promoter; the vaccinia virus 7.5K promoter). In certain embodiments, bacterial cells such as *Escherichia coli*, or eukaryotic cells, are used for the co-expression of heavy and light chain polypeptides. In some embodiments, mammalian cells such as Chinese hamster ovary cells (CHO), in conjunction with a vector such as the major intermediate early gene promoter element from human cytomegalovirus is an effective expression system for co-expression of the light and heavy chain polypeptides described herein (Foecking et al., 1986, *Gene* 45:101; and Cockett et al., 1990, *Bio/Technology* 8:2). In a specific embodiment, the expression of nucleotide sequences encoding heavy and light chain polypeptides is regulated by a constitutive promoter, inducible promoter or tissue specific promoter.

In mammalian host cells, a number of viral-based expression systems may be utilized. In cases where an adenovirus is used as an expression vector, the heavy and light chain polypeptide coding sequences of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the heavy and light chain polypeptides in infected hosts (e.g., see Logan & Shenk, 1984, *Proc. Natl. Acad. Sci. USA* 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, *Methods in Enzymol.* 153:516-544).

The expression of heavy and light chain polypeptides described herein may be controlled by any promoter or enhancer element known in the art. Promoters which may be used to control the expression of the gene encoding heavy and light chain polypeptides include, but are not limited to, the SV40 early promoter region (Bernoist and Chambon, 1981, *Nature* 290:304-310), the promoter contained in the 3' long terminal repeat of Rous sarcoma virus (Yamamoto, et al., 1980, *Cell* 22:787-797), the herpes thymidine kinase promoter (Wagner et al., 1981, *Proc. Natl. Acad. Sci. U.S.A.* 78.1441-1445), the regulatory sequences of the metallothionein gene (Brinster et al., 1982, *Nature* 296:39-42), the tetracycline (Tet) promoter (Gossen et al., 1995, *Proc. Nat. Acad. Sci. USA* 89:5547-5551); prokaryotic expression vectors such as the β-lactamase promoter (Villa-Kamaroff et al, 1978, *Proc. Natl. Acad. Sci. U.S.A.* 75:3727-3731), or the tac promoter (DeBoer et al., 1983, *Proc. Natl. Acad. Sci. U.S.A.* 80:21-25; see also "Useful proteins from recombinant bacteria" in Scientific American, 1980, 242:74-94); plant expression vectors comprising the nopaline synthetase promoter region (Herrera-Estrella et al., *Nature* 303:209-213) or the cauliflower mosaic virus 35S RNA promoter (Gardner et al., 1981, *Nucl. Acids Res.* 9:2871), and the promoter of the photosynthetic enzyme ribulose biphosphate carboxylase (Herrera-Estrella et al., 1984, *Nature* 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, *Cell* 38:639-646; Ornitz et al., 1986, Cold Spring Harbor Symp. Quant. Biol. 50:399-409; MacDonald, 1987, *Hepatology* 7:425-515); insulin gene control region which is active in pancreatic beta cells (Hanahan, 1985, *Nature* 315:115-122), immunoglobulin gene control region which is active in lymphoid cells (Grosschedl et al., 1984, *Cell* 38:647-658; Adames et al., 1985, *Nature* 318:533-538; Alexander et al., 1987, Mol. Cell. Biol. 7:1436-1444), mouse mammary tumor virus control region which is active in testicular, breast, lymphoid and mast cells (Leder et al., 1986, *Cell* 45:485-495), albumin gene control region which is active in liver (Pinkert et al., 1987, *Genes and Devel.* 1:268-276), alpha-fetoprotein gene control region which is active in liver (Krumlauf et al., 1985, *Mol. Cell. Biol.* 5:1639-1648; Hammer et al., 1987, Science 235:53-58; alpha 1-antitrypsin gene control region which is active in the liver (Kelsey et al., 1987, *Genes and Devel.* 1:161-171), beta-globin gene control region which is active in myeloid cells (Mogram et al., 1985, *Nature* 315:338-340; Kollias et al., 1986, *Cell* 46:89-94; myelin basic protein gene control region which is active in oligodendrocyte cells in the brain (Readhead et al., 1987, *Cell* 48:703-712); myosin light chain-2 gene control region which is active in skeletal muscle (Sani, 1985, *Nature* 314:283-286); neuronal-specific enolase (NSE) which is active in neuronal cells (Morelli et al., 1999, *Gen. Virol.* 80:571-83); brain-derived neurotrophic factor (BDNF) gene control region which is active in neuronal cells (Tabuchi et al., 1998, *Biochem. Biophysic. Res. Com.* 253:818-823); glial fibrillary acidic protein (GFAP) promoter which is active in astrocytes (Gomes et al., 1999, *Braz J Med Biol Res* 32(5): 619-631; Morelli et al., 1999, *Gen. Virol.* 80:571-83) and gonadotropic releasing hormone gene control region which is active in the hypothalamus (Mason et al., 1986, Science 234:1372-1378).

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered fusion protein may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells that possess the cellular machinery for proper processing of the primary transcript (e.g., glycosylation, and phosphorylation) of the gene product may be used. Such mammalian host cells include, but are not limited to, CHO, VERY, BHK, Hela, COS, MDCK, HEK-293, 3T3, WI38, NSO, and in particular, neuronal cell lines such as, for example, SK-N-AS, SK-N-FI, SK-N-DZ human neuroblastomas (Sugimoto et al., 1984, *J. Natl. Cancer Inst.* 73: 51-57), SK-N-SH human neuroblastoma (*Biochim. Biophys. Acta*, 1982, 704: 450-460), Daoy human cerebellar medulloblastoma (He et al., 1992, *Cancer Res.* 52: 1144-1148) DBTRG-05MG glioblastoma cells (Kruse et al., 1992, *In Vitro Cell. Dev. Biol.* 28A: 609-614), IMR-32 human neuroblastoma (*Cancer Res.*, 1970, 30: 2110-2118), 1321 N1 human astrocytoma (*Proc. Natl. Acad. Sci. USA*, 1977, 74: 4816), MOG-G-CCM human astrocytoma (*Br. J. Cancer,* 1984, 49: 269), U87MG human glioblastoma-astrocytoma (Acta *Pathol. Microbiol. Scand.*, 1968, 74: 465-486), A172 human glioblastoma (Olopade et al., 1992, *Cancer Res.* 52: 2523-2529), C6 rat glioma cells (Benda et al., 1968, *Science* 161: 370-371), Neuro-2a mouse neuroblastoma (*Proc. Natl. Acad. Sci. USA,* 1970, 65: 129-136), NB41A3 mouse neuroblastoma (*Proc. Natl. Acad. Sci. USA,* 1962, 48: 1184-1190), SCP sheep choroid plexus (Bolin et al., 1994, *J. Virol. Methods* 48: 211-221), G355-5, PG-4 Cat normal astrocyte (Haapala et al., 1985, *J. Virol.* 53: 827-833), Mpf ferret brain (Trowbridge et al., 1982, *In Vitro* 18: 952-960), and normal cell lines such as, for example, CTX TNA2 rat normal cortex brain (Radany et al., 1992, *Proc. Natl. Acad. Sci. USA* 89: 6467-6471) such as, for example, CRL7030 and Hs578Bst. Furthermore, different vector/host expression systems may effect processing reactions to different extents.

For long-term, high-yield production of heavy and light chain polypeptides, stable expression systems may be used. For example, cell lines that stably express the heavy and light chain polypeptides described herein may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci that in turn can be cloned and expanded into cell lines.

A number of selection systems may be used, including but not limited to the herpes simplex virus thymidine kinase (Wigler et al., 1977, *Cell* 11:223), hypoxanthine-guanine phosphoribosyltransferase (Szybalska & Szybalski, 1962, *Proc. Natl. Acad. Sci. USA* 48:2026), and adenine phosphoribosyltransferase (Lowy et al., 1980, *Cell* 22:817) genes can be employed in tk-, hgprt- or aprt-cells, respectively. Also, antimetabolite resistance can be used as the basis of selection for dhfr, which confers resistance to methotrexate (Wigler et al., 1980, *Proc. Natl. Acad. Sci. USA* 77:3567; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (Colberre-Garapin et al., 1981, *J. Mol. Biol.* 150:1); and hygro, which confers resistance to hygromycin (Santerre et al., 1984, *Gene* 30:147) genes.

In certain embodiments, cell-free protein expression systems are utilized to co-express the heavy and light chain polypeptides without the use of living cells. Instead, all components needed to transcribe DNA to RNA and translate the RNA to protein (e.g., ribosomes, tRNAs, enzymes, cofactors, amino acids) are provided in solution for use in vitro. In certain embodiments, the in vitro expression requires (1) the genetic template (mRNA or DNA) encoding the heavy and light chain polypeptides and (2) a reaction solution containing the necessary transcriptional and translational molecular machinery. In certain embodiments, cell extracts substantially supply components of the reaction solution, for instance: RNA polymerases for mRNA transcription, ribosomes for polypeptide translation, tRNA, amino acids, enzymatic cofactors, an energy source, and cellular components essential for proper protein folding. Cell-free protein expression systems can be prepared using lysates derived from bacterial cells, yeast cells, insect cells, plant cells, mammalian cells, human cells or combinations thereof. Such cell lysates provide the correct composition and proportion of enzymes and building blocks required for translation. In some embodiments, cell membranes are removed to leave only the cytosolic and organelle components of the cell.

Several cell-free protein expression systems are known in the art as reviewed in Carlson et al. (2012) Biotechnol. Adv. 30:1185-1194. For example, cell-free protein expression systems are available based on prokaryotic or eukaryotic cells. Examples of prokaryotic cell-free expression systems include those from E. coli. Eukaryotic cell-free protein expression systems are available based on extracts from rabbit reticulocytes, wheat germ, and insect cells, for example. Such prokaryotic and eukaryotic cell-free protein expression systems are commercially available from companies such as Roche, Invitrogen, Qiagen, and Novagen. One skilled in the art would readily be able to select suitable cell-free protein expression systems that would produce heavy chain and light chain polypeptides that are capable of pairing with each other. Further, the cell-free protein expression system could also be supplemented with chaperones (e.g., BiP) and isomerases (e.g., disulphide isomerase) in order to improve the efficiency of IgG folding.

In some embodiments, cell-free expression systems are utilized to co-express the heavy and light chain polypeptides from DNA templates (transcription and translation) or mRNA templates (translation only).

In one embodiment, the method is carried out with heavy and light chains that are linked via a canonical disulphide bridge. In other embodiments, the method is carried out with heavy and light chain polypeptides that are not linked via a canonical disulphide bridge.

Co-Expression of Heavy and Light Chain Polypeptides

The set of constructs encoding the heavy and light chain polypeptides to be tested are co-expressed in host cells or in a cell-free protein expression system and are recovered from the culture or reaction medium. Co-expresion the set of constructs results in a set of polypeptide products. In certain embodiments, the set of polypeptide products secreted from the cell may include heavy chains paired with light chains, as well as light chain monomers and dimers.

In certain embodiments provided herein, host cells are transfected with stoichiometric amounts of the DNA encoding the two light chains, while the amount of DNA encoding the heavy chain is limiting. LCCA ratios may be determined by screening. In one embodiment the ratio of transfection of heavy chain polypeptide (HC) to first light chain polypeptide (LC1) and second light chain polypeptide (LC2), i.e., HC:LC1:LC2 is 1:1:1. In one embodiment the ratio of transfection of heavy chain polypeptide (HC) to first light chain polypeptide (LC1) and second light chain polypeptide (LC2), i.e., HC:LC1:LC2 is 3:1:1 to determine, in some instances, if LC1 and LC2 are equally expressed. In another embodiment the ratio of transfection of heavy chain polypeptide (HC) to first light chain polypeptide (LC1) and second light chain polypeptide (LC2), i.e., HC:LC1:LC2 is 0.5:1:1. In some embodiments, the heavy chain polypeptide, and first and second light chain polypeptides are expressed in a predetermined ratio of about 1:2:2. In an embodiment, the ratio of heavy chain polypeptide, and first and second light chain polypeptides are expressed in a predetermined ratio of about 1:3:3. It would be understood that other ratios may be used and are contemplated herein. In a non-limiting example, LCCA dose verification ratios for HC:LC1:LC2 may be (50:75:25, 50:50:50 and 50:25:75) or (50:40:60, 50:50:50 and 50:60:40).

In certain embodiments where the set of constructs is co-expressed in a cell-free protein expression system, ratios of DNA encoding the two light chains and heavy chains is similar to the case where the set of constructs is co-expressed in a host cell.

In certain embodiments provided herein, host cells are transfected with stoichiometric amounts of the DNA encoding two heavy chains, while the amount of DNA encoding the light chain is limiting. In one embodiment the ratio of transfection of light chain polypeptide (LC) to first heavy chain polypeptide (HC1) and second heavy chain polypeptide (HC2), i.e., LC:HC1:HC2 is 1:1:1. In another embodiment the ratio of transfection of light chain polypeptide (LC) to first heavy chain polypeptide (HC1) and second heavy chain polypeptide (HC2), i.e., LC:HC1:HC2 is 0.5:1:1. In some embodiments, the light chain polypeptide, and first and second heavy chain polypeptides are expressed in a predetermined ratio of about 1:2:2. In an embodiment, the ratio of light chain polypeptide, and first and second heavy chain polypeptides are expressed in a predetermined ratio of about 1:3:3.

In certain embodiments where the set of constructs is co-expressed in a cell-free protein expression system, ratios of DNA encoding the two heavy chains and light chain is similar to the case where the set of constructs is co-expressed in a host cell.

In certain embodiments, a method of quantifying selectivity of a heavy chain polypeptide for pairing with at least one light chain polypeptide described herein, includes expression of at least two control samples in order to allow for the analysis of data. In some embodiments, the method of obtaining and quantifying the control sample comprises co-expressing the heavy chain polypeptide and one of the first and second light chain polypeptide, in the absence of other light chain polypeptides; isolating any construct comprising the heavy chain polypeptide and the light chain polypeptide; and quantifying the amount of said construct, wherein said amount serves as a control standard for maximum detectable binding of said heavy chain polypeptide with said light chain polypeptide. In certain embodiments, the controls are antibodies where heavy-chain is expressed with a light-chain having one of the two light-chain tags used for labeling. These control expressions produce a protein mixture where the ratio of light-chains with different tags is controlled by the experiment and not the physical interaction between heavy and light chain.

Once the heavy chain, light chains, and control samples are co-expressed and secreted from the cell, they may optionally be separated from the cells in culture as described below.

Separation of Secreted Proteins from Cell

Certain embodiments of methods and assays described herein use heavy and light chain polypeptides that are co-expressed from a cell. Depending on the format of the assay, the optional step of separating the secreted proteins from the cells from which they are expressed may be included. In certain embodiments, for assays utilizing surface plasmon resonance (SPR) or FACS the optional step of separating secreted proteins from the cell may be included. In certain embodiments, in formats that use, for example, bimolecular fluorescence complementation it may not be necessary to include the step of separating the secreted proteins from the cells.

Methods of separating the secreted proteins from the cells are well known in the art. In one embodiment, centrifugation is used to separate the secreted proteins from the cells. In an alternate embodiment, column purification is used to separate the secreted proteins from the cells.

The secreted proteins are subsequently used to prepare the isolated heavy chain fraction.

Figure 9:
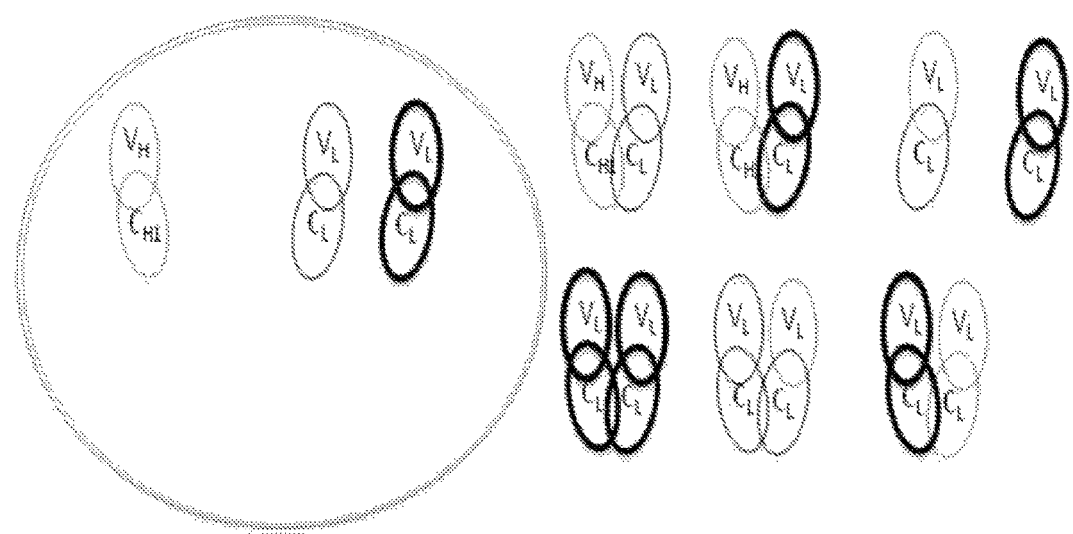
FIG. 9 provides a cartoon depiction of an exemplary LCCA where HC is limiting.
Figure 10:
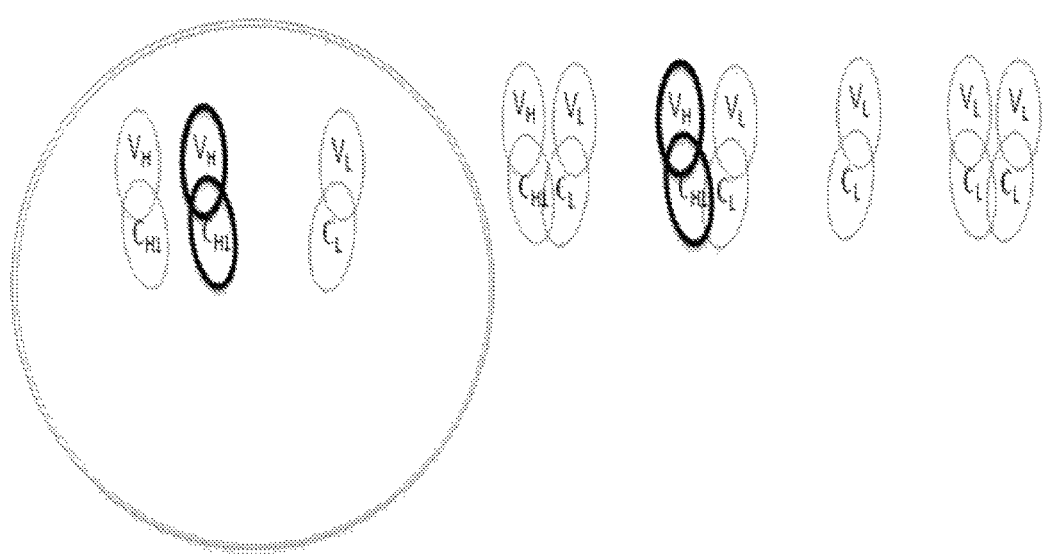
FIG. 10 provides a cartoon depiction of an exemplary HCCA where LC is limiting.
Figure 11:
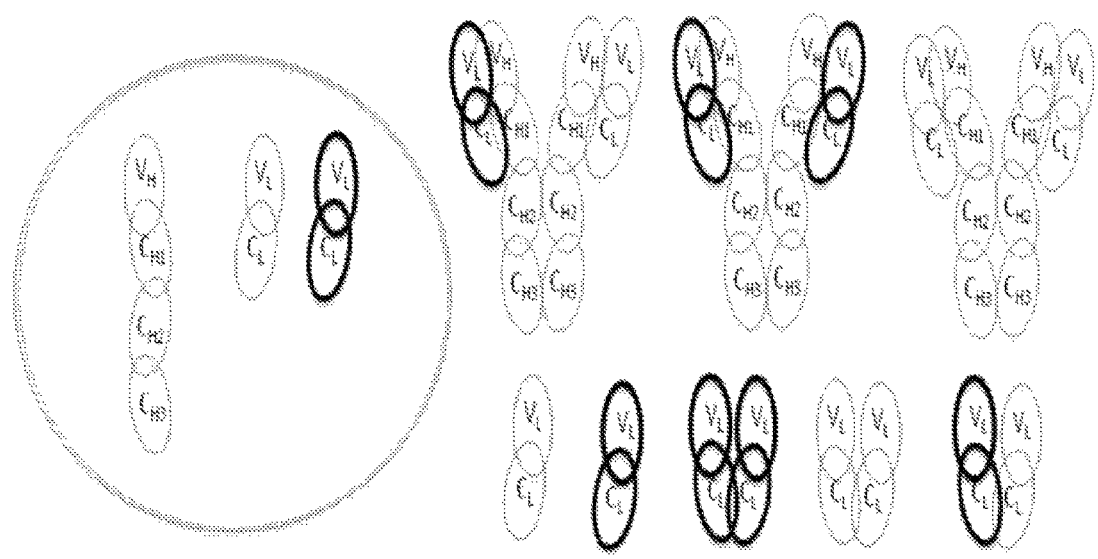
FIG. 11 provides a cartoon depiction of an exemplary LCCA where full-length HC polypeptides are limiting.
Figure 12:
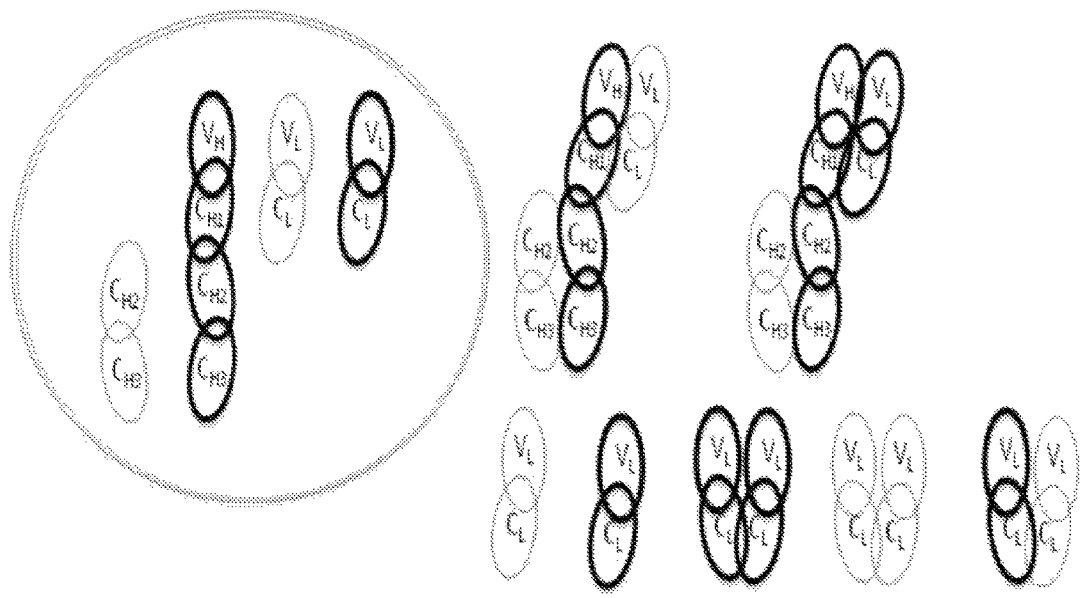
FIG. 12 provides a cartoon depiction of an exemplary ORCA where full-length HC polypeptides are limiting (HET_FC used).

Depending on the design of the assay, the composition of the products in the set of paired polypeptide products will vary. FIG. 9 depicts some of the expected products secreted into the medium when the set of constructs is co-expressed in whole cells in an embodiment where the set of constructs comprises one heavy chain, and two unique light chains. FIG. 10 depicts some of the expected products secreted into the medium when the set of constructs is co-expressed in whole cells in an embodiment where the set of constructs comprises two unique heavy chains, and one light chain. FIG. 11 depicts some of the expected products secreted into the medium when the set of constructs is co-expressed in whole cells in an embodiment where the set of constructs comprises one full-length heavy chain, and two unique light chains. FIG. 12 depicts some of the expected products secreted into the medium when the set of constructs is co-expressed in whole cells in an embodiment where the set of constructs comprises one full-length heavy chain, one heavy chain fragment comprising a CH2 region and a CH3 region, and two unique light chains.

Preparation of Isolated Heavy Chain-Paired Polypeptide Products

The heavy chain-paired polypeptide products are isolated from the set of polypeptide products. As used herein, the term "heavy chain-paired polypeptide products" refers to expressed polypeptides that are paired with a heavy chain, for example, a first heavy chain polypeptide paired with a first light chain polypeptide or with a second light chain polypeptide. In one embodiment, where the set of constructs comprises one heavy chain and a first and second light chain, the heavy chain polypeptide bound to a partner light chain polypeptide may be isolated by making use of an affinity of the recognition moiety on the tag on the heavy chain for particular protein separation phase. Alternatively, the heavy chain-paired polypeptide products can be isolated using an antibody that specifically recognizes the heavy chain. Such antibodies are known in the art and include, for example, antibodies directed to the CH1 region of the heavy chain polypeptide. The isolated heavy chain-paired polypeptide products will have the heavy chain polypeptide and a light chain polypeptide bound to it. As a specific non-limiting example, if a heavy chain is tagged with a 6×his tag, nickel can be used to separate the heavy chains from other proteins in the mixture. The nickel can be bound to a support, such as for example, a column or a chip.

Once the heavy chain-paired polypeptide products have been isolated, specific light chain polypeptides bound to the heavy chain polypeptide can be detected.

Detection of Light Chain Polypeptides

In some embodiments, the detection of light chain polypeptide paired to the heavy chain polypeptide is carried out based on the detection moiety in the tag added to each light chain, according to methods known in the art. For example, if a light chain is tagged with FLAG, then the light chain can be detected with an anti-FLAG antibody. In some embodiments, the light chain polypeptide is itself detected by use of a protein with high affinity for an amino acid sequence on the light chain polypeptide. In some embodiments, the light chain polypeptide is detected by use of one or more of fluorescence, quenching, radioactivity and chemiluminescence.

Assay Formats

Various formats are contemplated for preparation of the isolated heavy chain fraction. For example, the isolated heavy chain-paired polypeptide products can be isolated by a method including, but not limited to, ELISA, SPR chips, bimolecular fluorescence complementation readout, Fluorescence-Activated Cell Sorting (FACS), DELFIA®, fluorescence polarization/anisotropy (FP), fluorescent/Foerster resonance energy transfer (FRET, TR-FRET, HTRF), and AlphaScreen®.

Surface Plasmon Resonance (SPR)

In certain embodiments, the methods, assays and systems described herein utilize surface plasmon resonance to quantitatively determine selective pairing of heavy chain polypeptides and light chain polypeptides. Surface plasmon resonance (SPR) affords a high throughput method, wherein surface plasmons resonate upon excitation by electromagnetic radiation entering an interface of metallic material and a dielectric material. Surface plasmon resonance useful for the detection of biomolecular interactions, such as the interaction between a heavy chain polypeptide and a light chain polypeptide. In certain embodiments described herein are provided devices to utilize SPR for quantitative determination of selective pairing of heavy and light chain polypeptides, wherein said devices comprise a sensor chip comprising a sensor chip. In some embodiments, the sensor chip comprises an interactive surface layer capable of capturing a tag such as a detectable moiety (label) on a heavy chain polypeptide. In one embodiment, the heavy chain is tagged with a 6×his tag, and the isolated heavy chain-paired polypeptide products are isolated by passing the secreted proteins over an SPR—nickel chip. In this embodiment, the isolated heavy chain-paired polypeptide products comprising heavy chains bound to partner light chains will bind to the SPR chip. In an alternate embodiment, the isolated heavy chain-paired polypeptide products are isolated using SPR with an anti-his tag antibody chip instead of a nickel chip.

In certain embodiments, the sensor chip comprises a surface layer designed to bind histidine-tagged heavy chain polypeptides.

In some embodiments, the surface layer comprises NTA-chelated nickel atoms. The binding of the histidines on the heavy chain polypeptide relies on a NTA-chelated nickel atom. The affinity ($K_D \cong 10^{-6}$ M) of this interaction is commonly sufficiently high to allow detailed analysis of the heavy chain-light chain binding. Immobilization via His-tags has also the advantage of orientating the ligand molecules in a homogeneous way and allowing the immobilization to be carried out without significant changing the pH or ionic strength during the coupling procedure.

However, as with many other affinity tags (e.g., biotin and antigen epitopes) the affinity may vary with the microenvironment created by moieties adjacent to the His-tag. The affinity can also be affected by the buffer environment, e.g., pH and ionic strength. Although side chains of cysteine, tyrosine, tryptophan and lysine on the surface of a heavy chain polypeptide may participate in binding to a chelated metal, the affinity of these interactions are typically significantly lower than that commonly obtained with histidine tags. In some embodiments, the heavy chain polypeptide concentration is at least about 10 nM. In certain embodiments, the heavy chain polypeptide concentration is at least about 50 nM. In certain embodiments, the heavy chain polypeptide concentration is at least about 100 nM. In certain embodiments, the heavy chain polypeptide concentration is at least about 150 nM. In certain embodiments, the heavy chain polypeptide concentration is less than about 200 nM.

Enzyme-Linked Immunosorbant—Type Assays (ELISAs)

As used herein, "ELISA: refers to means that the detection event uses an antibody and enzyme-based detection; however, this term is also used to describe plate-bound detection of a reagent, even if the affinity reagent is not an antibody or if the detection reagent is not an enzyme. ELISA-type assays can be designed in many ways. Attachment of the surface-bound protein can occur by passive adsorption to a plastic plate, by capture with an adsorbed antibody, or by biotinylation and avidin capture. Detection of the second protein can occur by direct labeling the protein with a signal-generating enzyme, by binding of an enzyme-labeled antibody, by binding of an unlabeled primary antibody followed by a labeled secondary antibody, or by biotinylation followed by enzyme-linked avidin. Detection enzymes can include colorimetric, fluorogenic, or luminogenic reactions. Assays such as these are known in the art and are available in immunological and cellular protocol books including, but not limited to, those set forth in the Assay Guidance Manual by Arkin et al. (Sittampalam et al., Eds., *Inhibition of Protein-Protein Interactions: Non-Cellular Assay Formats*).

ELISAs utilize a device comprising an interactive surface layer useful to immobilize a heavy chain polypeptide by interacting with a recognition moiety on said heavy chain polypeptide. The light chain polypeptide bound to the heavy chain polypeptide is detected by binding of an antibody that is linked to an enzyme. When substrate is added, the enzyme produces a measurable readout that is quantitatively linked to the amount of the light chain polypeptide. ELISAs can be very sensitive, because the readout is amplified by using an enzyme. In certain embodiments, further amplification is achieved by using multiple layers, such as secondary antibodies.

Though ELISA technically means that the detection event uses an antibody and enzyme-based detection; in some embodiments, the affinity reagent is not an antibody or if the detection reagent is not an enzyme. In some embodiments is a non-enzymatic format called Dissociation-Enhanced Lanthanide Fluorescent Immunoassay (DELFIA). In DELFIA, the detection signal is time-resolved fluorescence of a lanthanide ion for instance, europium. The lanthanide ion is bound to the affinity reagent through a chemical linkage; upon adding a proprietary detergent mixture, the europium fluoresces, providing a highly sensitive measurement of the concentration of bound light chain polypeptide. Three features of lanthanide fluorescence lead to highly sensitive and selective assays: a) a long emission lifetime (milliseconds) allows the measurement to start after the fluorescence of the polypeptide has decayed, b) the emission occurs at around 600 nm, where few biological materials absorb or emit light, and c) the narrow emission spectrum of lanthanides allow them to be multiplexed.

DELFIA®

DELFIA® (Dissociation-Enhanced Lanthanide Fluorescent Immunoassay) is a non-enzymatic robust, high-performance immunodetection platform that provides a combination of benefits that make it an superior alternative to conventional ELISA. DELFIA® (dissociation-enhanced lanthanide fluorescence immunoassay) is a time-resolved fluorescence (TRF) intensity technology. The assay is designed to detect the presence of a compound or biomolecule using lanthanide chelate labeled reagents, separating unbound reagent using wash steps. The technology is based on fluorescence of lanthanide chelates (e.g., Europium, Samarium, and Terbium). The fluorescence decay time of these lanthanide chelate labels is longer than traditional fluorophores, allowing efficient use of temporal resolution for reduction of auto-fluorescent background. Sensitivity is increased because of the dissociation-enhancement principle: the lanthanide chelate is dissociated and a new highly fluorescent chelate is formed into a protective micellar solution. DELFIA lanthanide chelates require this dissociation/enhancement step for fluorescence (induced by addition of DELFIA Enhancement solution, DELFIA Inducer, and DELFIA Enhancer as appropriate to the particular lanthanide chelate). Kits for DELFIA assays are commercially available from, for example, Perkin Elmer.

AlphaScreen®

AlphaScreen® Protein-Protein Interaction Assays are flexible and sensitive, homogeneous assays useful for measurement of large protein interactions and complexes up to 200 nm in size. A bead-based proximity assay, The AlphaScreen® assay is a bead-based proximity assay that is commercially available and provides solutions for fusion tag detection to assay biological interactions. This technology provides flexibility of a wide range of beads for labeling a mixture of proteins.

Other Fluorescent Methods

Some of the fluorescence immunoassay methods include simple fluorescence labeling method, fluorescence resonance energy transfer (FRET), time resolved fluorescence (TRF), and scanning probe microscopy (SPM). The simple fluorescence labeling method can be used for receptor-ligand binding, enzymatic activity by using pertinent fluorescence, and as a fluorescent indicator of various in vivo physiological changes such as pH, ion concentration, and electric pressure. TRF is a method that selectively measures fluorescence of the lanthanide series after the emission of other fluorescent molecules is finished. TRF can be used with FRET and the lanthanide series can become donors or acceptors.

In fluorescence polarization/anisotropy (FP), fluorescence intensity can be used to provide an indication of the presence (and possibly also the amount) of a particular fluorophore in a sample. Fluorescence anisotropy can provide a measure of the degree to which fluorescent radiation is non-randomly polarized, that is, the degree to which one polarization orientation predominates over its orthogonal polarization orientation. A highly anisotropic signal is highly polarized (for example, linearly polarized). A highly isotropic signal approaches random polarization. In one conventional approach, anisotropy (r) is calculated using the following equation:

$$r = \frac{I_{VV} - G \cdot I_{VH}}{I_{VV} + 2 \cdot G \cdot I_{VH}}$$

where $I_{VH}$ and $I_{VV}$ are the horizontal and vertical polarizations (relative to vertically polarized excitation light) and G corrects for polarization bias of the optical instrument used to detect the fluorescence.

Assay Design

The method can be used to determine the selectivity of heavy and light chain pairs that have been rationally designed; naturally-occurring heavy and light chains; and the heavy and light chain pairs that can be screened in using the method are not limited by polypeptide design methodology.

The composition of the set of constructs that are co-expressed in a host cell, or in vitro, can vary. Exemplary design variations for the method are shown in Table 1.

of constructs is co-expressed such that the LC is limiting. The set of constructs is co-expressed in either whole cells or in a cell-free expression system. In the case where the set of

TABLE 1

|  | LCCA-1 | LCCA-3^ | HCCA^ | ORCA |
|---|---|---|---|---|
| Number of chains co-expressed | 3 (1 HC + 2 LC) | 4 (2 HC + 2 LC) | 3 (1 LC + 2 HC) | 4 (1 $HC_{Fc}$ + 1 HC + 2 LC) |
| Populations quantified | HC-LC1 and HC-LC2 | {HC1-LC1 and HC1-LC2} and {HC2-LC1 and HC2-LC2}# | LC-HC1 and LC-HC2 | $HC_{Fc}$HC-LC1 and $HC_{Fc}$HC-LC2 |
| Uses heterodimeric Fc? | No | No | No | Yes |
| LC tags required for quantifying populations* | Yes | Yes | No | Yes |
| HC tags required for quantifying populations* | No | No | Yes | No |
| Typical method(s) used for isolating populations | 1. HC tag (e.g., $His_6$ tag)<br>2. Anti-CH1 Ab | 1. HC tags (e.g., $His_6$ tag and V5 tag, or $His_6$ tag and cMyc tag) | 1. HC tag (e.g., $His_6$ tag)<br>2. Anti-CH1 Ab | 1. Anti-Fc Ab<br>2. Fc capture via Protein A |

LCCA: Light Chain Competition Assay,
HCCA: Heavy Chain Competition Assay
ORCA: One-aRmed light chain Competition Assay
Two sets of populations are independently quantified.
*Tags may be used in certain instances.

Table 1 also summarizes various features of each design such as which populations are quantified within the set of polypeptide products, whether the method uses Fc regions that preferentially heterodimerize with each other, and details relating to how the populations are quantified with or without tags.

Figure 15:
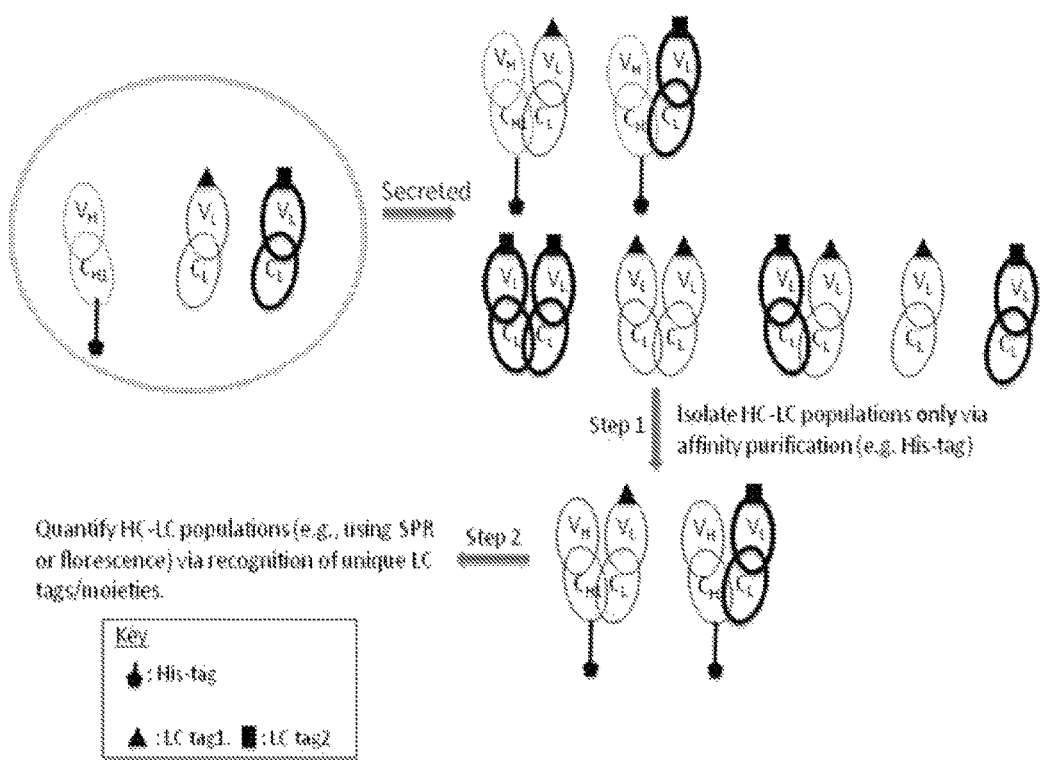
FIG. 15 provides a diagram depicting an example of how the method is carried out in an LCCA embodiment (LCCA-1). In this figure, each of the heavy and light chains is uniquely tagged (see legend).

In one embodiment, the method is set up as a Light Chain Competition Assay (LCCA). In this embodiment, the set of constructs comprises one HC plus at least two unique LCs. The HC and the two unique LCs are in the Fab format, i.e. the HC comprises a VH region and a CH1 region, while the each LC comprises a VL region and a CL region. The set of constructs is co-expressed such that the HC is limiting. The set of constructs is co-expressed in either whole cells or in a cell-free expression system. In the case where the set of constructs is co-expressed in whole cells, as indicated above, it is assumed that heavy chain products are not secreted from the cell unless they are paired with a light chain. FIG. 15 provides a diagram depicting an example of how the method is carried out in an LCCA embodiment (LCCA-1). In the embodiment shown in FIG. 15, each of the heavy and light chains is uniquely tagged. In step 1, the HC-LC paired populations (heavy chain-paired polypeptide products) are isolated by affinity purification using the tag on the heavy chain. In step 2, the population of each HC-LC pair is quantified. It is contemplated that depending on the detection method used, steps 1 and 2 can be combined. For example, when the SPR format is used for the assay, steps 1 and 2 can be combined.

Figure 16:
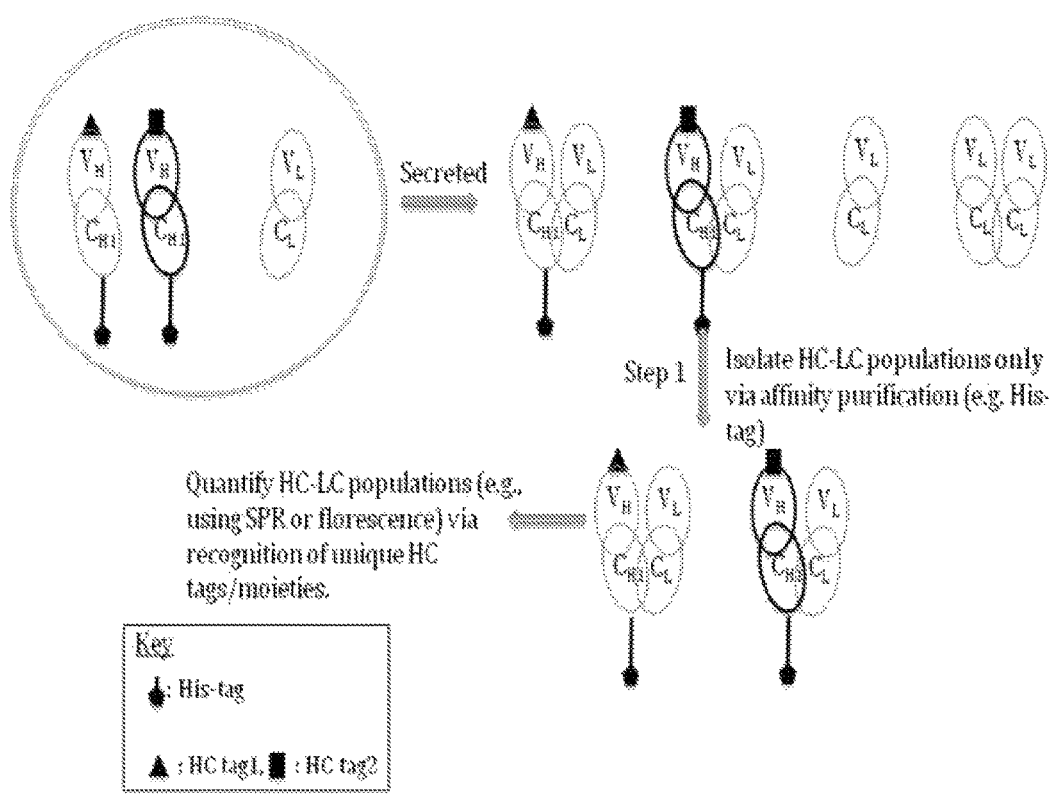
FIG. 16 provides a diagram depicting an example of how the method is carried out in an HCCA embodiment. In this figure, only the heavy chains are uniquely tagged (see legend).

In another embodiment, the method is set up as a heavy chain competition assay (HCCA). In this embodiment, the set of constructs comprises one LC plus at least two unique HCs. The LC and the two unique HCs are in the Fab format, i.e. the HC comprises a VH region and a CH1 region, while the each LC comprises a VL region and a CL region. The set constructs is co-expressed in whole cells, it is assumed that heavy chain products are not secreted from the cell unless they are paired with a light chain. FIG. 16 provides a diagram depicting an example of how the method is carried out in an HCCA embodiment. In the embodiment shown in FIG. 16, only the heavy chains are uniquely tagged. In step 1, the HC-LC paired populations (heavy chain-paired polypeptide products) are isolated by affinity purification using the tag on the heavy chain. In step 2, the population of each HC-LC pair is quantified. In this embodiment it is also possible to combine steps 1 and 2 depending on the method of quantifying the HC-LC pairs.

Figure 17:
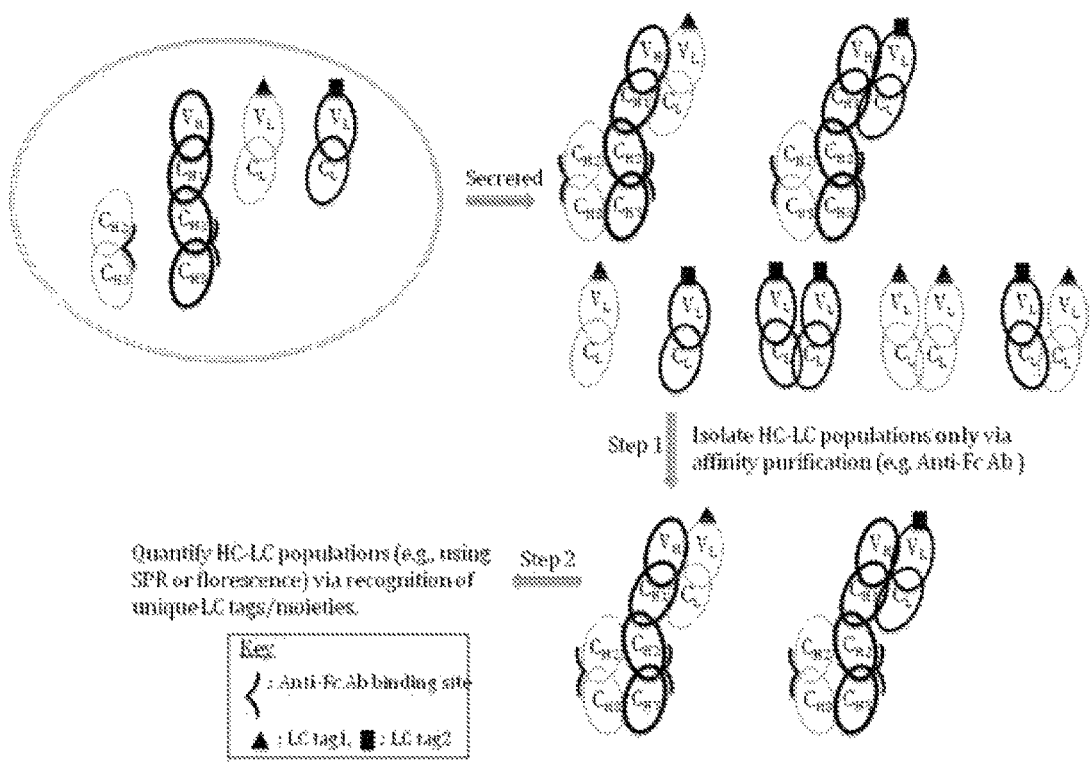
FIG. 17 provides a diagram depicting an example of how the method is carried out in an ORCA embodiment. In this figure, only the light chains are uniquely tagged (see legend).

In another embodiment, the method is set up as a one-armed light chain competition assay (ORCA). In this embodiment, the set of constructs comprises a first HC comprising a VH region, a CH1 region, a CH2 region and a CH3 region, a second HC comprising a CH2 region and a CH3 region, and two unique LCs each comprising a VL region and a CL region. In this embodiment, the CH3 regions comprise at least one modification that allows the first and second HCs to preferentially heterodimerize. The set of constructs is co-expressed in either whole cells or in a cell-free expression system, under conditions where the full-length HC is limiting. In the case where the set of constructs is co-expressed in whole cells, it is assumed that heavy chain products are not secreted from the cell unless they are paired with a light chain. FIG. 17 provides a diagram depicting an example of how the method is carried out in an ORCA embodiment. In the embodiment shown in FIG. 17, only the light chains are uniquely tagged. In this embodiment, in step 1, the HC-LC paired populations (heavy chain-paired polypeptide products) are isolated by affinity purification using an anti-Fc antibody. In step 2, the population of each HC-LC pair is quantified. In this embodiment it is also possible to combine steps 1 and 2 depending on the method of quantifying the HC-LC pairs.

Figure 18:
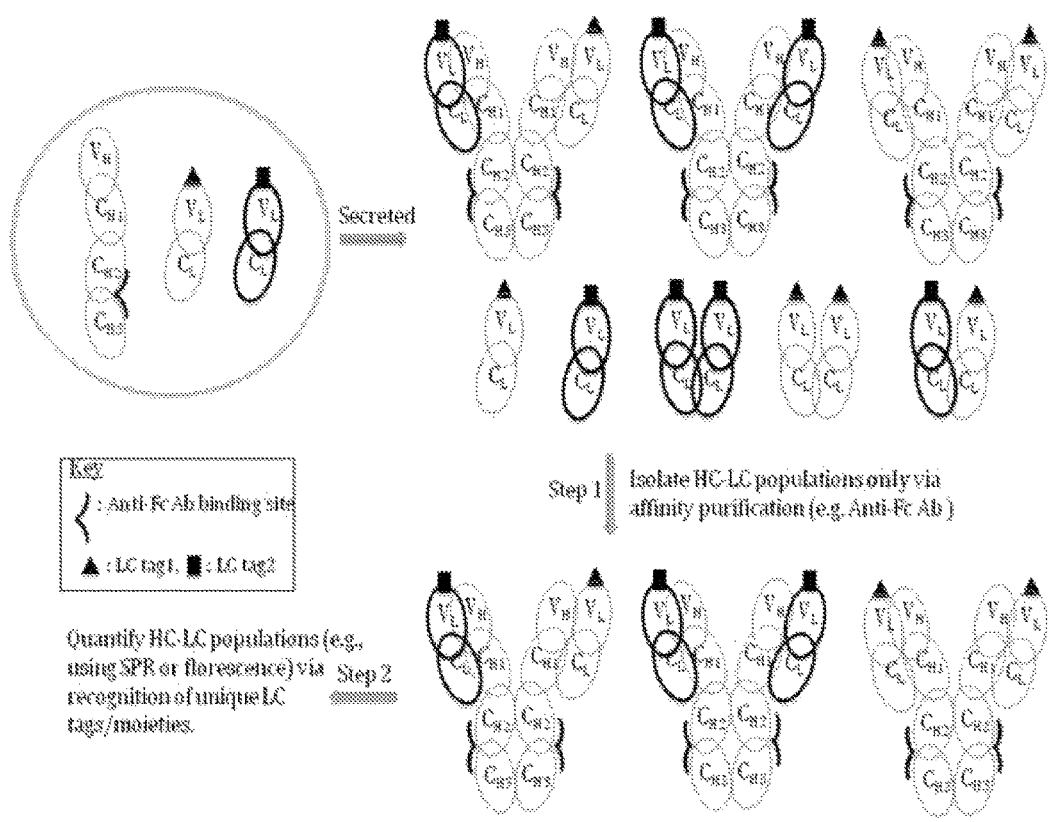
FIG. 18 provides a diagram depicting an example of how the method is carried out in an LCCA-2 embodiment. In this figure, only the light chains are uniquely tagged (see legend).

In still another embodiment, the method is set up as a variation of the LCCA-1 embodiment (LCCA-2). In this embodiment, the set of constructs comprises one HC plus at least two unique LCs, as for the LCCA-1, except the HC comprises a VH region, a CH1 region, a CH2 region, and a CH3 region, while each LC comprises a VL region and a CL region. The set of constructs is co-expressed such that the HC is limiting. The set of constructs is co-expressed in either whole cells or in a cell-free expression system. In the case where the set of constructs is co-expressed in whole cells, as indicated above, it is assumed that heavy chain products are not secreted from the cell unless they are paired with a light chain. FIG. 18 provides a diagram depicting an example of how the method is carried out in an LCCA-2 embodiment. In the embodiment shown in FIG. 18, only the light chains are uniquely tagged. In step 1, the HC-LC paired populations (heavy chain-paired polypeptide products) are isolated by affinity purification using an anti-Fc antibody. In step 2, the population of each HC-LC pair is quantified. It is contemplated that depending on the detection method used, steps 1 and 2 can be combined.

In yet another embodiment, the assay is set up as another variation of the LCCA (LCCA-3). In this embodiment, the set of constructs comprises two unique LCs plus two unique HCs. The LCs and HCs are both in the Fab format, i.e. HC comprises a VH region and a CH1 region, while each LC comprises a VL region and a CL region. In certain instances, the set of constructs can be co-expressed such that the HC is limiting. The set of constructs is co-expressed in either whole cells or in a cell-free expression system. In the case where the set of constructs is co-expressed in whole cells, as indicated above, it is assumed that heavy chain products are not secreted from the cell unless they are paired with a light chain. In this embodiment, each of the heavy and light chains is uniquely tagged. In step 1, HC1-LC and HC2-LC paired populations (heavy chain-paired polypeptide products) are separately isolated by affinity purification. In step 2, HC-LC 1 and HC-LC2 populations are quantified for each distinct HC1 or HC2 population. It is contemplated that depending on the detection method used, steps 1 and 2 can be combined.

Figure 8:
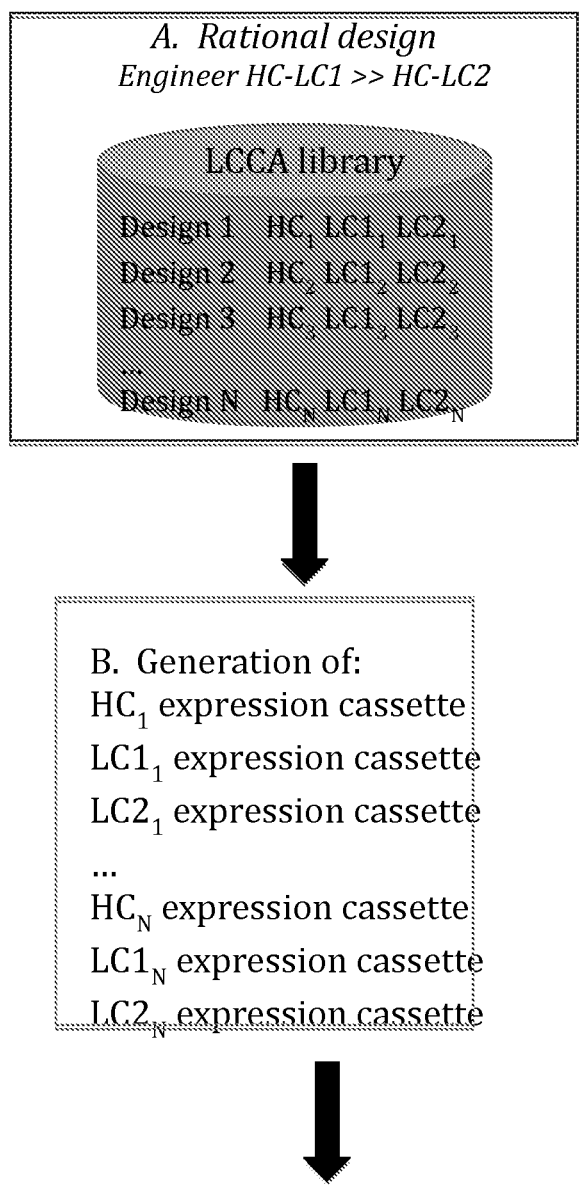
FIGS. 8A-F represent an exemplary rational design of a working LCCA library. Firstly, an in silico 'LCCA library' of designs (i.e., Design 1 . . . Design N) is created (FIG. 8A); the library being engineered such that HC preferentially pairs with LC1 and not LC2 (i.e., HC-LC1>>HC-LC2). These designs are then tested in vitro. To this end, library designs are individually cloned into expression vectors (see step 2.

The various embodiments of the method described herein can, in one embodiment, be used to develop a working LCCA library, as shown in FIG. 8. Briefly, FIG. 8 illustrates steps in an exemplary rational design of a working LCCA library. Firstly, an in silico 'LCCA library' of designs (i.e., Design 1 . . . Design N) is created (FIG. 8A); the library being engineered such that HC preferentially pairs with LC1 and not LC2 (i.e., HC-LC1>>HC-LC2). These designs are then tested in vitro. To this end, library designs are individually cloned into expression vectors (see step 2; FIG. 8B) as described elsewhere herein and using cloning methods known in the art. Kits for cloning are also commercially available from, for example, Life Technologies, and are contemplated for use herein. Next, LCCA designs (e.g., $HC_1$, $LC1_1$, and $LC2_1$ . . . $HC_N$, $LC1_N$, and $LC2_N$) are transiently expressed in mammalian cells (e.g., Chinese Hamster Ovary (CHO) cells; see step 3; FIG. 8C). Seven days post-transfection, CHO cell supernatants are harvested and HC-LC1:HC-LC2 populations are quantified for each LCCA design using an SPR readout as described elsewhere herein (step 4; FIG. 8D). Working designs are than ranked based on set criteria (e.g., HC-LC1:HC-LC2>=75:25); successful designs than become part of the 'Working LCCA library'. When dealing with large data sets, an optional data-mining step (#5; FIG. 8E) is available. During this step, a 'global analysis of HC-LC pairing results' may be optionally carried out. This step can be quite informative, since it potentially allows non-trivial and non-obvious patterns/trends in the data to be recognized. Finally, a working LCCA library is compiled (FIG. 8F).

Analysis of Results

There are several methods by which the results may be analyzed. The methods described below represent non-limiting examples of analysis and the embodiments of the present application are not intended to be restricted to following description.

In certain embodiments, the measured mass of immunoglobulin construct with a particular light-chain detectable moiety is normalized by the amount of the isolated heavy chain fraction. The equivalent mass ratio is evaluated for the corresponding control sample (see above). The ratio of these two mass ratios is equal to the percentage of isolated immunoglobulin construct with the particular recognition moiety. The same calculation is repeated for the other light chain tags. The percentages thus obtained for a given variant reflect the specificity of the pairing of one light chain (L1) to the heavy chain (H1) over the other light chain (L2) to the heavy chain (H1). denoted $p^{H1-L1}$ and $p^{H1-L2}$.

In some embodiments, recognizing unique and selective pairs of heavy and light chain sets, such as HC1:LC1 and HC2:LC2 set of pair where in the cross pairing of the chain to form HC1:LC2 or HC2:LC1 is avoided, is useful for design and synthesis of a biparatopic antibody construct. In some embodiments, the biparatopic construct is a bispecific construct. In an embodiment, the Fab derived by the pairing of HC1:LC1 can target antigen A while the Fab derived by pairing of HC2:LC2 can target antigen B. The identification of selectively forming pair of the heavy and light chain pairs allows for the coexpression of the two unique light chains LC1 and LC2 with a heterodimeric heavy chain pair to form bispecific antibodies.

Figure 13:
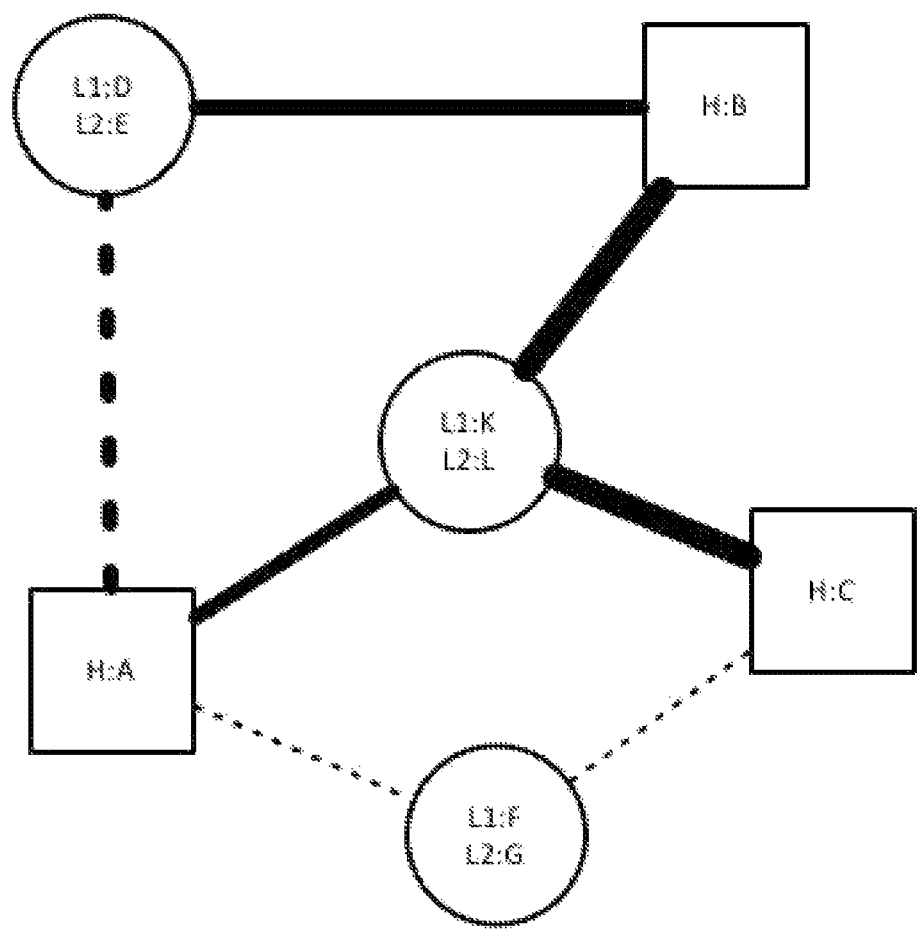
FIG. 13 depicts part of a graph to represent the light-chain competition assay data.

The pairing specificity data derived for a number of pairs of heavy and light chain pairs can be analyzed graphically and using different data mining techniques. For example, FIG. 13 depicts part of a bipartite graph to represent the light-chain competition assay data. Each square node represents a particular heavy-chain variant. Each circular node represents a particular pair of light-chain variants. Two such nodes connected with an edge represents one experiment of the light-chain competition assay.

The styling of the edge is a function of the outcome of the experiment. A solid black line means that the heavy-chain has a higher propensity to pair with the first of the two light-chain variants in the corresponding node. A dashed line means that the heavy-chain has a higher propensity to pair with the second of the two light-chain variants in the corresponding node. The width of the node is determined by the absolute value of S, defined above, $$W = |S| = \left| \log \frac{P1}{P2} \right|$$

where the measured percentages of the competing species have been measured by the light-chain competition assay. The greater the difference between the two percentages, the greater the width of the edge will be.

The part of the graph that contains a circular node to which, on the one hand a thick solid edge is attached and one the other hand a thick dashed edge is attached represent a combination of heavy and light-chain variants that are likely to form the desired product as they are co-expressed. The subgraph of such nodes is easily extracted and visually easy to recognize. In addition, variants that are highly promiscuous are readily identified, because they are associated with multiple thick edges of one type. For example, in FIG. 13 the node containing the light-chain variants K and L represents a pair of light-chains that in all assays have produced a preferentially pairing of chain K with the heavy-chains. This can for example be caused by poor properties of chain L or exceptionally good properties of chain K. When the number of data points becomes very large, the graphical representation allows rapid identification of outlier data and exploration of common design elements for assays with either good or poor properties.

One aspect provides a method of visualizing selective pairing of heavy chain polypeptides and light chain polypeptides. The method comprise, on a computer system including one or more processors and memory storing one or more programs, executed by the one or more processors to perform the method, performing the following steps. Competition assay data is obtained. The competition assay data comprises a plurality of binding assays. Each respective binding assay in the plurality of binding assays comprising exposing, in solution, a first amount of one or more corresponding heavy chain polypeptides, selected from a plurality of heavy chain polypeptide constructs, to a second amount of one or more corresponding light chain polypeptides, selected from a plurality of light chain polypeptide constructs, under conditions that limit either the corresponding one or more heavy chain polypeptides or the corresponding one or more light chain polypeptides in solution. When the corresponding one or more heavy chain polypeptides is limiting, the one or more heavy chain polypeptides consists of a single heavy chain polypeptide construct and the one or more light chain polypeptides consists of a plurality of light chain polypeptide constructs. When the corresponding one or more light chain polypeptides is limiting, the one or more light chain polypeptides consists of a single light chain polypeptide construct and the one or more heavy chain polypeptides consists of a plurality of heavy chain polypeptide constructs.

In the method, a graph is constructed comprising a plurality of nodes. The plurality of nodes comprises a first subset of nodes and a second subset of nodes. Each respective node in the first subset of nodes is displayed in a first graphical format and uniquely represents one or more corresponding heavy chain polypeptides in one or more binding assays in the plurality of binding assays. Each respective node in the second subset of nodes is displayed in a second graphical format and uniquely represents one or more corresponding light chain polypeptides in one or more binding assays in the plurality of binding assays. The first subset of nodes collectively represents all of the heavy chain polypeptides used in the plurality of binding assays. The second subset of nodes collectively represents all of the light chain polypeptides used in the plurality of binding assays.

In the method, the graph is populated with a plurality of edges. Each respective edge in the plurality of edges represents a corresponding binding assay in the plurality of binding assays and connects a first node in the first subset of nodes representing the one or more heavy chain polypeptides in the corresponding binding assay to a second node in the second subset of nodes representing the one or more light chain polypeptides in the corresponding binding assay. A first graphic style of each edge in the plurality of edges indicates whether the limiting polypeptide in the corresponding binding assay has a preference for one of the non-limiting polypeptides in the corresponding binding assay.

In some embodiments a second graphic style of each edge in the plurality of edges is determined by an amount that the limiting polypeptide in the corresponding binding assay has a preference for one of the non-limiting polypeptides in the corresponding binding assay. In some embodiments, the first graphic style is a line stipple and the second graphic style is a line width. In some embodiments, the line width of an edge in the plurality of edges is determined by the amount by which the limiting polypeptide in the corresponding binding assay has a preference for one of the non-limiting polypeptides in the corresponding binding assay, where the greater the amount that the limiting polypeptide in the corresponding binding assay has a preference for one of the non-limiting polypeptides in the corresponding binding assay, the greater the line width of the edge.

In some embodiments, the first graphical format is a first two-dimensional closed-form shape and the second graphical format is a second two-dimensional closed-form shape other than the first two-dimensional closed-form shape. In some embodiments the first graphical format is a first two-dimensional geographic shape and the second graphical format is a second two-dimensional geographic shape other than the first two-dimensional geographic shape. For instance, in some embodiments, the first two-dimensional geographic shape or the second two-dimensional geographic shape is selected from the group consisting of an n-gon, where n is an integer of 3 or greater, a circle, or an oval.

In some embodiments, the corresponding one or more heavy chain polypeptides in each binding assay in the plurality of binding assays consists of a single heavy chain polypeptide construct comprising a VH region and a CH1 region. Further, the one or more light chain polypeptides in each binding assay in the plurality of binding assays consists of a first light chain polypeptide construct and a second light chain polypeptide construct, where the first light chain polypeptide construct consists of a first VL region and a first CL region, and the second light chain polypeptide construct comprises a second VL region and a second CL region. In such embodiments, a line width (W) of each edge in the plurality of edges is determined by an amount that the single heavy chain polypeptide construct in the corresponding binding assay has a preference for the first light chain polypeptide construct or the second light chain polypeptide construct. This amount is determined by the formula:

$$W = \left| f\left(\frac{P1}{P2}\right) \right|$$

where, f is a linear or non-linear function, P1 is the amount of the single heavy chain polypeptide construct paired to the first light chain polypeptide construct normalized by the combination of (i) the amount of the single heavy chain polypeptide construct paired to the first light chain polypeptide construct and (ii) the amount of the single heavy chain polypeptide construct paired to the second light chain polypeptide construct, and P2 is the amount of the single heavy chain polypeptide construct paired to the second light chain polypeptide construct normalized by the combined amounts of (i) the amount of the single heavy chain polypeptide construct paired to the first light chain polypeptide construct and (ii) the amount of the single heavy chain polypeptide construct paired to the second light chain polypeptide construct.

In some such embodiments, f is a logarithmic or exponential function. In some such embodiments, when the single heavy chain polypeptide construct preferentially binds to the first light chain polypeptide construct the first graphic style is a solid line, and when the single heavy chain polypeptide construct preferentially binds to the second light chain polypeptide construct the first graphic style is a dashed line.

In some embodiments, the corresponding one or more heavy chain polypeptides in each binding assay in the plurality of binding assays consists of a first heavy chain polypeptide construct comprising a first VH and a first CH1 region and a second heavy chain polypeptide construct comprising a second VH and a second CH1 region. In such embodiments, the one or more light chain polypeptides in each binding assay in the plurality of binding assays consists of a light chain polypeptide construct, where the light chain polypeptide construct comprises a VL and a CL region. In some such embodiments, a line width (W) of each edge in the plurality of edges is determined by an amount that the single light chain polypeptide construct in the corresponding binding assay has a preference for the first heavy chain polypeptide construct or the second heavy chain polypeptide construct, where the amount is determined by the formula:

$$W = \left| f\left(\frac{P1}{P2}\right) \right|$$

where, f is a linear or non-linear function, P1 is the amount of the single light chain polypeptide construct paired to the first heavy chain polypeptide construct normalized by the combination of (i) the amount of the single light chain polypeptide construct paired to the first heavy chain polypeptide construct and (ii) the amount of the single light chain polypeptide construct paired to the second heavy chain polypeptide construct, and P2 is the amount of the single light chain polypeptide construct paired to the second heavy chain polypeptide construct normalized by the combined amounts of (i) the amount of the single light chain polypeptide construct paired to the first heavy chain polypeptide construct and (ii) the amount of the single light chain polypeptide construct paired to the second heavy chain polypeptide construct.

In some such embodiments, f is a logarithmic or exponential function. In some such embodiments, when the single light chain polypeptide construct preferentially binds to the first heavy chain polypeptide construct the first graphic style is a solid line, and when the single light chain polypeptide construct preferentially binds to the second heavy chain polypeptide construct the first graphic style is a dashed line. In some such embodiments, In some embodiments, the corresponding one or more heavy chain polypeptides in each binding assay in the plurality of binding assays consists of a single heavy chain polypeptide construct comprising a VH region, a CH1 region, a CH2 region, and a CH3 region. Moreover, the one or more light chain polypeptides in each binding assay in the plurality of binding assays consists of a first light chain polypeptide construct and a second light chain polypeptide construct, wherein the first light chain polypeptide construct comprises a first VL and a first CL region, and the second light chain polypeptide construct comprises a second VL and a second CL region. In some such embodiments, each binding assay in the plurality of binding assays further comprises an additional molecular entity consisting of a CH2 region and a CH3 region in the solution. In some such embodiments, a line width (W) of each edge in the plurality of edges is determined by an amount that the single heavy chain polypeptide construct in the corresponding binding assay has a preference for the first light chain polypeptide construct or the second light chain polypeptide construct, where the amount is determined by the formula:

$$W = \left| f\left(\frac{P1}{P2}\right) \right|$$

where, f is a linear or non-linear function, P1 is the amount of the single heavy chain polypeptide construct paired to the first light chain polypeptide construct normalized by the combination of (i) the amount of the single heavy chain polypeptide construct paired to the first light chain polypeptide construct and (ii) the amount of the single heavy chain polypeptide construct paired to the second light chain polypeptide construct, and P2 is the amount of the single heavy chain polypeptide construct paired to the second light chain polypeptide construct normalized by the combined amounts of (i) the amount of the single heavy chain polypeptide construct paired to the first light chain polypeptide construct and (ii) the amount of the single heavy chain polypeptide construct paired to the second light chain polypeptide construct.

In some such embodiments, f is a logarithmic or exponential function. In some such embodiments, when the single heavy chain polypeptide construct preferentially binds to the first light chain polypeptide construct the first graphic style is a solid line, and when the single heavy chain polypeptide construct preferentially binds to the second light chain polypeptide construct the first graphic style is a dashed line.

In some embodiments, the exposing in a binding assay in the plurality of binding assays is performed by co-expression of the one or more corresponding heavy chain polypeptides and the one or more corresponding light chain polypeptides.

High-Throughput

High-throughput as used herein refers to large scale and/or rapid performance of the methods and assays described herein. In certain embodiments, the systems described herein are suitable for high throughput screening of selective pairing of heavy chain polypeptides and light chain polypeptides. In certain embodiments, the devices useful in methods and assays described herein are capable of processing at least 50 different selective heavy chain-light chain pairs per week. In some embodiments, the devices useful in methods or assays described herein are capable of processing up to 500 different selective heavy chain-light chain pairs per week. Also provided are devices capable of processing at least 50, 100, 150, 200, 250, 300, 350, 400, 450, 500, 600, 700, 800, or 1000 different selective heavy chain-light chain pairs per week.

In certain embodiments are provided methods and assays with high throughput. In some cases, a method or assay described herein is useful for screening at least 50 different selective pairs per week per device. In some cases, a method or assay described herein is useful for screening at least 100 different selective pairs per week per device. In some cases, a method or assay is useful for screening at least 150 different selective pairs per week per device. In some cases, a method or assay is useful for screening at least 200 different selective pairs per week per device. Some methods described herein are useful for screening at least 300 different selective pairs per week per device.

The high-throughput methods, assays and systems described herein are robust. In certain embodiments, the methods, assays and systems described herein tolerate variable flow-rates. In certain embodiments, the methods and assays described herein tolerate a 5% change in flow rate. In some embodiments, methods and assays tolerate a 10% change in flow rate. In some embodiments are methods and systems that tolerate a 15% change in flow rate. Provided also are methods and assays that tolerate a 20% change in flow rate. Also provided are methods and assays that tolerate a 25% change in flow rate.

Provided are assays that can measure the effects of small variations in the protein sequences. Promiscuous protein-protein; domain-domain; chain-chain, interactions over large surface areas usually require multiple mutations (swaps) in order to introduce selectivity. In some embodiments, methods described herein do not require isolation or further purification of antibody constructs, thereby enabling more efficient screening. The assays described herein are sensitive, that is, the assay can detect, for example, HC:LC pairs with a sensitivity that can be as low as, in certain instances, femtograms/well.

Systems and Kits:

Provided are systems and kits for carrying out the methods described herein. In some embodiments are kits comprising a device for high-throughput screening of selective binding of heavy chain and light chain polypeptides. In some embodiments, the kit comprises reagents useful for the assays described herein. In some embodiments, the reagents are lyophilized. In some embodiments are kits and systems providing expression systems for the heavy chain and light chain polypeptides described herein.

Provided is a system for high-throughput screening of selective pairing of a heavy chain polypeptide with at least one light chain polypeptide comprising: one or more host cell to express: a heavy chain polypeptide comprising an immunoglobulin heavy chain region and a tag which is capable of being captured by a device comprising an interactive surface layer; a first light chain polypeptide comprising a first immunoglobulin light chain region; and at least one second light chain polypeptide comprising a second immunoglobulin light chain region; wherein said heavy chain polypeptide and said light chain polypeptides are expressed in a pre-determined ratio such that the amount heavy chain polypeptide is limiting; and wherein said first and second light chain polypeptide are tagged with a detectable moiety; and a detection device comprising an interactive surface layer capable of capturing said heavy chain polypeptide, wherein said device is further capable of detecting of the detectable moiety on each said light chain polypeptide; wherein constructs comprising the heavy chain polypeptide and said first or second light chain polypeptide are expressed by said one or more host cells, and contacted with said detection device, and wherein said detection device is useful to detect the amount of a first construct comprising the heavy chain polypeptide and first light chain polypeptide, and the amount of second construct comprising the heavy chain polypeptide and second light chain polypeptide, such that a greater amount of the first construct as compared to the second construct demonstrates a higher selectivity of the heavy chain polypeptide for pairing with the first light chain polypeptide, as compared to the second light chain polypeptide.

EXAMPLES

The examples below are given so as to illustrate the practice of this invention. They are not intended to limit or define the entire scope of this invention.

Example 1

Light Chain Competition Assay (LCCA)

FIG. 1 illustrates a high level schematic overview of the engineering requirements for forming a bispecific Mab (monoclonal antibody), and the assay requirements needed to quantify heavy chain light chain pairs. The design goal of engineering a bispecific Mab with high purity (i.e., little or no mispaired H-L associations) can be achieved by rationally engineering (via the introduction of specific amino acid mutations) the preferential pairing of two unique heavy chains for their unique cognate light chains. This process is shown schematically; here H1 has been engineered to preferentially pair with L1 and not L2. Likewise, H2 has been engineered to preferentially pair with L2 and not L1. The experimental screening of bispecific Mab designs requires an assay capable of simultaneously quantifying H1−L1:H1−L2 and H2−L2:H2−L1. These assay requirements can be simplified by assuming that each bispecific Fab arm can be independently engineered. In this case, the assay would only need to quantify H1-L1:H1-L2 or H2-L2:H2-L1, and not both simultaneously.

Figure 2:
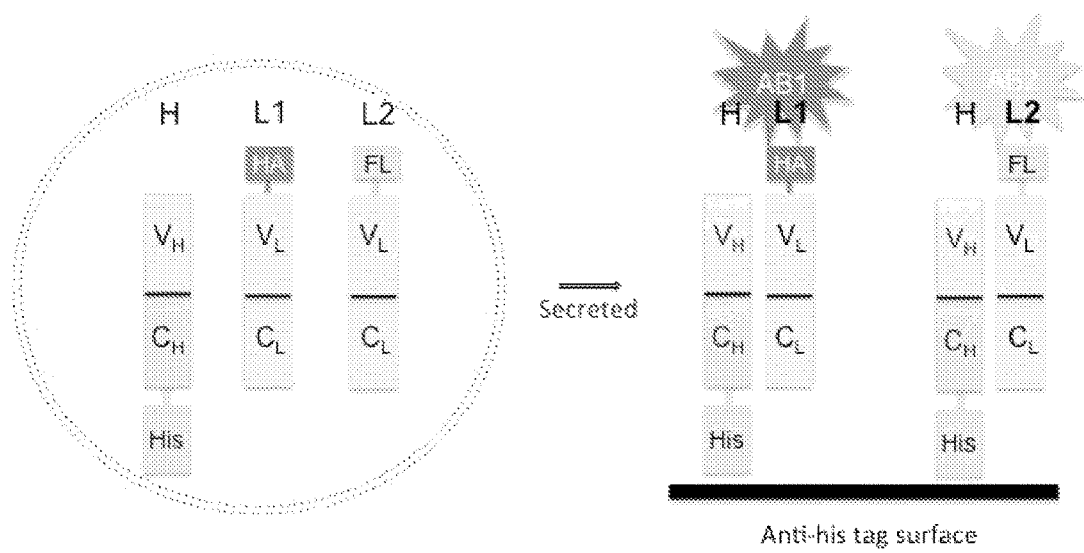
FIG. 2 provides a schematic description of the key steps of the assay using SPR readout of light chain tagged populations.

The following protocol provides a description of key steps of the assay using SPR read out of light chain tagged populations. FIG. 2 illustrates an exemplary whole Cell Expression: Light Chain Competition Assay:

Light chain competition assay:

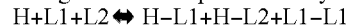

H+L1+L2 ↔ H−L1+H−L2+L1−L1

HC Limiting: HC limiting. H:L1:L2=1:1:1. Light chains compete for heavy chain

No H-L disulphide bonds were observed in initial variants.

The Light Chain Competition Assay quantifies the relative pairing of one heavy chain for at least two unique light chains. The assay and the preceding steps can be summarized as follows: 1. Concomitant expression of heavy and light chains, with the heavy chain being in limiting amounts (e.g., HC:LC1:LC2=1:1:1), 2. Isolation of HC-LC complexes—achieved by binding heavy chains to the SPR chip via a his-tag pull-down, and 3) Quantification of relative HC-LC populations (i.e., H1−L1:H1−L2). In the SPR format, antibodies specific for unique light chain-tagged populations are used for the quantification. Note: This assay can be carried with or without the H-L disulphide.

Figure 3A:
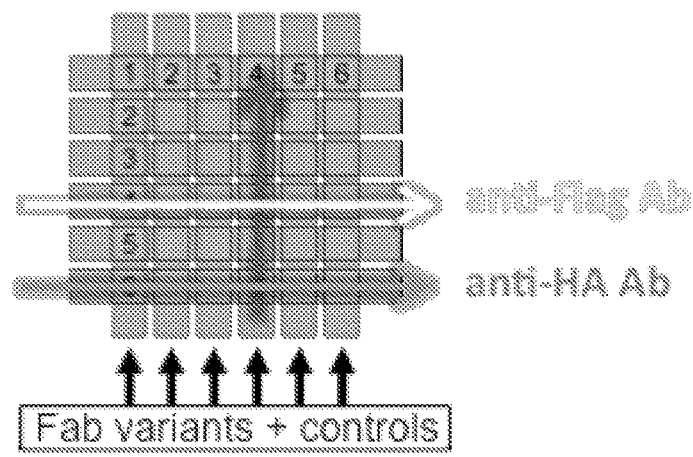
FIGS. 3A and 3B illustrate an exemplary light chain competition assay where
Figure 3B:
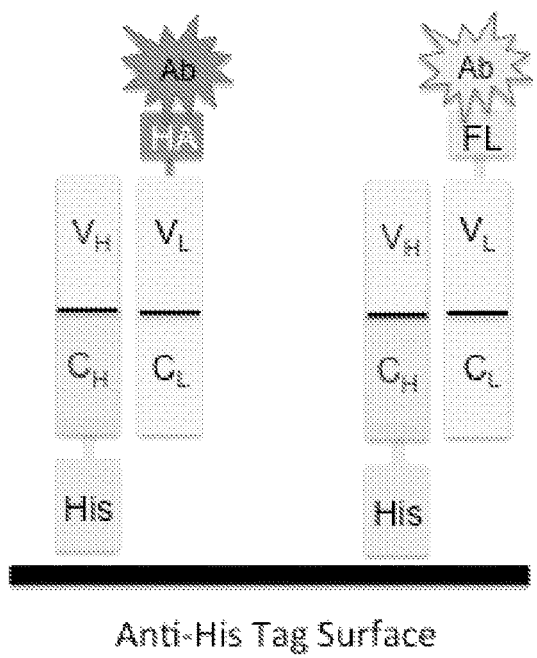

FIGS. 3A and 3B provide an example of a schematic description of how the assay would be set up on an SPR chip, and in addition, a method of how the percentages of each light chain tagged population is calculated.

A SPR Sandwich-Based Assay (FIG. 3A) is utilized in which:

1. Capture Fab (His-tag capture)—Quantify
2. Capture control Fabs (WT HC+100% WT FLAG-LC or 100% WT HA-LC)—Quantify
3. Capture anti-Tag Ab—Quantify
4. Normalize anti-Tag Ab capture per 100 RUs bound Fab
*Calculate anti-Tag Fab population (%)
*Calculation:
1. (Norm. anti-Flag Ab RU/Norm. anti-FLAG Ab RU [control])×100=% anti-FLAG Fab.
2. (Norm. anti-HA Ab RU/Norm. anti-FLAG Ab RU (control))×100=% anti-HA Fab.

In FIG. 3A a schematic of the ProteOn XPR36 chip is shown. Each chip is composed of a 6×6 grid of cells, with each cell being able to monitor a binding reaction. For the LCCA, variants and controls are injected in a vertical direction across the chip and are bound to the chip via an anti-his tag Ab (see FIG. 3B and Example 5 for more detail). After a washing step, anti-LC tag Abs are injected (in separate cells) horizontally across the chip. The amount of each anti-LC tag Ab captured, relative to appropriate Fab controls (with 100% LC1 or LC2 only), allows relative populations of HC-LC1 and HC-LC2 to be calculated for each variant. The steps required to calculate the aforementioned populations are shown above with respect to the calculations.

Figure 4:
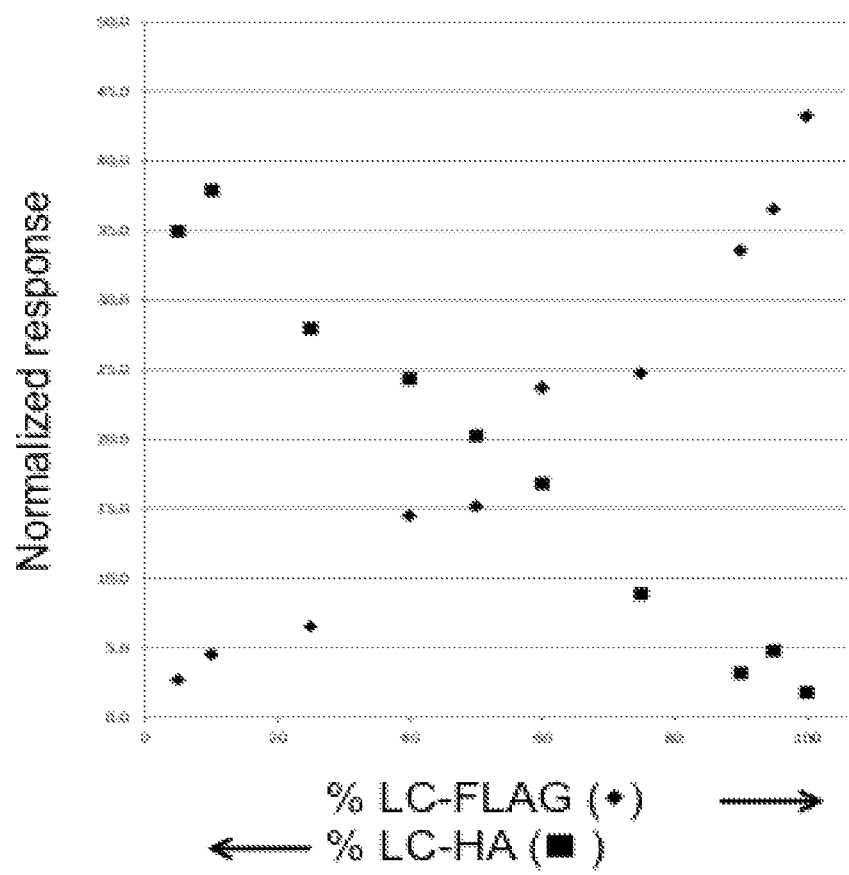
FIG. 4 depicts a plot of a doping experiment whereby known ratios of 100% HC: LC-HA or 100% HC: LC-FLAG are mixed in predetermined ratios. The readout of the anti-tag antibody is approximately linear when plotted against the ratio of LC-FLAG or LC-HA.

FIG. 4 illustrates a plot of a doping experiment whereby known ratios of 100% HC:HA-LC or 100% HC:FLAG-LC are mixed in predetermined ratios. Purified HC:HA-LC and HC:FLAG-LC are mixed in known ratios. A Fab mixture is loaded onto a SPR chip and the signal is read off for HA and FLAG. The readout of the anti-tag antibody is approximately linear when plotted against the ratio of LC-FLAG or LC-HA. The linear nature of the signal versus LC populations provides a straightforward means for quantifying HC-LC1:HC-LC2 populations.

Example 2

Theory of the Light-Chain Competition Assay

Reaction Definitions and Equilibrium Behavior

The co-expression of one heavy-chain, H, and two light-chains L1 and L2, the following reactions are possible:

$H+L1 \leftrightarrow HL1$
$H+L2 \leftrightarrow HL2$
$L1+L2 \leftrightarrow L1L2$
$L1+L1 \leftrightarrow L1L1$
$L2+L2 \leftrightarrow L2L2$
$H+H \leftrightarrow HH$ To each of these reactions an association and dissociation rate constant exist, where we expect the latter reaction to be slower than the former.

The desired property to assay is the relative propensity for L1 to pair with H against L2 to pair with H. A design that produces high relative amount of HL1 species over HL2 species is a design with the desirable properties. The central quantities are therefore the following ratios:

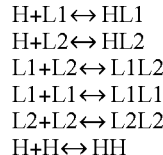

$$R = \frac{[HL1]}{[HL2]}$$

$$S = \log\frac{[HL1]}{[HL2]}$$

$$P1 = 100 \cdot \frac{[HL1]}{[HL1]+[HL2]}$$

$$P2 = 100 \cdot \frac{[HL2]}{[HL1]+[HL2]}$$

R is the ratio of the amount of the two Fab species. S is the logarithm of R, and is proportional to the free energy difference between the pairing of L1 with H and L2 with H. P1 and P2 are the percentages of the desired and undesired species, respectively. From this formulation it follows that:

$$S = \log\frac{P1}{P2}$$

In order to make the ratios defined above represent the physical property of interest of a given design, the amount of L1 and L2 in the expression have to be in excess relative to the amount of H. Under such conditions, the pairing becomes a competition and the amount of HL1 relative to the amount of HL2 is expected to reflect the relative fitness or compatibility of L1 pairing with H and L2 pairing with H, respectively.

In order to understand how to interpret the experimental output, the ratios above are computed theoretically by assigning different values to the association and dissociation rate constants and solving the chemical kinetics problem thus defined. To solve the problem we assume that steady-state reaction kinetics holds. This implies that only the ratio between the association and dissociation rate constants, in other words the equilibrium constant, matters for the amount of the species that is formed.

First, assume all reactions have zero probability except the first two forming a Fab. The relation between relative amount of HL1 and HL2 as a function of relative amount of L1 and L2 in the co-expression is computed and shown in FIG. 5. The relation is simple and the intersection with the vertical axis is equal to the logarithm of the ratio of the pairing propensities. An alternative way to display the data is to transform the relations to percentage L1 on the x-axis and percentage HL1 on the y-axis. This relation is shown in FIG. 6, where the same pairing propensity ratios have been used as in FIG. 5. As can be seen, the trends look different, in particular the greater the difference in pairing propensity, the more amount HL1 is obtained for the same amount of L1, and all curves approach the same point in the lower and upper limit.

Under the condition that light-chain dimers also form with non-zero probability, the dose-scaling curves change slightly. For example, it can be shown that if the pairing propensity to form light-chain dimer is equal for L1 and L2, the slope is reduced, but the qualitative trend is preserved.

Example 3

Analysis of the Setup of LCCA

Figure 7:
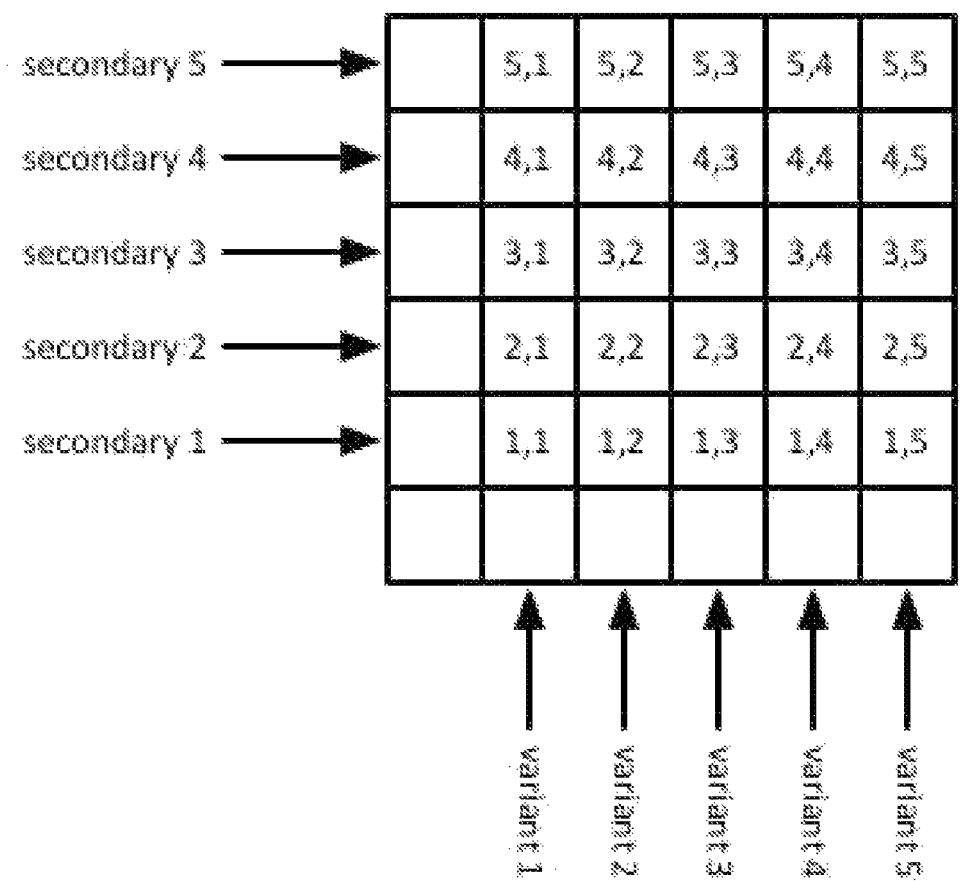
FIG. 7 depicts a schematic representation of a SPR chip typically used in the LCCA, where five variants are run concurrently and as many as five different secondary antibodies can be used. Each cell is denoted by a two element coordinate as shown.

As described elsewhere, in the LCCA the mixture of differently tagged HL1 and HL2 is initially captured on a chip followed by a quantification of the two Fab species by conversion of amount of captured secondary anti-tag antibody to an optical signal. A typical SPR chip is illustrated in FIG. 7, and the labels used for the cells in the analysis below are introduced as well.

In sequence, the following steps are taken to perform the LCCA: (1) The material excreted from the cell that has been transfected with the variant DNAs is flowed from the entry at the bottom of the chip to the top in the illustration in FIG. 7. As this is done the horizontal channels are closed. (2) The vertical channels are closed. (3) The mass of material loaded onto each cell is evaluated in units RUs. (4) The horizontal channels are opened. (5) The various secondary antibodies, such as anti-HA, anti-FLAG and the soluble antigen of the Fab are flowed from the entry at the left to the right in the illustration in FIG. 7. The addition of mass is evaluated in units RUs.

Let $n_{v1}^{Fab}$ denote the total amount of Fab in the material excreted from the cell of variant v1. Let $\rho^{Fab}$ denote conversion factor between the number of Fabs and the mass of Fab. Within the accuracy of the experiment all Fabs have the same conversion factor. Let $d\hat{\ }i\_vertical$ denote the factor that quantifies how much the concentration of molecules differs between the i:th row and the concentration in the source solution along the vertical flow in FIG. 7. If the flow over the SPR chip is fully equilibrated this factor is unity for all cells. The following relation thus holds:

$$m_{i,j}^{v1,Fab} = d_{vertical}^i \cdot n_{v1}^{Fab} \cdot \rho_{Fab}$$

Let $r_{v1}^{HL1}$ denote the fraction of Fabs for variant v1 that is of species HL1. Let $r_{v1}^{HL2}$ denote the corresponding quantity for HL2.

For the horizontal flow similar quantities are introduced as for the vertical flow and the following relation is formulated:

$$m_{i,j}^{s1,v1} = d_{horizontal}^j \cdot n^{s1} \cdot \rho^{s1} \cdot d_{vertical}^i \cdot n_{v1}^{Fab} \cdot r_{v1}^{HL1}$$

where the following quantities have been introduced: $d_{horizontal}^j$ denotes the factor the quantifies how much the concentration of secondary antibody differ between cell j and the solution, which is inserted; $n^{s1}$ is the number of secondary antibodies, $\rho^{s1}$ the density of the secondary. The dependency on the amount of captured Fab derives from that the secondary only binds to the Fab. The arbitrary assignment that the secondary antibody s1 binds to the tag of HL1 has been made as well.

With SPR a signal directly proportional to the quantities $m_{i,j}^{v1,Fab}$ and $m_{i,j}^{s1,v1}$ are measured with a certain error that derives from imprecisions with the SPR machine. The machine error, $e(\sigma)$, is assumed to be normal distributed, centered at zero and of some standard deviation $\sigma$.

The ratio of the two masses is:

$$R_{s1}^{v1} = \frac{m_{i,j}^{s1,v1}}{m_{i,j}^{v1,Fab}} = \frac{d_{horizontal}^j \cdot n^{s1} \cdot \rho^{s1} \cdot r_{v1}^{HL1}}{\rho_{Fab}} + e(\sigma)/C$$

where it has been assumed the error is small enough to be neglected in the denominator; C is a constant.

A control sample is run where the amount of HL1 is known to be 100%, in other words $r_{v1}^{HL1}=1$. Denote the corresponding mass ratio as $R_{s1,100\%}$. The ratio of the mass ratios is therefore $$\frac{R_{s1}^{v1}}{R_{s1,100\%}} = \frac{d_{horizontal}^j}{d_{horizontal}^k} \cdot r_{v1}^{HL1} + e(\sigma)/C'$$

As long as the distribution of secondary antibody is nearly uniform along the horizontal dimension, the concentration of secondary antibody is nearly identical for the channel that contains the variant and the channel that contains the control, this ratio returns the quantity of interest, which is the fraction of HL1 for a given sample. Even if this assumption is not valid, but the control variant is always run in the same channel, the following relation is obtained:

$$\frac{R_{s1}^{v1}}{R_{s1,100\%}} \bigg/ \frac{R_{s2}^{v1}}{R_{s2,100\%}} = \frac{r_{v1}^{HL1}}{r_{v1}^{HL2}} + e(\sigma)/C''$$

Within the error of the experiment, the quantity on the right-hand side is equal to the fraction of the concentrations $$\frac{[HL1]}{[HL2]},$$

which hence enables the computation of the quantities described in the earlier section on the reaction definitions.

The reagents employed in the examples are commercially available or can be prepared using commercially available instrumentation, methods, or reagents known in the art. The foregoing examples illustrate various aspects of the invention and practice of the methods of the invention. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

Example 4

Preparation of Constructs Encoding D3H44 IGG Heavy Chains and D3H44 IGG Light Chains The heavy and light chains of the anti-tissue factor antibody D3H44 for use in the method described herein were prepared as follows. D3H44 Fab light (AJ308087.1) and heavy (AJ308086.1) chain sequences were obtained from GenBank (www.ncbi.nlm.nih.gov/genbank/). Co-expression sets comprising one heavy chain and two different light chains were designed in order to drive selective pairing of the heavy chain with one of the light chains by making at least one mutation in the Fab region of the heavy and light chain sequences.

The co-expression sets were gene synthesized and codon optimized for mammalian expression. Light chain vector inserts, consisting of 5'-EcoRI cut site—HLA-A signal peptide—HA or FLAG tag—Light chain clone—TGA stop—BamH1 cutsite-3', were ligated into a pTT5 vector (Durocher Y et al., *Nucl. Acids Res.* 2002; 30, No. 2 e9). The resulting vector+insert were sequenced to confirm correct reading frame and sequence of the coding DNA. Likewise, heavy chain vector inserts, consisting of 5'-EcoR1cutsite—HLA-A signal peptide—heavy chain clone—ABD2-His6tag—TGA stop—BamH1 cutsite-3', were ligated into a pTT5 vector (ABD; albumin binding domain). The resulting vector+insert were also sequenced to confirm correct reading frame and sequence of the coding DNA.

Example 5

Figure 5:
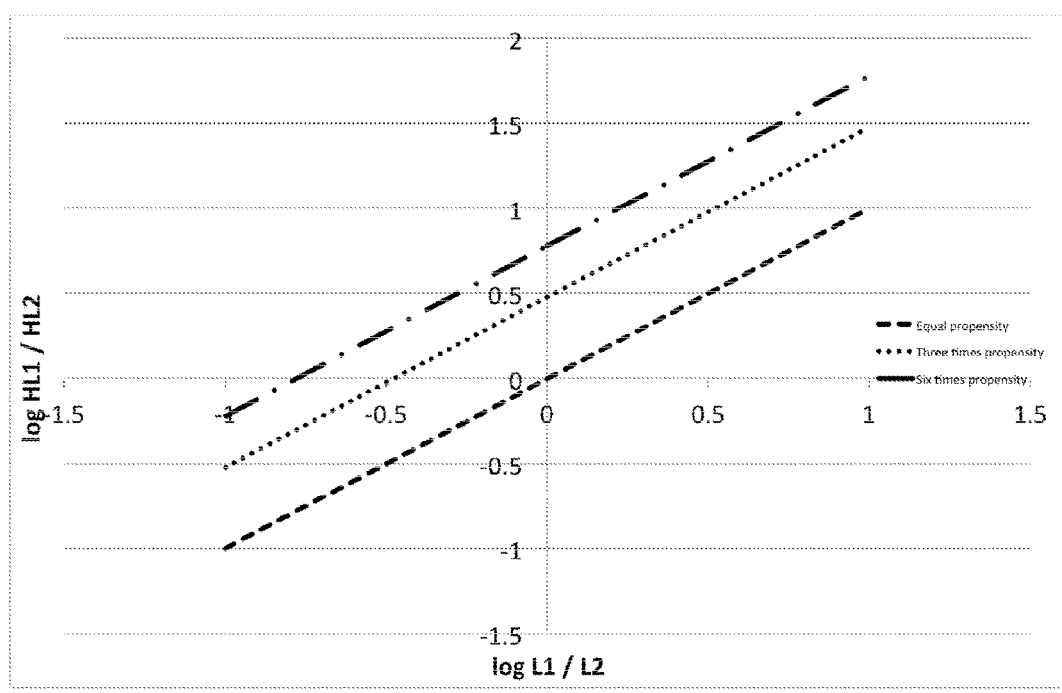
FIG. 5 shows theoretical dependency of relative amount of the two Fab species as a function of the relative amount of L1 and L2 in the co-expression. The relations for three different pairing propensities are shown.
Figure 6:
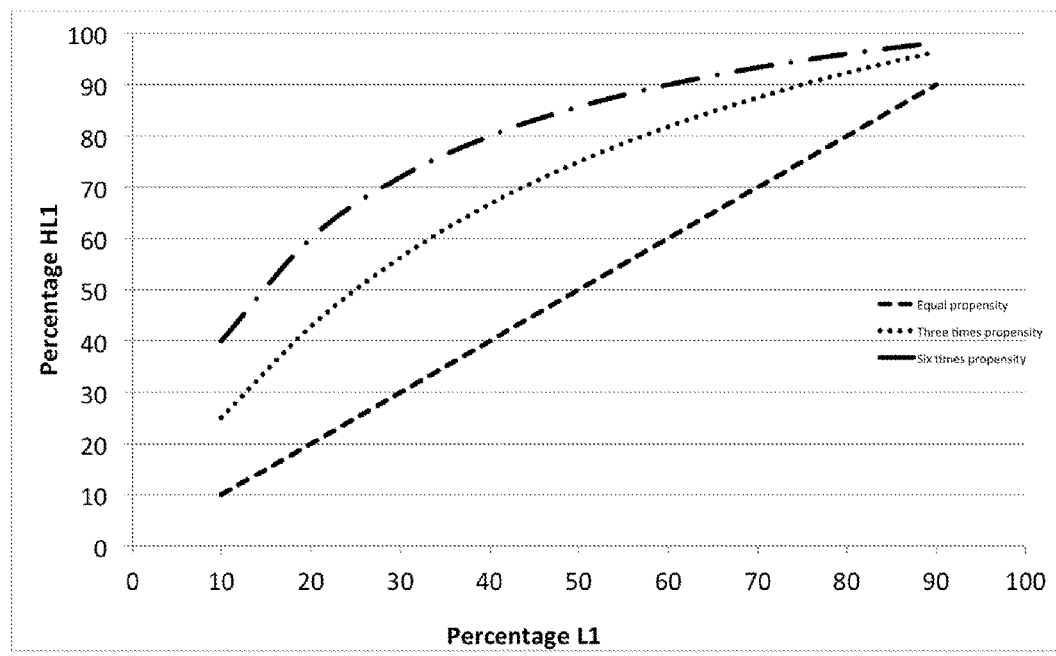
FIG. 6 shows theoretical dependency of relative amount of the two Fab species as a function of the relative amount of L1 and L2 in the co-expression. The relations for three different pairing propensities are shown.

Assessment of Preferential Pairing of Heterodimers in Co-Expression Sets Comprising Modifications in D3H44 IGG Light and/or Heavy Chains The ability of heterodimers to preferentially pair in co-expression sets comprising D3H44 heavy and light chains with modified Fab domains, prepared according to Example 4, was determined and the results are shown in FIG. 5. Fifteen co-expression sets, each comprising one D3H44 heavy chain construct co-expressed with two unique D3H44 light chain constructs and the relative light chain pairing specificity (e.g., H1_L1:H1_L2) were tested. A verification step may be optionally included in the methods in some instances to confirm that a hit is obtained and to provide an assessment for the robustness of the design. Heavy chain (HC) was kept in limiting quantities (i.e., HC<L1+L2) for both competition assay screens and verifications. The methods were carried out as follows.

Transfection Method

Co-expression sets comprising one heavy chain and two light chain constructs prepared as described in Example 4 were transfected into CHO-3E7 cells as follows. CHO-3E7 cells were cultured at 37° C. in FreeStyle™ F17 medium (Invitrogen cat #A-1383501) supplemented with 4 mM glutamine and 0.1% Pluronic F-68 (Invitrogen cat #24040-032). Two million cells (CHO-3E7) in 2 ml of growth medium were transfected with a total of 2 µg DNA using PEI-pro (Polyplus cat #115-010) at a DNA:PEI ratio of 1:2.5. Twenty-four hours after the addition of the DNA-PEI mixture, the cells were transferred to 32° C. Supernatants were tested for expression on day 7 by non-reducing SDS-PAGE analysis followed by Coommassie blue staining to visualize the bands. HC: LC ratios are as indicated in Table 2. Example HC:LC1:LC2 ratios used for LCCA screening and verification. Also provided, are the relative amounts of DNA used for transfecting each 2 ml CHO/HEK cell culture. Note: 'DNA quantity used for transfection' includes the vector, as well as the insert (e.g., HC.)

TABLE 2

| HC:L1:L2[#] ratio | Experiment | DNA quantity used for transfection (ng) | | | |
|---|---|---|---|---|---|
| | | HC | LC1 | LC2 | Stuffer[^] DNA |
| 50:50:50 | Competition assay screen | 333 | 333 | 333 | 1000 |
| 50:50:50 | Competition assay verification | 333 | 333 | 333 | 1000 |
| 50:40:60 | Competition assay verification | 333 | 266 | 400 | 1000 |
| 50:50:50 | Competition assay verification | 333 | 333 | 333 | 1000 |
| 50:60:40 | Competition assay verification | 333 | 400 | 266 | 1000 |

[#]HC: Heavy chain, L1: Light chain 1, L2: Light chain 2
[^]Stuffer DNA: $_p$TT5 vector without a DNA insert.

Competition Assay SPR Method

The degree of preferential D3H44 light chain pairing to D3H44 heavy chain in co-expression sets was assessed using an SPR-based readout of unique epitope tags located at the N-terminus of each light chain.

Surface Plasmon resonance (SPR) supplies. GLM sensorchips, the Biorad ProteOn amine coupling kit (1-ethyl-3-(3-dimethylaminopropyl) carbodiimide hydrochloride (EDC), N-hydroxysulfosuccinimide (sNHS) and ethanolamine), and 10 mM sodium acetate buffers were purchased from Bio-Rad Laboratories (Canada) Ltd. (Mississauga, ON). Recombinant Her-2 protein was purchased from eBioscience (San Diego, Calif.). 4-(2-hydroxyethyl)-1-piperazineethanesulfonic acid (HEPES) buffer, ethylenediaminetetraacetic acid (EDTA), and NaCl were purchased from from Sigma-Aldrich (Oakville, ON). 10% Tween 20 solution was purchased from Teknova (Hollister, Calif.).

SPR biosensor assays. All surface plasmon resonance assays were carried out using a BioRad ProteOn XPR36 instrument (Bio-Rad Laboratories (Canada) Ltd. (Mississauga, ON)) with PBST running buffer (PBS Teknova Inc with 0.05% Tween20) at a temperature of 25° C. The anti-penta His capture surface was generated using a GLM sensorchip activated by a 1:5 dilution of the standard Bio-Rad sNHS/EDC solutions injected for 140 s at 100 µL/min in the analyte (horizontal) direction. Immediately after the activation, a 25 µg/mL solution of anti-penta His antibody (Qiagen Inc.) in 10 mM NaOAc pH 4.5 was injected in the analyte (vertical) direction at a flow rate of 25 µL/min until approximately 3000 resonance units (RUs) were immobilized. Remaining active groups were quenched by a 140 s injection of 1M ethanolamine at 100 µL/min in the analyte direction, and this also ensures mock-activated interspots are created for blank referencing.

The screening of the heterodimers for binding to the anti-FLAG (Sigma Inc.) and anti-HA (Roche Inc.) monoclonal antibodies occurred in two steps: an indirect capture of the heterodimers onto the anti-penta His surface in the ligand direction followed by an anti-FLAG and anti-HA injection in the analyte direction. Firstly, one buffer injection for 30 s at 100 uL/min in the ligand direction was used to stabilize the baseline. For each heterodimer capture, unpurified heterodimers in cell-culture media were diluted to 4% in PBST. One to five heterodimers or controls (i.e., controls containing either 100% HA-light chain or 100% FLAG-light chain) were simultaneously injected in individual ligand channels for 240 s at flow 25 µL/min. This resulted in a saturating heterodimer capture of approximately 300 to 400 RUs onto the anti-penta His surface. The first ligand channel was left empty to use as a blank control if required. This heterodimer capture step was immediately followed by two buffer injections in the analyte direction to stabilize the baseline, and then 5 nM anti-FLAG and 5 nM anti-HA were each injected in duplicate at 50 µL/min for 120 s with a 180 s dissociation phase, resulting in a set of binding sensorgrams with a buffer reference for each of the captured heterodimer. Where possible, the antigen to which the heterodimer binds can also be injected over the last remaining analyte channel as an activity control. The heterodimers were regenerated by an 18 s pulse of 0.85% phosphoric acid for 18 s at 100 µL/min to prepare the anti-penta His surface for the next injection cycle. Sensorgrams were aligned and double-referenced using the buffer blank injection and interspots, and the resulting sensorgrams were analyzed using ProteOn Manager software v3.0.

Data obtained from the SPR was analyzed as described in Examples 2 and 3.

Processed data may be obtained from the SPR based assay as shown in Table 3. A selection of results of the light chain competition assay with H1 or H2+ both La and L2 are provided. Preferential H1–L1 and H2–L2 binding was achieved.

TABLE 3

| | Electrostatic/Steric-based designs | |
|---|---|---|
| | LCCA readout | |
| Design | H1-L1:H1-L2 (A:B) | H2-L2:H2-L1 (C:D) |
| WT | 50:50:00 | |
| 1 | 65.0:10.1 | 77.4:17.4 |
| 2 | 70.5:5.2 | 73.6:19.8 |
| 3 | 68.4:13.8 | 62.7:34.6 |
| 4 | 44.1:33.3 | 56.0:20.6 |
| 5 | 73.3:10.8 | 66.9:34.5 |
| 6 | 71.1:22.7 | 65.3:29.9 |
| 7 | 67.5:8.8 | 75.1:18.6 |
| 8 | 67.1:28.7 | 61.5:23.4 |
| 9 | 65.7:21.7 | 57.2:30.0 |
| 10 | 71.9:30.4 | 54.8:30.1 |
| 11 | 90.0:7.7 | 81.1:1.4 |
| 12 | 98.7:4.2 | 85.2:6.2 |
| 13 | 97.4:0.4 | 87.3:1.5 |
| 14 | 84.1:0.9 | 73.6:1.5 |
| 15 | 86.7:1.4 | 71.0:7.2 |

The total percentage of L1 and L2 should, theoretically, add up to 100%. In practice, it was observed for some variants that the total amount of L1 and L2 added up to significantly less than 100%. This discrepancy in total light chain percentage is believed to be due in part to the occurrence of variable non-specific binding during initial heterodimer capture on the SPR chip.

LCCA throughput on one ProteOn XPR36 machine is typically 60 variants per day, or 300 variants per week. It should be understood that an SPR machine may be run for 4 or 5 days per week. Further, a higher throughput screening rate could be achieved by increasing resources (e.g., using two ProteOn XPR36 machines) or by switching to a higher-throughput SPR machine.

Example 6

Results of Screening Assay are Predictive of Selective Pairing in a "Wild-Type Format"

LCCA results of a 'Fab pair design' (combination of working H1–L1 plus H2–L2 designs) show a positive correlation with the results obtained when the corresponding two full-length heavy chains are co-expressed with two unique light chain constructs (wild-type format). The assay to test pairing in the "wild-type format" was carried out as follows using two heavy chains that have mutations in the CH3 region, such that said heavy chain polypeptides preferentially heterodimerize with each other.

Two unique full-length heavy chain constructs were co-expressed with two unique light chain constructs, yielding ten possible antibody species: H1_L1:H1_L1, H1_L2: H1_L2, H1_L1:H1_L2, H2_L1:H2_L1, H2_L2:H2_L2, H2_L2:H2_L2, H1_L1:H2_L1, H1_L2:H2_L2, H1_L2: H2_L1 and H1_L1:H2_L2. The H1_L1:H2_L2 species is the correctly paired heterodimer. The relative pairing specificity in terms of amount of preferred species H1_L1:H2_L2 vs others was determined using LC-MS after protein A (pA) purification. The C terminal LYS was removed from the Heavy Chains to decrease the heterogeneity and the risk of confounding results from mass spectrometry. Whenever possible, no tags were included; when the difference in mass between any of the possible species in the mixture was below 50 Da, one or both light chains were designed with an N terminal HA tag fusion and/or FLAG tag fusion. Heavy chain (HC) was kept in limiting quantities (i.e., HC<L1+L2).

Figure 14:
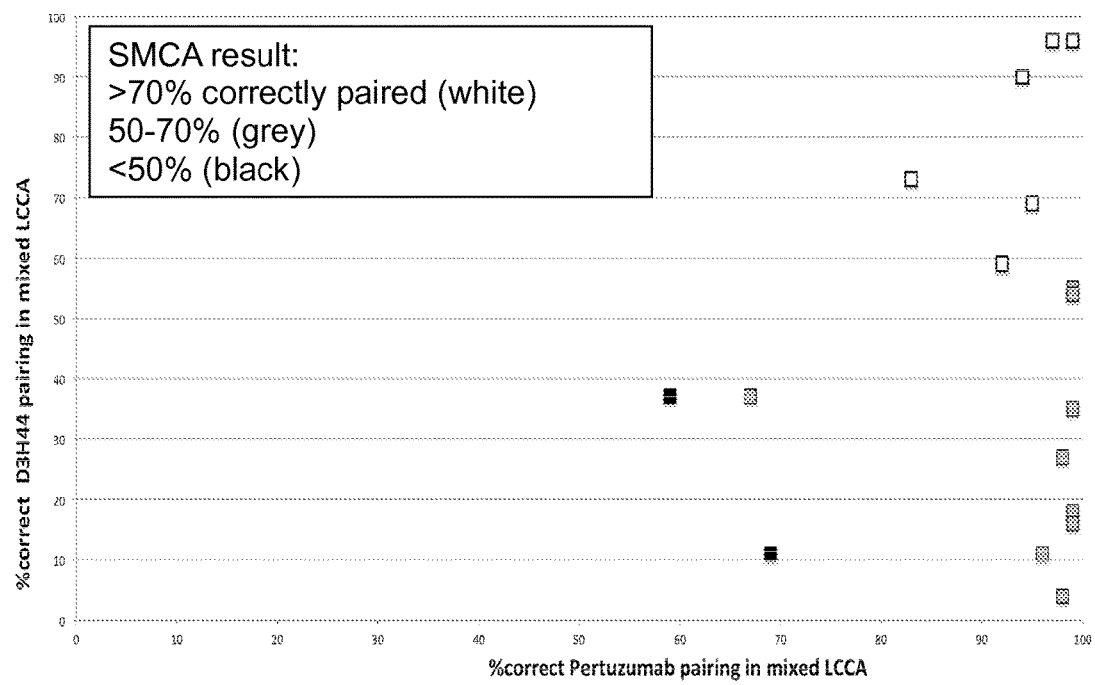
FIG. 14 shows LCCA Fab1 (i.e., HC1:LC1:LC2; x-axis) and Fab2 (i.e., HC2:LC1:LC2; y-axis) results for seventeen 'Fab pair designs'. Designs working well (i.e., showing a high percentage of correctly paired fabs) on both Fab arms can be seen in the top rightmost quadrant of the plot. Designs performing less effectively (e.g., one Fab arm is not working well) are shown on the bottom left of the plot. The Fab pair design's performance in the wild-type format is indicated by the data point's coloring (see legend).

FIG. 14 shows LCCA Fab1 (i.e., HC1:LC1:LC2; x-axis) and Fab2 (i.e., HC1:LC1:LC2; y-axis) results for seventeen 'Fab pair designs'. Designs working well (i.e., showing a high percentage of correctly paired fabs) on both Fab arms can be seen in the top rightmost quadrant of the plot. Designs performing less effectively (e.g., one Fab arm is not working well) are shown on the bottom left of the plot. The Fab pair design's performance in the wild-type format is indicated by the data point's coloring (see legend). A positive correlation can clearly be seen; a well performing LCCA Fab pair design translates well into the wild-type format (i.e., the percentage of correctly paired fabs is high). Likewise, a poorly working LCCA Fab pair design performs relatively poorly in the wild-type format. Note: Mixed LCCA results were obtained from mixtures of D3H44 and Pertuzumab. For example, a Fab1 LCCA would be Pertuzumab HC, Pertuzumab LC1 and D3H44 LC2.

All publications, patents and patent applications mentioned in this specification are herein incorporated by reference into the specification to the same extent as if each individual publication, patent or patent application was specifically and individually indicated to be incorporated herein by reference.

What is claimed:

1. A high-throughput method of quantifying selectivity of a heavy chain polypeptide for pairing with a light chain polypeptide comprising the steps of:
   (a) co-expressing from polynucleotides encoding heavy and light chain polypeptides a set of polypeptide constructs comprising:
      a first heavy chain polypeptide comprising a VH and a CH1 region;
      a first light chain polypeptide comprising a first VL and first CL region; and
      a second light chain polypeptide comprising a second VL and second CL region;
      wherein said heavy chain polypeptide and said light chain polypeptides are expressed such that the total amount of the heavy chain polypeptide is limiting; and wherein co-expressing the set of polypeptide constructs results in a set of polypeptide products;
   (b) isolating heavy chain-paired polypeptide products comprising the heavy chain polypeptide paired with said first or second light chain polypeptide from the set of polypeptide products; and
   (c) quantifying the amount of heavy chain polypeptide paired with said first light chain polypeptide (H1L1), and the amount of heavy chain polypeptide paired with said second light chain polypeptide (H2L2) in the heavy chain-paired polypeptide products to generate competition assay data;
   wherein a greater amount of the heavy chain polypeptide paired with one of said first or second light chain polypeptide as compared to the other light chain polypeptide indicates selectivity of the heavy chain polypeptide for pairing with said first or second light chain polypeptide.

2. The method of claim 1, wherein the first heavy chain polypeptide comprising a VH and CH1 region further comprises a CH3 region, or a CH2 region and a CH3 region.

3. The method of claim 1, wherein the first heavy chain polypeptide is in a Fab format.

4. The method of claim 1, wherein said heavy chain polypeptide, and first and second light chain polypeptides are expressed in a predetermined ratio of about 0.25:1, 1:1:1, 1:2:2, or 1:3:3.

5. The method of claim 3, wherein step (a) is in a host cell, or in an in vitro non-cell expression system.

6. The method of claim 3, further comprising the step of separating expressed polypeptides from an expression medium after expression.

7. The method of claim 6 wherein said expressed polypeptides are separated by centrifugation, or by use of a purification column.

8. The method of claim 3, further comprising the steps of:
   expressing said heavy chain polypeptide and one of said first and second light chain polypeptide in at least one host cell, in the absence of other light chain polypeptides;
   isolating heavy chain-paired polypeptide products comprising the heavy chain polypeptide and one of said first and second light chain polypeptide; and
   quantifying the amount of said heavy chain-paired polypeptide products, wherein said amount serves as a control standard for maximum detectable binding of said heavy chain polypeptide with one of said first and second light chain polypeptides.

9. The method of claim 8, wherein products that comprise the heavy chain polypeptide and the desired light chain polypeptide provide the positive control standard.

10. The method of claim 8, wherein products that comprise the heavy chain polypeptide and the less desired light chain polypeptide provide the negative control standard.

11. The method of claim 3, wherein at least one light chain polypeptide comprises a detectable moiety.

12. The method of claim 11, wherein said detectable moiety is a protein binding site, a ligand binding site, or a tag comprising a further detectable moiety.

13. The method of claim 11, wherein the first and second light chain polypeptides are labeled with a different tag comprising a different detectable moiety.

14. The method of claim 11, wherein at least one light chain polypeptide comprises a tag which is capable of being captured onto a surface comprising an interactive surface layer, and further detected and quantified by a device.

15. The method of claim 11, wherein the detection moiety is detected by ELISA, SPR chips, bimolecular fluorescence complementation readout, Fluorescence-Activated Cell Sorting (FACS), Dissociation-Enhanced Lanthanide Fluorescent Immunoassay, fluorescence polarization/anisotropy (FP), fluorescent/Foerster resonance energy transfer (FRET, TR-FRET, HTRF), Bead-based proximity assay, or a combination thereof.

16. The method of claims 11, wherein the detectable moiety is detected by measurement of fluorescence, quenching, radioactivity or chemiluminescence.

17. The method of claim 3, wherein said heavy chain polypeptide is labeled with a tag.

18. The method of claim 17, wherein said tag labeling said heavy chain polypeptide is capable of being captured onto a surface comprising an interactive surface layer, and further detected and quantified by a device.

19. The method of claim 18, wherein the first and second light chain polypeptides are labeled with a different tag comprising different detectable moiety and said device is capable of detecting and quantifying the detectable moiety on at least one of said first and second light chain polypeptide.

20. The method of claim 19, wherein said device is capable of high throughput.

21. The method of claims 3, wherein said coexpressing step is in a host cell which is a bacterial cell, a yeast cell, or a mammalian cell.

22. The method of claim 21, wherein said mammalian cell is at least one of COS, CHO, BHK, HEK-293, NSO, 3T3 cells and derivatives thereof.

23. The method of claim 3, wherein at least one of said heavy and light chain polypeptides comprises a tag selected from 6×His, FLAG, HA, c-myc, s-FLAG, SBP, V5 and ABD.

24. The method of claim 3, wherein (c) comprises quantifying pairing between H1, L1, and L2 detected on a surface that captures heavy chain-paired polypeptide products, wherein said method comprises ELISA, SPR, biomolecular fluorescence complementation, Fluorescence-Activated Cell Sorting (FACS), Dissociation-Enhanced Lanthanide Fluorescent Immunoassay, fluorescence polarization/anisotropy (FP), fluorescent/Foerster resonance energy transfer (FRET, TR-FRET, HTRF), Bead-based proximity assay, or a combination thereof.

25. The method of claim 24, wherein the surface captures the heavy chain-paired polypeptide products from an environment that is a complex molecular mixture, a cell supernatant, cytoplasm of a host cell, or a combination thereof.

26. The method of claim 24, wherein the competition assay data is transmitted to a general purpose computer and wherein outputting of the data comprises storing the results on a data carrier.

27. The method of claim 26, optionally comprising analyzing the competition assay data.

28. The method of claim 27, further comprising building a LCCA library of paired heavy chain polypeptides and light chain polypeptides, based on analysis of the competition assay data.

29. The method of claim 3, comprising determining a relative pairing propensity of L1 to pair with H1 compared with the relative pairing propensity of L2 to pair with H1.

30. The method of claim 29, further comprising selecting an H1L1 pair that produces a high relative amount of H1L1 species over H1L2 species.

31. The method of claim 30, comprising comparing the ratios of H1L1 and H1L2 according to the following calculations:

$$R = \frac{[H1L1]}{[H1L2]}$$

$$S = \log\frac{[H1L1]}{[H1L2]}$$

$$P1 = 100 \cdot \frac{[H1L1]}{[H1L1]+[H1L2]}$$

$$P2 = 100 \cdot \frac{[H1L2]}{[H1L1]+[H1L2]}$$

wherein R is the ratio of the amount of H1L1 and H1L2; S is the logarithm of R, and is proportional to the free energy difference between the pairing of L1 with H1 and L2 with H1; and P1 and P2 are the percentages of the desired and less desired species, respectively such that $$S = \log\frac{P1}{P2}.$$

32. The method of claim 3, further comprising:
(d) co-expressing from polynucleotides encoding heavy and light chain polypeptides a second set of polypeptide constructs comprising:
a second heavy chain polypeptide comprising a VH and a CH1 region (H2); the first light chain polypeptide comprising a first VL and first CL region (L1); and the second light chain polypeptide comprising a second VL and second CL region (L2); wherein said second heavy chain polypeptide and said light chain polypeptides are expressed such that the total amount of the second heavy chain polypeptide is limiting: and wherein co-expressing the set of polypeptide constructs results in a second set of polypeptide products;
(e) isolating heavy chain-paired polypeptide products comprising the second heavy chain polypeptide paired with said first or second light chain polypeptide from the second set of polypeptide products; and
(f) quantifying the amount of the second heavy chain polypeptide paired with said first light chain polypeptide (H2L1), and the amount of the second heavy chain polypeptide paired with said second light chain polypeptide (H2L2) in the heavy chain-paired polypeptide products to generate competition assay data;

wherein the competition assay data from (c) and (f) identifies H1 polypeptides that selectively pair with L1 in the presence of L2, and H2 polypeptides that selectively pair with L2 in the presence of L1.

33. A high-throughput method of quantifying selectivity of a heavy chain polypeptide for pairing with a heavy chain polypeptide comprising the steps of:
(a) co-expressing from polynucleotides encoding heavy and light chain polypeptides a set of polypeptide constructs comprising:
  a first light chain polypeptide (L1) comprising a VL and a CL region;
  a first heavy chain polypeptide (H1) comprising a first VH and first CH1 region; and
  a second heavy chain polypeptide (H2) comprising a second VH and second CH1 region;
  wherein said light chain polypeptide and said heavy chain polypeptides are expressed such that the total amount of the light chain polypeptide is limiting; and wherein co-expressing the set of polypeptide constructs results in a set of polypeptide products;
(b) isolating light chain-paired polypeptide products comprising the light chain polypeptide paired with said first or second heavy chain polypeptide from the set of polypeptide products; and
(c) quantifying the amount of light chain polypeptide paired with said first heavy chain polypeptide (L1H1), and the amount of light chain polypeptide paired with said second heavy chain polypeptide (L1H2) in the light chain-paired polypeptide products to generate competition assay data;
wherein a greater amount of the light chain polypeptide paired with one of said first or second heavy chain polypeptides as compared to the other heavy chain polypeptide indicates selectivity of the light chain polypeptide for pairing with said first or second heavy chain polypeptides.

34. The method of claim 33, wherein the first or the second heavy chain polypeptide further comprise an Fc region.

35. The method of claim 33 wherein the first heavy chain polypeptide and the second heavy chain polypeptides are in a Fab format.

36. The method of claim 35, wherein at least one of said first heavy chain polypeptide and said second heavy chain polypeptide comprises a detectable label.

* * * * *